United States Patent
Kuersten et al.

(10) Patent No.: US 11,421,216 B2
(45) Date of Patent: Aug. 23, 2022

(54) NUCLEASE-BASED RNA DEPLETION

(71) Applicant: EPICENTRE TECHNOLOGIES CORPORATION, Madison, WI (US)

(72) Inventors: Scott Kuersten, Madison, WI (US); Frederick W. Hyde, Madison, WI (US); Asako Tetsubayashi, Madison, WI (US)

(73) Assignee: ILLUMINA, INC., San Diego, CA (US)

( * ) Notice: Subject to any disclaimer, the term of this patent is extended or adjusted under 35 U.S.C. 154(b) by 111 days.

(21) Appl. No.: 16/721,468

(22) Filed: Dec. 19, 2019

(65) Prior Publication Data

US 2020/0199572 A1 Jun. 25, 2020

Related U.S. Application Data

(60) Provisional application No. 62/847,797, filed on May 14, 2019, provisional application No. 62/783,869, filed on Dec. 21, 2018.

(51) Int. Cl.
| | | |
|---|---|---|
| *C12Q 1/68* | (2018.01) | |
| *C12N 15/10* | (2006.01) | |
| *C12Q 1/6806* | (2018.01) | |
| *C12Q 1/6848* | (2018.01) | |
| *C12Q 1/6876* | (2018.01) | |

(52) U.S. Cl.
CPC ..... *C12N 15/1003* (2013.01); *C12N 15/1024* (2013.01); *C12Q 1/6806* (2013.01); *C12Q 1/6848* (2013.01); *C12Q 1/6876* (2013.01)

(58) Field of Classification Search
CPC ..................................................... C12Q 1/68

USPC ........................................................ 435/6
See application file for complete search history.

(56) References Cited

U.S. PATENT DOCUMENTS

| | | | |
|---|---|---|---|
| 9,005,891 B2 | 4/2015 | Sinicropi et al. | |
| 9,428,794 B2 | 8/2016 | Farmer et al. | |
| 9,745,570 B2 | 8/2017 | Sooknanan | |
| 9,902,991 B2 | 2/2018 | Sinicropi et al. | |
| 2011/0111409 A1* | 5/2011 | Sinicropi | C12Q 1/6848 435/6.11 |
| 2014/0093882 A1* | 4/2014 | Farmer | C12Q 1/6848 435/6.12 |

FOREIGN PATENT DOCUMENTS

| | | | | |
|---|---|---|---|---|
| WO | 2014043133 A1 | 3/2014 | | |
| WO | 2014044724 A1 | 3/2014 | | |
| WO | WO-2014044724 A1 * | 3/2014 | ........... | C12Q 1/6834 |
| WO | 2017140659 A1 | 8/2017 | | |

OTHER PUBLICATIONS

NCBI Refernce Sequence AC_000021.2, *Homo sapiens* mitochondrion, complete genome (Dec. 8, 2008).*

(Continued)

*Primary Examiner* — Aaron A Priest
(74) *Attorney, Agent, or Firm* — McNeill Baur PLLC

(57) ABSTRACT

The present disclosure is related to methods and materials for depleting unwanted RNA species from a nucleic acid sample. In particular, the present disclosure describes how to remove unwanted rRNA, tRNA, mRNA or other RNA species that could interfere with the analysis, manipulation and study of target RNA molecules in a sample.

20 Claims, 11 Drawing Sheets
Specification includes a Sequence Listing.

OTHER PUBLICATIONS

"New England Biolabs® Introduces New Ribosomal RNA Depletion Technology from Genomic Health," Press Release, Aug. 19, 2014, available at https://www.neb.com/about-neb/news-and-press-releases/2014/08/19/new-ribosomal-rna-depletion-technology, 2 pages.
Champoux et al., "Ribonuclease H: properties, substrate specificity and roles in retroviral reverse transcription," FEBS J. 2009, 276, 1506-1516.
Mauro et al., "rRNA-like sequences occur in diverse primary transcripts: Implications for the control of gene expression," Proc. Natl. Acad. Sci. USA 1997, 94, 422-427.
Mignone and Pesole, "rRNA-like sequences in human mRNAs," Appl. Bioinformatics 2002, 1(3), 145-154 (abstract).
Morlan et al., "Selective depletion of rRNA enables whole transcriptome profiling of archival fixed tissue," PLOS One 2012, 7(8), e42882, pp. 1-8.
Schultz et al., "Sequence, distance, and accessibility are determinants of 5'-end-directed cleavages by retroviral RNases H*," J. Biol. Chem. 2006, 281(4), 1943-1955.
International Search Report and Written Opinion, International Application No. PCT/US2019/067582, dated Apr. 27, 2020, 11 pages.
Li et al., "Organism-Specific rRNA Capture System for Application in Next-Generation Sequencing", Plos One, vol. 8, No. 9, Sep. 20, 2013.
Langmead et al., Fast gapped-read alignment with Bowtie 2, Nature Methods, 2012, vol. 9, pp. 357-359.

* cited by examiner

| | Sample | Read length | Reads | % total alignment | % abundant | %unaligned | Median CV coverage uniformity | % stranded |
|---|---|---|---|---|---|---|---|---|
| 100 ng | 2181-144-HBR_100_1 | 76/76 | 21,129,299 | 95.99% | 3.83% | 4.01% | 0.59 | 98.29% |
| | 2181-144-HBR_100_2 | 76/76 | 16,836,087 | 94.45% | 4.14% | 5.55% | 0.64 | 98.04% |
| | 2181-144-HBR_100_3 | 76/76 | 20,318,497 | 95.41% | 3.68% | 4.59% | 0.6 | 98.30% |
| | 2181-144-HBR_100_4 | 76/76 | 18,415,870 | 93.57% | 6.19% | 6.43% | 0.71 | 98.34% |
| 10 ng | 2181-144-HBR_10_1 | 76/76 | 16,541,450 | 93.55% | 2.85% | 6.45% | 0.68 | 98.60% |
| | 2181-144-HBR_10_2 | 76/76 | 14,948,893 | 83.17% | 3.19% | 16.83% | 0.76 | 98.60% |
| | 2181-144-HBR_10_3 | 76/76 | 15,362,719 | 85.59% | 2.66% | 14.41% | 0.82 | 98.43% |
| | 2181-144-HBR_10_4 | 76/76 | 15,973,964 | 53.28% | 3.18% | 46.72% | 0.88 | 98.64% |
| 1 ng | 2181-144-HBR_1_1 | 76/76 | 18,165,680 | 76.35% | 3.13% | 23.65% | 0.82 | 98.46% |
| | 2181-144-HBR_1_2 | 76/76 | 18,608,299 | 79.14% | 4.46% | 20.86% | 0.74 | 98.66% |
| | 2181-144-HBR_1_3 | 76/76 | 17,073,720 | 71.65% | 4.04% | 28.35% | 0.76 | 98.63% |
| | 2181-144-HBR_1_4 | 76/76 | 18,655,503 | 75.76% | 4.13% | 24.24% | 0.79 | 98.61% |
| 100 ng | 2181_144_UHR_100_1 | 76/76 | 17,901,013 | 95.70% | 5.54% | 4.30% | 0.65 | 98.95% |
| | 2181_144_UHR_100_2 | 76/76 | 19,275,813 | 96.09% | 5.74% | 3.91% | 0.63 | 98.95% |
| | 2181_144_UHR_100_3 | 76/76 | 18,020,705 | 96.05% | 5.35% | 3.95% | 0.63 | 98.98% |
| | 2181_144_UHR_100_4 | 76/76 | 20,194,510 | 96.34% | 5.15% | 3.66% | 0.62 | 99.01% |
| 10 ng | 2181-144_UHR_10_1 | 76/76 | 18,156,567 | 95.69% | 4.21% | 4.31% | 0.67 | 99.06% |
| | 2181_144_UHR_10_2 | 76/76 | 17,589,818 | 95.47% | 2.93% | 4.53% | 0.68 | 99.04% |
| | 2181_144_UHR_10_3 | 76/76 | 11,663,050 | 80.16% | 3.95% | 19.84% | 0.88 | 99.11% |
| | 2181_144_UHR_10_4 | 76/76 | 14,233,408 | 62.15% | 37.92% | 37.85% | 1.32 | 97.92% |
| 1 ng | 2181-144_UHR_1_1 | 76/76 | 15,352,007 | 70.16% | 3.77% | 29.84% | 0.9 | 98.94% |
| | 2181_144_UHR_1_2 | 76/76 | 12,984,169 | 56.02% | 4.14% | 43.98% | 1.06 | 98.98% |
| | 2181_144_UHR_1_3 | 76/76 | 15,925,824 | 69.17% | 4.25% | 30.83% | 0.94 | 98.95% |
| | 2181_144_UHR_1_4 | 76/76 | 18,471,152 | 74.59% | 3.09% | 25.41% | 0.87 | 98.03% |

Figure 3

| Sample species | % Formamide | Read Length | Number of Reads | % Total Aligned | % Abundant | % Unaligned | Median CV Coverage Uniformity | % Stranded |
|---|---|---|---|---|---|---|---|---|
| Mouse | 0 | 76/76 | 20,906,336 | 95.89% | 6.77% | 4.11% | 0.7 | 98.81% |
| Mouse | 0 | 76/76 | 21,519,072 | 95.41% | 5.99% | 4.59% | 0.7 | 98.75% |
| Mouse | 0 | 76/76 | 16,278,898 | 95.81% | 4.95% | 4.19% | 0.69 | 98.78% |
| Mouse | 25 | 76/76 | 17,899,655 | 95.53% | 7.87% | 4.47% | 0.57 | 98.93% |
| Mouse | 25 | 76/76 | 14,429,705 | 95.90% | 5.77% | 4.10% | 0.59 | 98.92% |
| Mouse | 25 | 76/76 | 13,912,920 | 95.49% | 6.01% | 4.51% | 0.59 | 98.89% |
| Mouse | 25 | 76/76 | 29,429,014 | 95.97% | 6.44% | 4.03% | 0.58 | 98.91% |
| Mouse | 45 | 76/76 | 12,574,052 | 95.34% | 9.55% | 4.66% | 0.57 | 98.95% |
| Mouse | 45 | 76/76 | 25,749,347 | 95.40% | 8.10% | 4.60% | 0.59 | 98.91% |
| Mouse | 45 | 76/76 | 26,674,283 | 95.57% | 7.92% | 4.43% | 0.6 | 98.98% |
| Rat | 0 | 76/76 | 24,887,831 | 95.23% | 2.36% | 4.77% | 0.64 | 98.65% |
| Rat | 0 | 76/76 | 24,044,473 | 95.60% | 1.77% | 4.40% | 0.65 | 98.77% |
| Rat | 0 | 76/76 | 24,074,413 | 95.78% | 1.71% | 4.22% | 0.67 | 98.65% |
| Rat | 25 | 76/76 | 18,888,445 | 95.53% | 2.08% | 4.47% | 0.66 | 98.81% |
| Rat | 25 | 76/76 | 19,992,000 | 95.23% | 3.40% | 4.77% | 0.52 | 99.02% |
| Rat | 25 | 76/76 | 22,550,033 | 95.65% | 3.71% | 4.35% | 0.52 | 99.01% |
| Rat | 25 | 76/76 | 19,816,333 | 95.70% | 3.55% | 4.30% | 0.52 | 98.98% |
| Rat | 25 | 76/76 | 23,590,623 | 94.86% | 4.18% | 5.14% | 0.62 | 99.03% |
| Rat | 45 | 76/76 | 14,029,563 | 95.59% | 8.87% | 4.41% | 0.51 | 99.06% |
| Rat | 45 | 76/76 | 13,833,972 | 95.55% | 7.81% | 4.45% | 0.5 | 99.04% |
| Rat | 45 | 76/76 | 12,156,542 | 95.50% | 7.89% | 4.50% | 0.51 | 99.04% |
| Rat | 45 | 76/76 | 14,414,597 | 95.47% | 8.21% | 4.53% | 0.5 | 99.04% |

Figure 4

NUCLEASE-BASED RNA DEPLETION

CROSS-REFERENCE TO RELATED APPLICATIONS

This application claims the benefit of priority of US Provisional Application Nos. 62/783,869, filed Dec. 21, 2018, and 62/847,797, filed May 14, 2019, each of which is incorporated by reference herein in its entirety for any purpose.

SEQUENCE LISTING

The present application is filed with a Sequence Listing in electronic format. The Sequence Listing is provided as a file entitled "2019-12-09_01243-0012-00US_Sequence_Listing_ST25.txt" created on Dec. 9, 2019, which is 94,208 bytes in size. The information in the electronic format of the sequence listing is incorporated herein by reference in its entirety.

BACKGROUND

Unwanted RNA in a nucleic acid sample, like a nucleic acid sample taken from human cells or tissues, can complicate the analysis of that sample, analysis such as gene expression analysis, microarray analysis and sequencing of a sample. As ribosomal RNA (rRNA) comprises roughly 95% of the RNA in a cell its presence is one example of an RNA species that can interfere and obfuscate results of a target nucleic acid in a sample, or those nucleic acids that a researcher or diagnostician might want to understand more about. For example, unwanted rRNA species can make it especially difficult to analyze RNA molecules of interest in a sample, such as tRNA or mRNA. This is an ever-present problem particularly for tissues that have been fixed, for example fixed by formalin and then embedded in wax such as formalin fixed paraffin embedded (FFPE) tissues from biopsies. Without removing the rRNA species from FFPE tissues they can interfere with the measurement and characterization of target RNA in the tissue thereby making it extremely difficult to derive medically actionable information from the target RNAs such as disease and cancer identification, potential treatment options and disease or cancer diagnosis and prognosis. While FFPE tissue is an example, the same issues with rRNA hold true for samples of all kinds such a blood, cells, and other types of nucleic acid containing samples.

Current commercially available methods for depleting undesired RNA from a nucleic sample include RiboZero® (Epicentre) and NEBNext® rRNA Depletion kits (NEB) and RNA depletion methods as described in U.S. Pat. Nos. 9,745,570 and 9,005,891. However, these methods, while being useful in depleting RNA, have their own disadvantages, including ease of use, high sample input requirements, technician hands on time, cost, and/or efficiency in depleting undesired RNA from a sample. What are needed are materials and methods that can more easily or cost effectively deplete unwanted RNA species from a sample thereby unlocking information in the target RNA which might have been hidden such as rare or difficult to identify sequence variants. Straightforward and reliable methods as described in this disclosure can greatly increase the availability of target RNA molecules for testing purposes, thereby discovering the information they hold about the sample and the organism from which it derives.

SUMMARY OF THE INVENTION

Nucleic acid samples such as those from eukaryotes or prokaryotes contain multitude nucleic acids, many of which are not of interest to a researcher. Researchers oftentimes wish to study a specific type of a nucleic acid, such as either DNA or RNA. When studying RNA, the sample of interest can contain many different types of RNA species that can overwhelm and hide the target RNA that is the focus of study. As such, RNA depletion refers to removing unwanted RNA and/or DNA species from a nucleic acid sample thereby leaving a nucleic acid sample enriched with the desired RNA for study.

The present disclosure provides a solution for depleting a nucleic acid sample of an overabundance of unwanted RNA species prior to further study. For example, an RNA sample of interest not only includes the target RNA to be studied, but also includes abundant transcripts like rRNA, globin mRNA, viral contaminates, or any other unwanted nucleic acids that can dominate the sample and swamp out the target of interest, thereby greatly decreasing a researcher's ability to accurately analyze the desired portion of the transcriptome.

Therefore, depleting unwanted RNA from a nucleic acid sample prior to analysis, such as expression microarrays or sequencing, increases the specificity and accuracy of analysis for the desired RNA targets. In the present disclosure, depletion of off-target RNA through degradation of specific DNA:RNA hybrids allows for efficient removal of unwanted RNA species from a sample prior to library preparation and analysis. Once a sample is depleted of unwanted RNA species, the remaining target RNA can be converted to cDNA. Obtaining actionable data as a result of a robust sample can lead to a better understanding and potential treatment options for cancer prognostics and diagnostics, a better understanding of our microbiome and its importance in our and other eukaryotic systems, a more thorough understanding of expression analysis of genes of interest, and the like.

In one embodiment, the present disclosure describes a method for depleting off-target RNA molecules from a nucleic acid sample comprising:

a) contacting a nucleic acid sample comprising at least one RNA or DNA target sequence and at least one off-target RNA molecule with a probe set comprising at least two DNA probes complementary to discontiguous sequences along the full length of the at least one off-target RNA molecule, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; and b) contacting the DNA:RNA hybrids with a ribonuclease that degrades the RNA from the DNA:RNA hybrids, thereby degrading the off-target RNA molecules in the nucleic acid sample to form a degraded mixture.

In one embodiment, the present disclosure relates to a composition comprising a probe set comprising at least two DNA probes complementary to discontiguous sequences along the full length of at least one off-target RNA molecule (e.g., at least 5 or at least 10 bases apart along the full length) in a nucleic acid sample. In some embodiments, the composition also comprises a ribonuclease capable of degrading RNA in a DNA:RNA hybrid. In another embodiment, the present disclosure relates to a composition comprising a probe set comprising at least two DNA probes hybridized to at least one off-target RNA molecule, wherein each DNA probe is hybridized at least 5, or at least 10, bases apart along the length of the off-target RNA molecule from any other DNA probe in the probe set.

In one embodiment, the present disclosure describes a kit comprising a probe set comprising at least two DNA probes complementary to discontiguous sequences along the full length of at least one off-target rRNA molecule (e.g., at least 5 bases apart or at least 10 bases apart along the full length) in a nucleic acid sample and a ribonuclease capable of degrading RNA in a DNA:RNA hybrid.

In one embodiment, the present disclosure describes a method of supplementing a probe set for use in depleting off-target RNA nucleic acid molecules from a nucleic acid sample comprising: a) contacting a nucleic acid sample comprising at least one RNA or DNA target sequence and at least one off-target RNA molecule from a first species with a probe set comprising at least two DNA probes complementary to discontiguous sequences along the full length of the at least one off-target RNA molecule from a second species, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; b) contacting the DNA:RNA hybrids with a ribonuclease that degrades the RNA from the DNA:RNA hybrids, thereby degrading the off-target RNA molecules in the nucleic acid sample to form a degraded mixture; c) separating the degraded rRNA from the degraded mixture; d) sequencing the remaining RNA from the sample; e) evaluating the remaining RNA sequences for the presence of off-target RNA molecules from the first species, thereby determining gap sequence regions; and f) supplementing the probe set with additional DNA probes complementary to discontiguous sequences in one or more of the gap sequence regions.

BRIEF DESCRIPTION OF THE FIGURES

FIG. 3 shows exemplary next-generation sequencing (NGS) sequence data for rRNA depleted samples of Human Brain RNA (HBR) and Universal Human RNA (UHR) comparing different amounts of sequenced sample (100 ng, 10 ng, or 1 ng).

FIG. 4 shows exemplary NGS sequence data for rRNA depleted samples from mouse RNA and rat RNA using different concentrations of formamide (0%, 25%, 45%) added to the rRNA depletion workflow.

DETAILED DESCRIPTION

Figure 1:
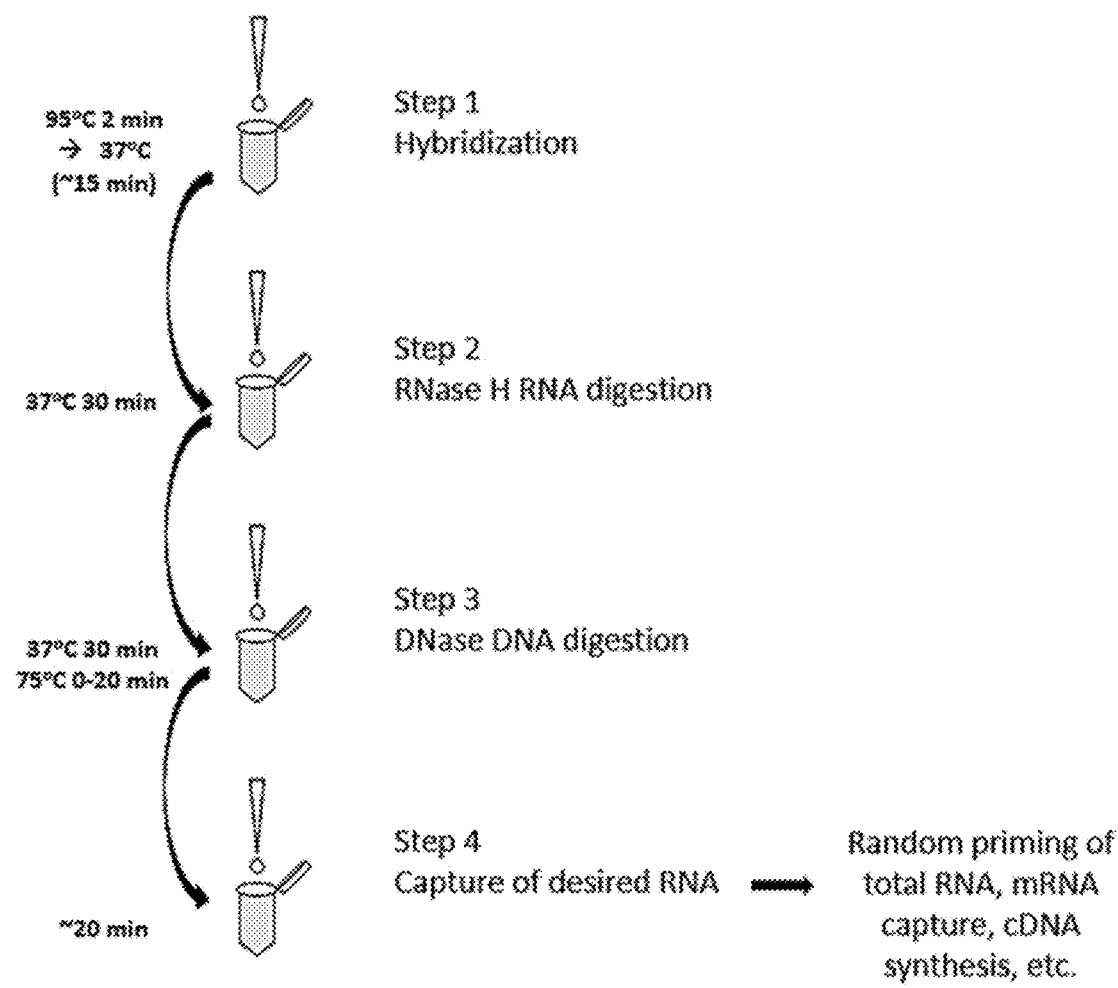
FIG. 1 shows an exemplary workflow for performing depletion of RNA species from a sample. Step 1 includes nucleic acid denaturation followed by addition of depletion DNA probes and hybridization of the probes with the unwanted RNA species, thereby creating DNA:RNA hybrids. Step 2 includes digestion of the RNA from the DNA:RNA hybrids using a ribonuclease such as RNase H. Step 3 includes digesting residual DNA probes from the degraded mixture by addition of DNase. Step 4 includes capturing the remaining target RNA in the sample, which is optionally followed by additional manipulations that will eventually result in a sample depleted of unwanted RNA species that can be sequenced, exposed to microarray expression analysis, qPCR, or other analysis techniques.

Creating nucleic acid libraries from RNA for sequencing is oftentimes difficult due to an abundance of unwanted transcripts such as ribosomal RNA, globin mRNA, viral contaminants, and the like that can dominate a sample and swamp out the RNA sequences of interest. If the unwanted transcripts are not removed, analysis of the transcriptome which would have prognostic, diagnostic or research benefit could be compromised. Therefore, depleting unwanted RNA from a nucleic acid sample prior to analysis such as sequencing or other downstream applications can increase the specificity and accuracy of the desired analysis.

The present disclosure describes methods and materials useful in depleting unwanted RNA species from a nucleic acid sample such that the RNA of importance can be studied and is not lost in the sea of undesired RNA transcripts.

Compared to existing methods for RNA depletion, the disclosed method can utilize smaller amounts of input total RNA while still maintaining comparable performance metrics. Therefore, the disclosed method can be used when a researcher has small amounts of starting material which other methods would not be able to accommodate. Further, the disclosed method can be performed with one pool of probes that target a variety of different organismal unwanted RNA species simultaneously without compromising depletion efficiency. For example, the present disclosure can simultaneously deplete unwanted eukaryotic and prokaryotic RNA species from an RNA sample, including but not limited to human, bacterial, viral and/or Archaea sources of unwanted RNA.

A nucleic acid sample or mixture refers to a sample that contains RNA or DNA or both, including both undesired (off-target or unwanted) and desired (target) nucleic acids. The DNA or RNA in the sample can be either unmodified or modified and includes, but is not limited to, single or double stranded DNA or RNA or derivatives thereof (e.g., some regions of the DNA or RNA are double stranded whereas concurrently other regions of the DNA or RNA are single stranded) and the like. In general, a nucleic acid sample includes all chemically, enzymatically, and/or metabolically modified forms of nucleic acids as well as all unmodified forms of nucleic acids, or combinations thereof. A nucleic acid sample can contain both wanted and unwanted nucleic acids such as genomic DNA or total cellular RNA or a combination of both. Unwanted nucleic acids include those nucleic acids from eukaryotes that are not targeted for study as well as contaminating nucleic acids from bacteria, viruses, Archaea species, and the like. Wanted or desired nucleic acids are those nucleic acids that are the basis or focus of study, the target nucleic acids. For example, a researcher may desire to study mRNA expression analysis, wherein rRNA, tRNA and DNA would be considered unwanted nucleic acids and mRNA is the target nucleic acid. As well, study of total RNA could be desired, whereas the rRNA, mRNA and DNA would be considered unwanted or undesired nucleic acids and the total RNA the target nucleic acid. Unwanted RNA includes, but is not limited to, ribosomal RNA (rRNA), mitochondrial rRNA, nuclear rRNA, mRNA such as globin RNAs, or transfer or tRNA, or a mixture thereof. In some embodiments, off-target RNA is rRNA. In some embodiments, off-target RNA is globin mRNA.

For example, a nucleic acid sample could contain the desired messenger RNA (mRNA) or total RNA while also including undesired ribosomal RNA (rRNA), transfer RNAs (tRNA) and perhaps undesired DNA. General methods for RNA extraction from a gross sample, like blood, tissue, cells, fixed tissues, etc., are well known in the art, as found in Current Protocols for Molecular Biology (John Wiley & Sons) and multitude molecular biology methods manuals. RNA isolation can be performed by commercially available purification kits, for example Qiagen RNeasy mini-columns, MasterPure Complete DNA and RNA Purification Kits (Epicentre), Parrafin Block RNA Isolation Kit (Ambion), RNA-Stat-60 (Tel-Test) or cesium chloride density gradient centrifugation. The current methods are not limited by how the RNA is isolated from a sample prior to RNA depletion.

There is an inherent skepticism that mixing probes targeting bacterial rRNA and human rRNA into the same pool would lead to extensive off-target depletion of desirable transcripts (Mauro et al., Proc. Natl. Acad. Sci. USA 1997, 94:422-427; Mignone and Pesole, Appl. Bioinformatics 2002, 1:145-54). Surprisingly, research performed while developing the disclosed methods demonstrates this isn't the case, as the specificity of the DNA probe hybridization with the unwanted RNA transcripts results in a sample efficiently depleted of unwanted RNA species. It was also discovered that the addition of a destabilizer such as formamide helps remove some unwanted RNA that was shown to be more problematic to deplete if formamide was not present. Although it is not necessary to understand the way in which formamide helps in removing those RNA, it is thought that the formamide may serve to relax structural barriers in the unwanted RNA so that the DNA probes can bind more efficiently. Further, the addition of formamide has demonstrated the added benefit of improving the detection of some non-targeted transcripts possibly by denaturing/relaxing regions of the mRNAs, for example, that have very stable secondary or tertiary structures and are not normally well represented well in other library preparation methods.

Nucleic Acid Samples or Mixtures

The present disclosure is not limited to the source of a nucleic acid sample, for example, the source could be from eukaryotes or prokaryotes including but not limited to humans, non-human primates, mammals, birds, reptiles, plants, bacteria, viruses, nucleic acids found in soils, water or other liquids and other environmental samples. The sample could be obtained from cells, tissues, organs, the environment, lysates, etc. and could come from any state of a sample such as fresh, frozen, lyophilized and reconstituted, or a fixed sample such as from a tissue or biopsy specimen that has been formalin fixed paraffin embedded (FFPE) or other cytological or histological sample manipulation.

The nucleic acid sample that could benefit from the RNA depletion methods could be from any species, eukaryotic or prokaryotic, such as humans, non-humans, mice, rats, bacteria, etc. and could include single or multiple species in one sample. Additionally, the present depletion methods could be used on fresh or preserved samples such as biopsy or tissue samples, including samples that have been processed using formalin and embedded in paraffin (e.g., formalin fixed paraffin embedded, FFPE, samples). In some embodiments, a nucleic acid sample is from a human or non-human source such as non-human eukaryotes, bacteria, viruses, plants, soil or a mixture thereof. Once a sample is depleted of unwanted RNA species, the remaining desired targets can be converted to cDNA for further processing as known to those skilled in the art.

In some embodiments, a nucleic acid sample is from a human or a non-human primate. In some embodiments, a nucleic acid sample is from a rat or a mouse. In some embodiments, a nucleic acid sample comprises nucleic acids of non-human origin. In some embodiments, nucleic acids of non-human origin are from non-human eukaryotes, bacteria, viruses, plants, soil, or a mixture thereof.

Depletion Methods

As such, unwanted or undesired RNA in a nucleic acid sample is depleted by the described methods. The unwanted RNA is converted to a DNA:RNA hybrid by hybridizing partially or completely complementary DNA probes to the unwanted RNA molecules. Methods for hybridizing nucleic acid probes to nucleic acids are well established in the sciences and whether a probe is partially or completely complementary with the partner sequence, the fact that a DNA probe hybridizes to the unwanted RNA species following washes and other manipulations of the sample demonstrates a DNA probe that can be used in methods of the present disclosure. The unwanted RNA set for depletion can be from any eukaryotic species, for example, human, mice, rats, etc., where depletion of RNA from a sample might result in more favorable downstream studies such as sequencing (e.g., fewer results from unwanted nucleic acid species). DNA can also be considered an unwanted nucleic acid if the target for study is an RNA, at which point DNA can also be removed by depletion.

In one embodiment, the present disclosure describes a method for depleting off-target RNA molecules from a nucleic acid sample comprising:

a) contacting a nucleic acid sample comprising at least one RNA or DNA target sequence and at least one off-target RNA molecule with a probe set comprising at least two DNA probes complementary to discontiguous sequences along the full length of the at least one off-target RNA molecule, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; and
b) contacting the DNA:RNA hybrids with a ribonuclease that degrades the RNA from the DNA:RNA hybrids, thereby degrading the off-target RNA molecules in the nucleic acid sample to form a degraded mixture.

In one embodiment, an RNA sample is denatured in the presence of the DNA probes. An exemplary workflow is demonstrated in FIG. 1. In the example in FIG. 1, the DNA probes are added to the denatured RNA sample (denatured at 95° C. for 2 min.) whereupon cooling the reaction to 37° C. for 15-30 min results in hybridization of the DNA probes to their respective target RNA sequences thereby creating DNA:RNA hybrid molecules.

In some embodiments, contacting with the probe set comprises treating the nucleic acid sample with a destabilizer. In some embodiments, a destabilizer is heat or a nucleic acid destabilizing chemical. In some embodiments, a nucleic acid destabilizing chemical is betaine, DMSO, formamide, glycerol, or a derivative thereof, or a mixture thereof. In some embodiments, a nucleic acid destabilizing chemical is formamide or a derivative thereof, optionally wherein the formamide or derivative thereof is present at a concentration of from about 10 to 45% of the total hybridization reaction volume. In some embodiments, treating the sample with heat comprises applying heat above the melting temperature of the at least one DNA:RNA hybrid.

In some embodiments, formamide is added to the hybridization reaction regardless of RNA sample source (e.g., human, mouse, rat, etc.). For example, in some embodiments, hybridizing to the DNA probes is performed in the presence of at least 3%, 5%, 10%, 20%, 25%, 30%, 35%, 40%, or 45% by volume of formamide. In one embodiment, a hybridization reaction for RNA depletion includes approximately 25% to 45% by volume of formamide.

Following the hybridization reaction, a ribonuclease that degrades RNA from a DNA:RNA hybrid is added to the reaction. In some embodiments, a ribonuclease is RNase H or Hybridase. RNase H (NEB) or Hybridase (Lucigen) are examples of enzymes that will degrade RNA from a DNA:RNA hybrid. Degradation by a ribonuclease such as RNase H or Hybridase degrades the RNA into small molecules that can then be removed. For example, RNase H is reported to digest RNA from a DNA:RNA hybrid approximately every 7-21 bases (Schultz et al., J. Biol. Chem. 2006, 281:1943-1955; Champoux and Schultz, FEBS J. 2009, 276:1506-1516). In some embodiments, the digestion of the RNA of the DNA:RNA hybrid can occur at 37° C. for approximately 30 min as described in FIG. 1, Step 2, and Example 1.

In some embodiments, following DNA:RNA hybrid molecule digestion, the remaining DNA probes and any off-target DNA in the nucleic acid sample are degraded. Thus, in some embodiments, the methods comprise contacting the ribonuclease-degraded mixture with a DNA digesting enzyme, thereby degrading DNA in the mixture. In some embodiments, the digested sample is exposed to a DNA digesting enzyme such as DNase I, which degrades the DNA probes. The DNase DNA digestion reaction is incubated, for example, at 37° C. for 30 min, after which point the DNase enzyme can be denatured at 75° C. for a period of time as necessary to denature the DNase, for example for up to 20 min.

In some embodiments, the depletion method comprises separating the degraded RNA from the degraded mixture. In some embodiments, separating comprises purifying the target RNA from the degraded RNA (and degraded DNA if present), for example, using a nucleic acid purification medium, such as RNA capture beads, such as RNAClean XP beads (Beckman Coulter). Thus, in some embodiments, following the enzymatic digestion(s), the target RNA can be enriched by removing the degraded products while leaving the desired and longer RNA targets behind. Suitable enrichment methods include treating the degraded mixture with magnetic beads which bind to the desired fragment size of the enriched RNA targets, spin columns, and the like. In some embodiments, magnetic beads such as AMPure XP beads, SPRISelect beads, RNAClean XP beads (Beckman Coulter) can be used, as long as the beads are free of RNases (e.g., Quality Controlled to be RNase free). These beads provide different size selection options for nucleic acid binding, for example RNAClean XP beads target 100 nt or longer nucleic acid fragments and SPRISelect beads target 150 to 800 nt nucleic acid fragments and do not target shorter nucleic acid sequences such as the degraded RNA and DNA that results from the enzymatic digestions of RNase H and DNase. If mRNA is the target RNA to be studied, then the mRNA can be further enriched by capture using, for example, beads that comprise oligodT sequences for capturing the mRNA adenylated tails. Methods of mRNA capture are well known by skilled artisans.

Once the target RNA has been purified away from the reaction components including the undesired degraded nucleic acids, additional sample manipulation can occur. In the present disclosure, Examples 2 and 3 provide exemplary workflows for cDNA synthesis from the enriched target total RNA followed by an exemplary library preparation workflow that is typical for subsequent sequencing on, for example, an Illumina sequencer. However, it should be understood that these workflows are exemplary only and a skilled artisan will understand that the enriched RNA can be used in multitude additional applications such as PCR, qPCR, microarray analysis, and the like either directly or following additional manipulation such as converting the RNA to cDNA by using established and will understood protocols.

The methods described herein for RNA depletion will result in a sample enriched with the target RNA molecules. For example, the methods described herein result is a depleted RNA sample comprising less than 15%, 13%, 11%, 9%, 7%, 5%, 3%, 2% or 1% or any range in between of the unwanted RNA species. The enriched RNA sample then comprises at least 99%, 98%, 97%, 95%, 93%, 91%, 89% or 87% or any range in between of the target total RNA. Once the sample has been enriched it can be used for library preparation or other downstream manipulations.

DNA Probe Sets/DNA Probes

A DNA probe refers to a single stranded DNA oligonucleotide that has sequence complementarity to unwanted RNA species. The DNA probe sequence can be partly or completely complementary to the undesired RNA for depletion in the nucleic acid sample. The unwanted RNA for depletion includes, but is not limited to, rRNA, tRNA, and mRNA, and mixtures thereof. In some embodiments, each DNA probe is from about 10 and 100 nucleotides long, or from about 20 and 80 nucleotides long, or from about 40 to 60 nucleotides long, or about 50 nucleotides long. The DNA probes are capable of hybridizing to the unwanted RNA species, thereby creating DNA:RNA hybrid molecules. While in some embodiments, at least two DNA probes hybridize to a particular off-target RNA molecule, the DNA probes do not cover the entire length of an unwanted RNA molecule sequence. For example, in some embodiments, a probe set leaves gaps or regions of the unwanted RNA without a complementary DNA probe in the probe set. The DNA probes hybridize, completely or partly, to the unwanted RNA in a non-overlapping manner, leaving gaps of at least 5, 10, 15, 20, 30, 40, 50, 60, 70, 80 or more nucleotides between the resultant DNA:RNA hybrids. Thus, in some embodiments, each DNA probe is hybridized at least 5, or at least 10, bases apart along the full length of the at least one off-target RNA molecule from any other DNA probe in the probe set. As such, the unwanted RNA in its entirety is not completely hybridized to DNA probes. Further, the present disclosure provides for a plurality of DNA probes that hybridize to a single RNA for depletion as such there is not a "one DNA probe for one RNA", but instead multiple discontinuous DNA probes in a probe set that target a given unwanted RNA. For example, in some embodiments, for a given RNA set for depletion, a DNA probe set is used where each probe is approximately 20-80 nucleotides long and each probe hybridizes to the unwanted RNA anywhere from 5-15 nucleotides away from another DNA probe in the set. A DNA probe can be completely or partially complementary to a particular location on the RNA to be depleted, for example the DNA probe sequence can be at least 80%, 85%, 90%, 95%, or 100% complementary, or any range in between, to the target location on an RNA transcript to be depleted. The only limitation to complementarity is that the DNA probe should hybridize to the target RNA to be depleted in such a manner that a DNA:RNA hybrid results that is enzymatically digestible as described herein. In some cases, mRNA is the target of interest and not targeted for depletion, in which case the DNA probes do not comprise a polyT sequence so that the probes will not hybridize to mRNA species. In some embodiments, the DNA probes do not comprise a tag with a capture moiety such as biotin, avidin, streptavidin, or a magnetic bead that would allow for depletion of the hybrid by physical means, whereas in other embodiments the DNA probes do comprise a tag with a capture moiety such as biotin, avidin, streptavidin, or a magnetic bead that would allow for depletion of the hybrid by physical means.

In some embodiments, a probe set comprises at least DNA probes that hybridize to off-target RNA molecules from humans and bacteria. In some embodiments, a probe set comprises at least DNA probes that hybridize to off-target RNA molecules from humans, bacteria, and Archaea. In some embodiments, a probe set comprises at least DNA probes that hybridize to off-target RNA molecules from humans, bacteria, mouse, and rat. In some embodiments, a probe set comprises at least DNA probes that hybridize to off-target RNA molecules from humans, bacteria, mouse, rat, and Archaea. In some embodiments, the off-target RNA molecules from bacteria are from Gram-positive bacteria or Gram-negative bacteria, or a mixture thereof. In some embodiments, a probe set comprises at least two DNA probes that hybridize to one or more off-target RNA molecules from an Archaea species. In some embodiments, a probe set comprises at least two DNA probes complementary to two or more rRNA sequences from an Archaea species.

In some embodiments, a probe set comprises at least two DNA probes that hybridize to at least one, or at least two, off-target RNA molecules selected from 28S, 23S, 18S, 5.8S, 5S, 16S, 12S, HBA-A1, HBA-A2, HBB, HBB-B1, HBB-B2, HBG1, and HBG2. In some embodiments, the probe set comprises at least two DNA probes complementary to two or more rRNA sequences selected from the group consisting of 28S, 23S, 18S, 5.8S, 5S, 16S, 12S, HBA-A1, HBA-A2, HBB, HBB-B1, HBB-B2, HBG1, and HBG2. In some embodiments, a probe set comprises at least two DNA probes that hybridize to one or more, or two or more, off-target RNA molecules selected from 28S, 18S, 5.8S, 5S, 16S, and 12S from humans. In some embodiments, a probe set comprises at least two DNA probes that hybridize to one or more, or two or more, off-target RNA molecules from rat and/or mouse, optionally selected from rat 16S, rat 28S, mouse 16S, and mouse 28S, and combinations thereof. In some embodiments, a probe set comprises at least two DNA probes that hybridize to one or more off-target RNA molecules selected from HBA-A1, HBA-A2, HBB, HBB-B1, HBB-B2, HBG1, and HBG2 from hemoglobin. In some embodiments, a probe set comprises at least two DNA probes that hybridize to one or more off-target RNA molecules selected from 23S, 16S, and 5S from Gram positive and/or Gram negative bacteria. Globin mRNAs for depletion can include, but are not limited to, those found in rodents such as mouse or rat including HBA-A1, HBA-A2, HBB, HBB-B1, HBB-B2, and those found in humans including HBA-A1, HBA-A2, HBB, HGB1 and HGB2. Mitochondrial rRNAs suitable for depletion include 18S and 12S (humans and rodents). Nuclear rRNAs suitable for depletion include 28S, 18S, 5.8S and 5S (humans and rodents) and prokaryotic rRNAs including 5S, 16S and 23S. In some samples, the depletion of rRNAs from Archaea species may also be desired, such as rRNAs 23S, 16S or 5S. In further embodiments, the probe set comprises at least two DNA probes complementary to two or more rRNA sequences selected from the group consisting of Gram positive or Gram negative bacterial rRNA 5S, 16S and 23S. In some embodiments, the probe set comprises at least two (or at least five, or at least 10, or at least 20) DNA probes complementary to each of human 28S, 18S, 5.8S, 5S, 16S, and 12S, globin mRNA HBA-A1, HBA-A2, HBB, HBG1, and HBG2, and Gram positive or Gram negative bacterial rRNA 5S, 16S and 23S. In some embodiments, the probes to a particular off-target RNA molecule are complementary to about 80 to 85% of the sequence of the off-target RNA molecule, with gaps of at least 5, or at least 10 bases between each probe hybridization site.

In some embodiments, a probe set comprises two or more, or five or more, or 10 or more, or 25 or more, or 50 or more, or 100 or more, or 150 or more, or 200 or more, or 250 or more, or 300 or more, or 333 sequences from SEQ ID NOs: 1-333 (human, Gram-positive bacteria, and Gram-negative bacteria). In some embodiments, a probe set comprises two or more, or five or more, or 10 or more, or 25 or more, or 50 or more, or 100 or more, or 150 or more, or 200 or more, or 250 or more, or 300 or more, or 350 or more, or 400 or more, or 428 sequences from SEQ ID NOs: 1-428 (human, Gram-positive bacteria, Gram-negative bacteria, Archaea, mouse, and rat). In some embodiments, a probe set comprises two or more, or five or more, or 10 or more, or 25 or more, or 50 or more, or 100 or more, or 150 or more, or 200 or more, or 250 or more, or 300 or more, or 350 or more, or 377 sequences from SEQ ID NOs: 1-377 (human, Gram-positive bacteria, Gram-negative bacteria, and Archaea). In some embodiments, a probe set comprises two or more, or five or more, or 10 or more, or 25 or more, or 50 or more, or 100 or more, or 150 or more, or 200 or more, or 250 or more, or 300 or more, or 350 or more, or 384 sequences from SEQ ID NOs: 1-333 (human, Gram-positive bacteria, and Gram-negative bacteria) and SEQ ID NOs: 378-428 (mouse and rat). In some embodiments, a probe set comprises two or more, or five or more, or 10 or more, or 25 or more, or 44 sequences from SEQ ID NOs: 334-377 (Archaea). In some embodiments, a probe set comprises two or more, or five or more, or 10 or more, or 25 or more, or 50 or more, or 51 sequences from SEQ ID NOs: 378-428 (mouse and rat).

In some embodiments, the DNA probes are partially or completely complementary and comprise sequences that hybridize to human 28S, 18S, 5.8S and/or 5S rRNA, for example DNA probe sequences as shown in Table 1, SEQ ID NO: 40 through SEQ ID NO: 150. In a second embodiment, the DNA probes include sequences that hybridize to mitochondrial rRNAs 16S and/or 12S, for example DNA probe sequences as shown in Table 1, SEQ ID NO: 1 through SEQ ID NO: 39. In other embodiments, the DNA probes include sequences that hybridize to hemoglobin mRNA including HBA-A1, HBA-A2, HBB, HBB-B1, HBB-B2, HBG1, and/or HBG2, for example DNA probe sequences as shown in Table 1, SEQ ID NO: 151 through SEQ ID NO: 194. In some embodiments, the DNA probes include sequences that hybridize to bacterial rRNAs such as Gram positive and/or Gram negative bacterial rRNAs 23S, 16S and/or 5S, for example DNA probe sequences as shown in Table 1, SEQ ID NO: 195 through SEQ ID NO: 262 (Gram negative bacterial representative *E. coli*) and SEQ ID NO: 263 through SEQ ID NO: 333 (Gram positive bacterial representative *Bacillus subtilis*). In other embodiments, the DNA probes include sequences that hybridize to Archaea rRNAs, such as rRNAs 23S, 16S and/or 5S, for example the DNA probe sequences shown in Table 1, SEQ ID NO: 334 through SEQ ID NO: 384, which hybridize to rRNAs from Archaea species *Methanobrevibacter smithii*. In some embodiments, the DNA probes include sequences that hybridize to mouse rRNAs, such as mouse 16S and/or 28S, for example the DNA probe sequences shown in Table 1, SEQ ID NO: 385 through SEQ ID NO: 393 and SEQ ID NO:400 through SEQ ID NO: 419. In some embodiments, the DNA probes include sequences that hybridize to rat rRNAs, such as rat 16S and/or 28S, for example the DNA probe sequences shown in Table 1, SEQ ID NO: 394 through SEQ ID NO: 399 and SEQ ID NO: 420 through SEQ ID NO: 428.

TABLE 1

DNA probe sequences for unwanted RNA depletion

| SEQ ID NO | Probe name | Probe sequence 5'-3' |
|---|---|---|
| 1 | 12S_P1 | GTTCGTCCAAGTGCACTTTCCAGTACACTTACCATGTTACGACTTGTCTC |
| 2 | 12S_P2 | TAGGGGTTTTAGTTAAATGTCCTTTGAAGTATACTTGAGGAGGGTGACGG |
| 3 | 12S_P3 | TTCAGGGCCCTGTTCAACTAAGCACTCTACTCTCAGTTTACTGCTAAATC |
| 4 | 12S_P4 | AGTTTCATAAGGGCTATCGTAGTTTTCTGGGGTAGAAAATGTAGCCCATT |
| 5 | 12S_P5 | GGCTACACCTTGACCTAACGTCTTTACGTGGGTACTTGCGCTTACTTTGT |
| 6 | 12S_P6 | TTGCTGAAGATGGCGGTATATAGGCTGAGCAAGAGGTGGTGAGGTTGATC |
| 7 | 12S_P7 | CAGAACAGGCTCCTCTAGAGGGATATGAAGCACCGCCAGGTCCTTTGAGT |
| 8 | 12S_P8 | GTAGTGTTCTGGCGAGCAGTTTTGTTGATTTAACTGTTGAGGTTTAGGGC |
| 9 | 12S_P9 | ATCTAATCCCAGTTTGGGTCTTAGCTATTGTGTGTTCAGATATGTTAAAG |
| 10 | 12S_P10 | ATTTTGTGTCAACTGGAGTTTTTTACAACTCAGGTGAGTTTTAGCTTTAT |
| 11 | 12S_P11 | CTAAAACACTCTTTACGCCGGCTTCTATTGACTTGGGTTAATCGTGTGAC |
| 12 | 12S_P12 | GAAATTGACCAACCCTGGGGTTAGTATAGCTTAGTTAAACTTTCGTTTAT |
| 13 | 12S_P13 | ACTGCTGTTTCCCGTGGGGGTGTGGCTAGGCTAAGCGTTTTGAGCTGCAT |
| 14 | 12S_P14 | GCTTGTCCCTTTTGATCGTGGTGATTTAGAGGGTGAACTCACTGGAACGG |
| 15 | 12S_P15 | TAATCTTACTAAGAGCTAATAGAAAGGCTAGGACCAAACCTATTTGTTTA |
| 16 | 16S_P1 | AAACCCTGTTCTTGGGTGGGTGTGGGTATAATACTAAGTTGAGATGATAT |
| 17 | 16S_P2 | GCGCTTTGTGAAGTAGGCCTTATTTCTCTTGTCCTTTCGTACAGGGAGGA |
| 18 | 16S_P3 | AAACCGACCTGGATTACTCCGGTCTGAACTCAGATCACGTAGGACTTTAA |
| 19 | 16S_P4 | ACCTTTAATAGCGGCTGCACCATCGGGATGTCCTGATCCAACATCGAGGT |
| 20 | 16S_P5 | TGATATGGACTCTAGAATAGGATTGCGCTGTTATCCCTAGGGTAACTTGT |
| 21 | 16S_P6 | ATTGGATCAATTGAGTATAGTAGTTCGCTTTGACTGGTGAAGTCTTAGCA |
| 22 | 16S_P7 | TTGGGTTCTGCTCCGAGGTCGCCCCAACCGAAATTTTTAATGCAGGTTTG |
| 23 | 16S_P8 | TGGGTTTGTTAGGTACTGTTTGCATTAATAAATTAAAGCTCCATAGGGTC |

TABLE 1-continued

DNA probe sequences for unwanted RNA depletion

| SEQ ID NO | Probe name | Probe sequence 5'-3' |
|---|---|---|
| 24 | 16S_P9 | GTCATGCCCGCCTCTTCACGGGCAGGTCAATTTCACTGGTTAAAAGTAAG |
| 25 | 16S_P10 | CGTGGAGCCATTCATACAGGTCCCTATTTAAGGAACAAGTGATTATGCTA |
| 26 | 16S_P11 | GGTACCGCGGCCGTTAAACATGTGTCACTGGGCAGGCGGTGCCTCTAATA |
| 27 | 16S_P12 | GTGATGTTTTTGGTAAACAGGCGGGGTAAGGTTTGCCGAGTTCCTTTTAC |
| 28 | 16S_P13 | CTTATGAGCATGCCTGTGTTGGGTTGACAGTGAGGGTAATAATGACTTGT |
| 29 | 16S_P14 | ATTGGGCTGTTAATTGTCAGTTCAGTGTTTTGATCTGACGCAGGCTTATG |
| 30 | 16S_P15 | TCATGTTACTTATACTAACATTAGTTCTTCTATAGGGTGATAGATTGGTC |
| 31 | 16S_P16 | AGTTCAGTTATATGTTTGGGATTTTTTAGGTAGTGGGTGTTGAGCTTGAA |
| 32 | 16S_P17 | TGGCTGCTTTTAGGCCTACTATGGGTGTTAAATTTTTTACTCTCTCTACA |
| 33 | 16S_P18 | GTCCAAAGAGCTGTTCCTCTTTGGACTAACAGTTAAATTTACAAGGGGAT |
| 34 | 16S_P19 | GGCAAATTTAAAGTTGAACTAAGATTCTATCTTGGACAACCAGCTATCAC |
| 35 | 16S_P20 | TGTCGCCTCTACCTATAAATCTTCCCACTATTTTGCTACATAGACGGGTG |
| 36 | 16S_P21 | TCTTAGGTAGCTCGTCTGGTTTCGGGGTCTTAGCTTTGGCTCTCCTTGC |
| 37 | 16S_P22 | TAATTCATTATGCAGAAGGTATAGGGGTTAGTCCTTGCTATATTATGCTT |
| 38 | 16S_P23 | TCTTTCCCTTGCGGTACTATATCTATTGCGCCAGGTTTCAATTTCTATCG |
| 39 | 16S_P24 | GGTAAATGGTTTGGCTAAGGTTGTCTGGTAGTAAGGTGGAGTGGGTTTGG |
| 40 | 18S_P1 | TAATGATCCTTCCGCAGGTTCACCTACGGAAACCTTGTTACGACTTTTAC |
| 41 | 18S_P2 | AAGTTCGACCGTCTTCTCAGCGCTCCGCCAGGGCCGTGGGCCGACCCCGG |
| 42 | 18S_P3 | GGCCTCACTAAACCATCCAATCGGTAGTAGCGACGGGCGGTGTGTACAAA |
| 43 | 18S_P4 | CAACGCAAGCTTATGACCCGCACTTACTCGGGAATTCCCTCGTTCATGGG |
| 44 | 18S_P5 | CCGATCCCCATCACGAATGGGGTTCAACGGGTTACCCGCGCCTGCCGGCG |
| 45 | 18S_P6 | CTGAGCCAGTCAGTGTAGCGCGCGTGCAGCCCCGGACATCTAAGGGCATC |
| 46 | 18S_P7 | CTCAATCTCGGGTGGCTGAACGCCACTTGTCCCTCTAAGAAGTTGGGGGA |
| 47 | 18S_P8 | GGTCGCGTAACTAGTTAGCATGCCAGAGTCTCGTTCGTTATCGGAATTAA |
| 48 | 18S_P9 | CACCAACTAAGAACGGCCATGCACCACCACCCACGGAATCGAGAAAGAGC |
| 49 | 18S_P10 | CCTGTCCGTGTCCGGGCCGGGTGAGGTTTCCCGTGTTGAGTCAAATTAAG |
| 50 | 18S_P11 | CTGGTGGTGCCCTTCCGTCAATTCCTTTAAGTTTCAGCTTTGCAACCATA |
| 51 | 18S_P12 | AAAGACTTTGGTTTCCCGGAAGCTGCCCGGCGGGTCATGGGAATAACGCC |
| 52 | 18S_P13 | GGCATCGTTTATGGTCGGAACTACGACGGTATCTGATCGTCTTCGAACCT |
| 53 | 18S_P14 | GATTAATGAAAACATTCTTGGCAAATGCTTTCGCTCTGGTCCGTCTTGCG |
| 54 | 18S_P15 | CACCTCTAGCGGCGCAATACGAATGCCCCGGCCGTCCCTCTTAATCATG |
| 55 | 18S_P16 | ACCAACAAAATAGAACCGCGGTCCTATTCCATTATTCCTAGCTGCGGTAT |
| 56 | 18S_P17 | CTGCTTTGAACACTCTAATTTTTTCAAAGTAAACGCTTCGGGCCCCGCGG |
| 57 | 18S_P18 | GCATCGAGGGGGCGCCGAGAGGCAAGGGGCGGGACGGGCGGTGGCTCGC |
| 58 | 18S_P19 | CCGCCCGCTCCCAAGATCCAACTACGAGCTTTTTAACTGCAGCAACTTTA |
| 59 | 18S_P20 | GCTGGAATTACCGCGGCTGCTGGCACCAGACTTGCCCTCCAATGGATCCT |
| 60 | 18S_P21 | AGTGGACTCATTCCAATTACAGGGCCTCGAAAGAGTCCTGTATTGTTATT |

TABLE 1-continued

DNA probe sequences for unwanted RNA depletion

| SEQ ID NO | Probe name | Probe sequence 5'-3' |
|---|---|---|
| 61 | 18S_P22 | CCCGGGTCGGGAGTGGGTAATTTGCGCGCCTGCTGCCTTCCTTGGATGTG |
| 62 | 18S_P23 | GCTCCCTCTCCGGAATCGAACCCTGATTCCCCGTCACCCGTGGTCACCAT |
| 63 | 18S_P24 | TACCATCGAAAGTTGATAGGGCAGACGTTCGAATGGGTCGTCGCCGCCAC |
| 64 | 18S_P25 | GGCCCGAGGTTATCTAGAGTCACCAAAGCCGCCGGCGCCCGCCCCCCGGC |
| 65 | 18S_P26 | GCTGACCGGGTTGGTTTTGATCTGATAAATGCACGCATCCCCCCCGCGAA |
| 66 | 18S_P27 | TCGGCATGTATTAGCTCTAGAATTACCACAGTTATCCAAGTAGGAGAGGA |
| 67 | 18S_P28 | AACCATAACTGATTTAATGAGCCATTCGCAGTTTCACTGTACCGGCCGTG |
| 68 | 18S_P29 | ATGGCTTAATCTTTGAGACAAGCATATGCTACTGGCAGGATCAACCAGGT |
| 69 | 28S_P1 | GACAAACCCTTGTGTCGAGGGCTGACTTTCAATAGATCGCAGCGAGGGAG |
| 70 | 28S_P2 | CGAAACCCCGACCCAGAAGCAGGTCGTCTACGAATGGTTTAGCGCCAGGT |
| 71 | 28S_P3 | GGTGCGTGACGGGCGAGGGGCGGCCGCCTTTCCGGCCGCGCCCCGTTTC |
| 72 | 28S_P4 | CTCCGCACCGGACCCCGGTCCCGGCGCGCGGCGGGGCACGCGCCCTCCCG |
| 73 | 28S_P5 | AGGGGGGGGCGGCCCGCCGGCGGGGACAGGCGGGGGACCGGCTATCCGAG |
| 74 | 28S_P6 | GCGGCGCTGCCGTATCGTTCGCCTGGGCGGGATTCTGACTTAGAGGCGTT |
| 75 | 28S_P7 | AGATGGTAGCTTCGCCCCATTGGCTCCTCAGCCAAGCACATACACCAAAT |
| 76 | 28S_P8 | TCCTCTCGTACTGAGCAGGATTACCATGGCAACAACACATCATCAGTAGG |
| 77 | 28S_P9 | CTCACGACGGTCTAAACCCAGCTCACGTTCCCTATTAGTGGGTGAACAAT |
| 78 | 28S_P10 | TTCTGCTTCACAATGATAGGAAGAGCCGACATCGAAGGATCAAAAAGCGA |
| 79 | 28S_P11 | TTGGCCGCCACAAGCCAGTTATCCCTGTGGTAACTTTTCTGACACCTCCT |
| 80 | 28S_P12 | GGTCAGAAGGATCGTGAGGCCCCGCTTTCACGGTCTGTATTCGTACTGAA |
| 81 | 28S_P13 | AGCTTTTGCCCTTCTGCTCCACGGGAGGTTTCTGTCCTCCCTGAGCTCGC |
| 82 | 28S_P14 | TTACCGTTTGACAGGTGTACCGCCCCAGTCAAACTCCCCACCTGGCACTG |
| 83 | 28S_P15 | GCGCCCGGCCGGGCGGGCGCTTGGCGCCAGAAGCGAGAGCCCCTCGGGCT |
| 84 | 28S_P16 | CCGGGTCAGTGAAAAAACGATCAGAGTAGTGGTATTTCACCGGCGGCCCG |
| 85 | 28S_P17 | CGCCCCGGGCCCCTCGCGGGACACCGGGGGGGCGCCGGGGGCCTCCCAC |
| 86 | 28S_P18 | CATGTCTCTTCACCGTGCCAGACTAGAGTCAAGCTCAACAGGGTCTTCTT |
| 87 | 28S_P19 | CCAAGCCCGTTCCCTTGGCTGTGGTTTCGCTGGATAGTAGGTAGGGACAG |
| 88 | 28S_P20 | TCCATTCATGCGCGTCACTAATTAGATGACGAGGCATTTGGCTACCTTAA |
| 89 | 28S_P21 | TCCCGCCGTTTACCCGCGCTTCATTGAATTTCTTCACTTTGACATTCAGA |
| 90 | 28S_P22 | CACATCGCGTCAACACCCGCCGCGGGCCTTCGCGATGCTTTGTTTTAATT |
| 91 | 28S_P23 | CCTGGTCCGCACCAGTTCTAAGTCGGCTGCTAGGCGCCGGCCGAGGCGAG |
| 92 | 28S_P24 | CGGCCCCGGGGCGGACCCGGCGGGGGGACCGGCCCGCGGCCCCTCCGC |
| 93 | 28S_P25 | CCGCCGCGCGCCGAGGAGGAGGGGGAACGGGGGCGGACGGGGCCGGGG |
| 94 | 28S_P26 | ACGAACCGCCCCGCCCCGCCGCCCGCCGACCGCCGCCGCCCGACCGCTCC |
| 95 | 28S_P27 | CGCGCGCGACCGAGACGTGGGGTGGGGGTGGGGGGCGCGCCGCGCCGCCG |
| 96 | 28S_P28 | GCGGCCGCGACGCCCGCCGCAGCTGGGGCGATCCACGGGAAGGGCCCGGC |
| 97 | 28S_P29 | GCGCCGCCGCCGGCCCCCCGGGTCCCCGGGGCCCCCCTCGCGGGGACCTG |

TABLE 1-continued

DNA probe sequences for unwanted RNA depletion

| SEQ ID NO | Probe name | Probe sequence 5'-3' |
|---|---|---|
| 98 | 28S_P30 | CCGGCGGCCGCCGCGCGGCCCCTGCCGCCCCGACCCTTCTCCCCCCGCCG |
| 99 | 28S_P31 | CTCCCCCGGGGAGGGGGGAGGACGGGGAGCGGGGGAGAGAGAGAGAGAGA |
| 100 | 28S_P32 | AGGGAGCGAGCGGCGCGCGCGGGTGGGGCGGGGAGGGCCGCGAGGGGGG |
| 101 | 28S_P33 | GGGGGCGCGCGCCTCGTCCAGCCGCGGCGCGCGCCCAGCCCCGCTTCGCG |
| 102 | 28S_P34 | CCCAGCCCTTAGAGCCAATCCTTATCCCGAAGTTACGGATCCGGCTTGCC |
| 103 | 28S_P35 | CATTGTTCCAACATGCCAGAGGCTGTTCACCTTGGAGACCTGCTGCGGAT |
| 104 | 28S_P36 | CGCGAGATTTACACCCTCTCCCCCGGATTTTCAAGGGCCAGCGAGAGCTC |
| 105 | 28S_P37 | AACCGCGACGCTTTCCAAGGCACGGGCCCCTCTCTCGGGGCGAACCCATT |
| 106 | 28S_P38 | CTTCACAAAGAAAAGAGAACTCTCCCCGGGGCTCCCGCCGGCTTCTCCGG |
| 107 | 28S_P39 | CGCACTGGACGCCTCGCGGCGCCCATCTCCGCCACTCCGGATTCGGGGAT |
| 108 | 28S_P40 | TTTCGATCGGCCGAGGGCAACGGAGGCCATCGCCCGTCCCTTCGGAACGG |
| 109 | 28S_P41 | CAGGACCGACTGACCCATGTTCAACTGCTGTTCACATGGAACCCTTCTCC |
| 110 | 28S_P42 | GTTCTCGTTTGAATATTTGCTACTACCACCAAGATCTGCACCTGCGGCGG |
| 111 | 28S_P43 | CGCCCTAGGCTTCAAGGCTCACCGCAGCGGCCCTCCTACTCGTCGCGGCG |
| 112 | 28S_P44 | TCCGGGGCGGGGAGCGGGGCGTGGGCGGGAGGAGGGGAGGAGGCGTGGG |
| 113 | 28S_P45 | AGGACCCCACACCCCCGCCGCCGCCGCCGCCGCCGCCCTCCGACGCACAC |
| 114 | 28S_P46 | GCGCGCCGCCCCGCCGCTCCCGTCCACTCTCGACTGCCGGCGACGGCCG |
| 115 | 28S_P47 | CTCCAGCGCCATCCATTTTCAGGGCTAGTTGATTCGGCAGGTGAGTTGTT |
| 116 | 28S_P48 | GATTCCGACTTCCATGGCCACCGTCCTGCTGTCTATATCAACCAACACCT |
| 117 | 28S_P49 | GAGCGTCGGCATCGGGCGCCTTAACCCGGCGTTCGGTTCATCCCGCAGCG |
| 118 | 28S_P50 | AAAAGTGGCCCACTAGGCACTCGCATTCCACGCCCGGCTCCACGCCAGCG |
| 119 | 28S_P51 | CCATTTAAAGTTTGAGAATAGGTTGAGATCGTTTCGGCCCCAAGACCTCT |
| 120 | 28S_P52 | CGGATAAAACTGCGTGGCGGGGTGCGTCGGGTCTGCGAGAGCGCCAGCT |
| 121 | 28S_P53 | TCGGAGGGAACCAGCTACTAGATGGTTCGATTAGTCTTTCGCCCCTATAC |
| 122 | 28S_P54 | GATTTGCACGTCAGGACCGCTACGGACCTCCACCAGAGTTTCCTCTGGCT |
| 123 | 28S_P55 | ATAGTTCACCATCTTTCGGGTCCTAACACGTGCGCTCGTGCTCCACCTCC |
| 124 | 28S_P56 | AGACGGGCCGGTGGTGCGCCCTCGGCGGACTGGAGAGGCCTCGGGATCCC |
| 125 | 28S_P57 | CGCGCCGGCCTTCACCTTCATTGCGCCACGGCGGCTTTCGTGCGAGCCCC |
| 126 | 28S_P58 | TTAGACTCCTTGGTCCGTGTTTCAAGACGGGTCGGGTGGGTAGCCGACGT |
| 127 | 28S_P59 | GCGCTCGCTCCGCCGTCCCCCTCTTCGGGGACGCGCGCGTGGCCCCGAG |
| 128 | 28S_P60 | CCCGACGGCGCGACCCGCCCGGGGCGCACTGGGGACAGTCCGCCCCGCCC |
| 129 | 28S_P61 | GCACCCCCCCGTCGCCGGGGCGGGGCGCGGGGAGGAGGGGTGGGAGAG |
| 130 | 28S_P62 | AGGGGTGGCCCGGCCCCCCACGAGGAGACGCCGGCGCGCCCCCGCGGGG |
| 131 | 28S_P63 | GGGGATTCCCCGCGGGGTGGGCGCCGGAGGGGGGAGAGCGCGGCGACG |
| 132 | 28S_P64 | GCCCCGGGATTCGGCGAGTGCTGCTGCCGGGGGGCTGTAACACTCGGGG |
| 133 | 28S_P65 | CCGCCCCGCCGCCGCCGCCACCGCCGCCGCCGCCGCCCCGACCCGC |
| 134 | 28S_P66 | AGGACGCGGGGCCGGGGGGCGGAGACGGGGAGGAGGAGGACGGACGGAC |

TABLE 1-continued

DNA probe sequences for unwanted RNA depletion

| SEQ ID NO | Probe name | Probe sequence 5'-3' |
|---|---|---|
| 135 | 28S_P67 | AGCCACCTTCCCCGCCGGGCCTTCCCAGCCGTCCCGGAGCCGGTCGCGGC |
| 136 | 28S_P68 | AAATGCGCCCGGCGGCGCCGGTCGCCGGTCGGGGACGGTCCCCCGCCG |
| 137 | 28S_P69 | CCGCCCGCCCACCCCCGCACCCGCCGGAGCCCGCCCCCTCCGGGGAGGAG |
| 138 | 28S_P70 | GGGAAGGGAGGGCGGGTGGAGGGGTCGGGAGGAACGGGGGGCGGGAAAGA |
| 139 | 28S_P71 | ACACGGCCGGACCCGCCGCCGGGTTGAATCCTCCGGGCGGACTGCGCGGA |
| 140 | 28S_P72 | TCTTAACGGTTTCACGCCCTCTTGAACTCTCTCTTCAAAGTTCTTTTCAA |
| 141 | 28S_P73 | CTTGTTGACTATCGGTCTCGTGCCGGTATTTAGCCTTAGATGGAGTTTAC |
| 142 | 28S_P74 | GCATTCCCAAGCAACCCGACTCCGGGAAGACCCGGGCGCGCGCCGGCCGC |
| 143 | 28S_P75 | GTCCACGGGCTGGGCCTCGATCAGAAGGACTTGGGCCCCCCACGAGCGGC |
| 144 | 28S_P76 | TTCCGTACGCCACATGTCCCGCGCCCCGCGGGGCGGGGATTCGGCGCTGG |
| 145 | 28S_P77 | CTCGCCGTTACTGAGGGAATCCTGGTTAGTTTCTTTTCCTCCGCTGACTA |
| 146 | 28S_P78 | GCGGGTCGCCACGTCTGATCTGAGGTCGCGTCTCGGAGGGGACGGGCCG |
| 147 | 5.8S_P1 | AAGCGACGCTCAGACAGGCGTAGCCCCGGGAGGAACCCGGGGCCGCAAGT |
| 148 | 5.8S_P3 | GCAGCTAGCTGCGTTCTTCATCGACGCACGAGCCGAGTGATCCACCGCTA |
| 149 | 5S_P1 | AAAGCCTACAGCACCCGGTATTCCCAGGCGGTCTCCCATCCAAGTACTAA |
| 150 | 5S_P3 | TTCCGAGATCAGACGAGATCGGGCGCGTTCAGGGTGGTATGGCCGTAGAC |
| 151 | HBA1_P1 | GCCGCCCACTCAGACTTTATTCAAAGACCACGGGGTACGGGTGCAGGAA |
| 152 | HBA1_P2 | GGGGGAGGCCCAAGGGGCAAGAAGCATGGCCACCGAGGCTCCAGCTTAAC |
| 153 | HBA1_P3 | GCACGGTGCTCACAGAAGCCAGGAACTTGTCCAGGGAGGCGTGCACCGCA |
| 154 | HBA1_P4 | GGGAGGTGGGCGGCCAGGGTCACCAGCAGGCAGTGGCTTAGGAGCTTGAA |
| 155 | HBA1_P5 | CCGAAGCTTGTGCGCGTGCAGGTCGCTCAGGGCGGACAGCGCGTTGGGCA |
| 156 | HBA1_P6 | CCACGGCGTTGGTCAGCGCGTCGGCCACCTTCTTGCCGTGGCCCTTAACC |
| 157 | HBA1_P7 | CTCAGGTCGAAGTGCGGGAAGTAGGTCTTGGTGGTGGGGAAGGACAGGAA |
| 158 | HBA1_P8 | CTCCGCACCATACTCGCCAGCGTGCGCGCCGACCTTACCCCAGGCGGCCT |
| 159 | HBA1_P9 | CGGCAGGAGACAGCACCATGGTGGGTTCTCTCTGAGTCTGTGGGGACCAG |
| 160 | HBA2_P1 | GAGGGGAGGAGGGCCCGTTGGGAGGCCCAGCGGGCAGGAGGAACGGCTAC |
| 161 | HBA2_P2 | ACGGTATTTGGAGGTCAGCACGGTGCTCACAGAAGCCAGGAACTTGTCCA |
| 162 | HBA2_P3 | CAGGGGTGAACTCGGCGGGAGGTGGGCGGCCAGGGTCACCAGCAGGCAG |
| 163 | HBA2_P4 | AAGTTGACCGGGTCCACCCGAAGCTTGTGCGCGTGCAGGTCGCTCAGGGC |
| 164 | HBA2_P5 | CATGTCGTCCACGTGCGCCACGGCGTTGGTCAGCGCGTCGGCCACCTTCT |
| 165 | HBA2_P6 | CCTGGGCAGAGCCGTGGCTCAGGTCGAAGTGCGGGAAGTAGGTCTTGGTG |
| 166 | HBA2_P7 | AACATCCTCTCCAGGGCCTCCGCACCATACTCGCCAGCGTGCGCGCCGAC |
| 167 | HBA2_P8 | CTTGACGTTGGTCTTGTCGGCAGGAGACAGCACCATGGTGGGTTCTCTCT |
| 168 | HBB_P1 | GCAATGAAAATAAATGTTTTTTATTAGGCAGAATCCAGATGCTCAAGGCC |
| 169 | HBB_P2 | CAGTTTAGTAGTTGGACTTAGGGAACAAAGGAACCTTTAATAGAAATTGG |
| 170 | HBB_P3 | GCTTAGTGATACTTGTGGGCCAGGGCATTAGCCACACCAGCCACCACTTT |
| 171 | HBB_P4 | CACTGGTGGGGTGAATTCTTTGCCAAAGTGATGGGCCAGCACACAGACCA |

TABLE 1-continued

DNA probe sequences for unwanted RNA depletion

| SEQ ID NO | Probe name | Probe sequence 5'-3' |
|---|---|---|
| 172 | HBB_P5 | GCCTGAAGTTCTCAGGATCCACGTGCAGCTTGTCACAGTGCAGCTCACTC |
| 173 | HBB_P6 | CCCTTGAGGTTGTCCAGGTGAGCCAGGCCATCACTAAAGGCACCGAGCAC |
| 174 | HBB_P7 | CTTCACCTTAGGGTTGCCCATAACAGCATCAGGAGTGGACAGATCCCCAA |
| 175 | HBB_P8 | TCTGGGTCCAAGGGTAGACCACCAGCAGCCTGCCCAGGGCCTCACCACCA |
| 176 | HBB_P9 | ACCTTGCCCCACAGGGCAGTAACGGCAGACTTCTCCTCAGGAGTCAGATG |
| 177 | HBG1_P1 | GTGATCTCTCAGCAGAATAGATTTATTATTTGTATTGCTTGCAGAATAAA |
| 178 | HBG1_P2 | CTCTGAATCATGGGCAGTGAGCTCAGTGGTATCTGGAGGACAGGGCACTG |
| 179 | HBG1_P3 | ATCTTCTGCCAGGAAGCCTGCACCTCAGGGGTGAATTCTTTGCCGAAATG |
| 180 | HBG1_P4 | CACCAGCACATTTCCCAGGAGCTTGAAGTTCTCAGGATCCACATGCAGCT |
| 181 | HBG1_P5 | CACTCAGCTGGGCAAAGGTGCCCTTGAGATCATCCAGGTGCTTTGTGGCA |
| 182 | HBG1_P6 | AGCACCTTCTTGCCATGTGCCTTGACTTTGGGGTTGCCCATGATGGCAGA |
| 183 | HBG1_P7 | GCCAAAGCTGTCAAAGAACCTCTGGGTCCATGGGTAGACAACCAGGAGCC |
| 184 | HBG1_P8 | CTCCAGCATCTTCCACATTCACCTTGCCCCACAGGCTTGTGATAGTAGCC |
| 185 | HBG1_P9 | AAATGACCCATGGCGTCTGGACTAGGAGCTTATTGATAACCTCAGACGTT |
| 186 | HBG2_P1 | GTGATCTCTTAGCAGAATAGATTTATTATTTGATTGCTTGCAGAATAAAG |
| 187 | HBG2_P2 | TCTGCATCATGGGCAGTGAGCTCAGTGGTATCTGGAGGACAGGGCACTGG |
| 188 | HBG2_P3 | TCTTCTGCCAGGAAGCCTGCACCTCAGGGGTGAATTCTTTGCCGAAATGG |
| 189 | HBG2_P4 | ACCAGCACATTTCCCAGGAGCTTGAAGTTCTCAGGATCCACATGCAGCTT |
| 190 | HBG2_P5 | ACTCAGCTGGGCAAAGGTGCCCTTGAGATCATCCAGGTGCTTTATGGCAT |
| 191 | HBG2_P6 | GCACCTTCTTGCCATGTGCCTTGACTTTGGGGTTGCCCATGATGGCAGAG |
| 192 | HBG2_P7 | CCAAAGCTGTCAAAGAACCTCTGGGTCCATGGGTAGACAACCAGGAGCCT |
| 193 | HBG2_P8 | TCCAGCATCTTCCACATTCACCTTGCCCCACAGGCTTGTGATAGTAGCCT |
| 194 | HBG2_P9 | AATGACCCATGGCGTCTGGACTAGGAGCTTATTGATAACCTCAGACGTTC |
| 195 | 5S_GNbac_P1 | ATGCCTGGCAGTTCCCTACTCTCGCATGGGGAGACCCCACACTACCATCG |
| 196 | 5S_GNbac_P2 | ACTTCTGAGTTCGGCATGGGGTCAGGTGGGACCACCGCGCTACGGCCGCC |
| 197 | 16S_GNbac_P1 | GGTTACCTTGTTACGACTTCACCCCAGTCATGAATCACAAAGTGGTAAGT |
| 198 | 16S_GNbac_P2 | AAGCTACCTACTTCTTTTGCAACCCACTCCCATGGTGTGACGGGCGGTGT |
| 199 | 16S_GNbac_P3 | ACGTATTCACCGTGGCATTCTGATCCACGATTACTAGCGATTCCGACTTC |
| 200 | 16S_GNbac_P4 | AGACTCCAATCCGGACTACGACGCACTTTATGAGGTCCGCTTGCTCTCGC |
| 201 | 16S_GNbac_P5 | TGTATGCGCCATTGTAGCACGTGTGTAGCCCTGGTCGTAAGGGCCATGAT |
| 202 | 16S_GNbac_P6 | CCACCTTCCTCCAGTTTATCACTGGCAGTCTCCTTTGAGTTCCCGGCCGG |
| 203 | 16S_GNbac_P7 | GGATAAGGGTTGCGCTCGTTGCGGGACTTAACCCAACATTTCACAACACG |
| 204 | 16S_GNbac_P8 | TGCAGCACCTGTCTCACGGTTCCCGAAGGCACATTCTCATCTCTGAAAAC |
| 205 | 16S_GNbac_P9 | GACCAGGTAAGGTTCTTCGCGTTGCATCGAATTAAACCACATGCTCCACC |
| 206 | 16S_GNbac_P10 | CGTCAATTCATTTGAGTTTTAACCTTGCGGCCGTACTCCCCAGGCGGTCG |
| 207 | 16S_GNbac_P11 | TCCGGAAGCCACGCCTCAAGGGCACAACCTCCAAGTCGACATCGTTTACG |
| 208 | 16S_GNbac_P12 | GTATCTAATCCTGTTTGCTCCCCACGCTTTCGCACTGAGCGTCAGTCTTC |

TABLE 1-continued

DNA probe sequences for unwanted RNA depletion

| SEQ ID NO | Probe name | Probe sequence 5'-3' |
|---|---|---|
| 209 | 16S_GNbac_P13 | TTCGCCACCGGTATTCCTCCAGATCTCTACGCATTTCACCGCTACACCTG |
| 210 | 16S_GNbac_P14 | CTACGAGACTCAAGCTTGCCAGTATCAGATGCAGTTCCCAGGTTGAGCCC |
| 211 | 16S_GNbac_P15 | GACTTAACAAACCGCCTGCGTGCGCTTTACGCCCAGTAATTCCGATTAAC |
| 212 | 16S_GNbac_P16 | ATTACCGCGGCTGCTGGCACGGAGTTAGCCGGTGCTTCTTCTGCGGGTAA |
| 213 | 16S_GNbac_P17 | GTATTAACTTTACTCCCTTCCTCCCCGCTGAAAGTACTTTACAACCCGAA |
| 214 | 16S_GNbac_P18 | CGCGGCATGGCTGCATCAGGCTTGCGCCCATTGTGCAGTATTCCCCACTG |
| 215 | 16S_GNbac_P19 | GTCTGGACCGTGTCTCAGTTCCAGTGTGGCTGGTCATCCTCTCAGACCAG |
| 216 | 16S_GNbac_P20 | TAGGTGAGCCGTTACCCCACCTACTAGCTAATCCCATCTGGGCACATCCG |
| 217 | 16S_GNbac_P21 | AAGGTCCCCCTCTTTGGTCTTGCGACGTTATGCGGTATTAGCTACCGTTT |
| 218 | 16S_GNbac_P22 | CTCCATCAGGCAGTTTCCCAGACATTACTCACCCGTCCGCCACTCGTCAG |
| 219 | 23S_GNbac_P1 | AAGGTTAAGCCTCACGGTTCATTAGTACCGGTTAGCTCAACGCATCGCTG |
| 220 | 23S_GNbac_P2 | CCTATCAACGTCGTCGTCTTCAACGTTCCTTCAGGACCCTTAAAGGGTCA |
| 221 | 23S_GNbac_P3 | GGGGCAAGTTTCGTGCTTAGATGCTTTCAGCACTTATCTCTTCCGCATTT |
| 222 | 23S_GNbac_P4 | CCATTGGCATGACAACCCGAACACCAGTGATGCGTCCACTCCGGTCCTCT |
| 223 | 23S_GNbac_P5 | CCCCCTCAGTTCTCCAGCGCCCACGGCAGATAGGGACCGAACTGTCTCAC |
| 224 | 23S_GNbac_P6 | GCTCGCGTACCACTTTAAATGGCGAACAGCCATACCCTTGGGACCTACTT |
| 225 | 23S_GNbac_P7 | ATGAGCCGACATCGAGGTGCCAAACACCGCCGTCGATATGAACTCTTGGG |
| 226 | 23S_GNbac_P8 | ATCCCCGGAGTACCTTTTATCCGTTGAGCGATGGCCCTTCCATTCAGAAC |
| 227 | 23S_GNbac_P9 | ACCTGCTTTCGCACCTGCTCGCGCCGTCACGCTCGCAGTCAAGCTGGCTT |
| 228 | 23S_GNbac_P10 | CCTCCTGATGTCCGACCAGGATTAGCCAACCTTCGTGCTCCTCCGTTACT |
| 229 | 23S_GNbac_P11 | GCCCCAGTCAAACTACCCACCAGACACTGTCCGCAACCCGGATTACGGGT |
| 230 | 23S_GNbac_P12 | AAACATTAAAGGGTGGTATTTCAAGGTCGGCTCCATGCAGACTGGCGTCC |
| 231 | 23S_GNbac_P13 | CCACCTATCCTACACATCAAGGCTCAATGTTCAGTGTCAAGCTATAGTAA |
| 232 | 23S_GNbac_P14 | TTCCGTCTTGCCGCGGGTACACTGCATCTTCACAGCGAGTTCAATTTCAC |
| 233 | 23S_GNbac_P15 | GACAGCCTGGCCATCATTACGCCATTCGTGCAGGTCGGAACTTACCCGAC |
| 234 | 23S_GNbac_P16 | CTTAGGACCGTTATAGTTACGGCCGCCGTTTACCGGGGCTTCGATCAAGA |
| 235 | 23S_GNbac_P17 | ACCCCATCAATTAACCTTCCGGCACCGGGCAGGCGTCACACCGTATACGT |
| 236 | 23S_GNbac_P18 | CACAGTGCTGTGTTTTTAATAAACAGTTGCAGCCAGCTGGTATCTTCGAC |
| 237 | 23S_GNbac_P19 | CCGCGAGGGACCTCACCTACATATCAGCGTGCCTTCTCCCGAAGTTACGG |
| 238 | 23S_GNbac_P20 | TTCCTTCACCCGAGTTCTCTCAAGCGCCTTGGTATTCTCTACCTGACCAC |
| 239 | 23S_GNbac_P21 | GTACGATTTGATGTTACCTGATGCTTAGAGGCTTTTCCTGGAAGCAGGGC |
| 240 | 23S_GNbac_P22 | ACCGTAGTGCCTCGTCATCACGCCTCAGCCTTGATTTTCCGGATTTGCCT |
| 241 | 23S_GNbac_P23 | ACGCTTAAACCGGGACAACCGTCGCCCGGCCAACATAGCCTTCTCCGTCC |
| 242 | 23S_GNbac_P24 | ACCAAGTACAGGAATATTAACCTGTTTCCCATCGACTACGCCTTTCGGCC |
| 243 | 23S_GNbac_P25 | ACTCACCCTGCCCCGATTAACGTTGGACAGGAACCCTTGGTCTTCCGGCG |
| 244 | 23S_GNbac_P26 | CGCTTTATCGTTACTTATGTCAGCATTCGCACTTCTGATACCTCCAGCAT |
| 245 | 23S_GNbac_P27 | TTCGCAGGCTTACAGAACGCTCCCCTACCCAACAACGCATAAGCGTCGCT |

TABLE 1-continued

DNA probe sequences for unwanted RNA depletion

| SEQ ID NO | Probe name | Probe sequence 5'-3' |
|---|---|---|
| 246 | 23S_GNbac_P28 | CATGGTTTAGCCCCGTTACATCTTCCGCGCAGGCCGACTCGACCAGTGAG |
| 247 | 23S_GNbac_P29 | TAAATGATGGCTGCTTCTAAGCCAACATCCTGGCTGTCTGGGCCTTCCCA |
| 248 | 23S_GNbac_P30 | AACCATGACTTTGGGACCTTAGCTGGCGGTCTGGGTTGTTTCCCTCTTCA |
| 249 | 23S_GNbac_P31 | CCCGCCGTGTGTCTCCCGTGATAACATTCTCCGGTATTCGCAGTTTGCAT |
| 250 | 23S_GNbac_P32 | GGATGACCCCCTTGCCGAAACAGTGCTCTACCCCCGGAGATGAATTCACG |
| 251 | 23S_GNbac_P33 | AGCTTTCGGGGAGAACCAGCTATCTCCCGGTTTGATTGGCCTTTCACCCC |
| 252 | 23S_GNbac_P34 | CGCTAATTTTTCAACATTAGTCGGTTCGGTCCTCCAGTTAGTGTTACCCA |
| 253 | 23S_GNbac_P35 | ATGGCTAGATCACCGGGTTTCGGGTCTATACCCTGCAACTTAACGCCCAG |
| 254 | 23S_GNbac_P36 | CCTTCGGCTCCCTATTCGGTTAACCTTGCTACAGAATATAAGTCGCTGA |
| 255 | 23S_GNbac_P37 | GTACGCAGTCACACGCCTAAGCGTGCTCCCACTGCTTGTACGTACACGGT |
| 256 | 23S_GNbac_P38 | ACTCCCCTCGCCGGGGTTCTTTTCGCCTTTCCCTCACGGTACTGGTTCAC |
| 257 | 23S_GNbac_P39 | AGTATTTAGCCTTGGAGGATGGTCCCCCCATATTCAGACAGGATACCACG |
| 258 | 23S_GNbac_P40 | ATCGAGCTCACAGCATGTGCATTTTTGTGTACGGGGCTGTCACCCTGTAT |
| 259 | 23S_GNbac_P41 | ACGCTTCCACTAACACACACTGATTCAGGCTCTGGGCTGCTCCCCGTT |
| 260 | 23S_GNbac_P42 | GGGGAATCTCGGTTGATTTCTTTTCCTCGGGGTACTTAGATGTTTCAGTT |
| 261 | 23S_GNbac_P43 | ATTAACCTATGGATTCAGTTAATGATAGTGTGTCGAAACACACTGGGTTT |
| 262 | 23S_GNbac_P44 | GCCGGTTATAACGGTTCATATCACCTTACCGACGCTTATCGCAGATTAGC |
| 263 | 5S_GPbac_P1 | GCTTGGCGGCGTCCTACTCTCACAGGGGGAAACCCCCGACTACCATCGGC |
| 264 | 5S_GPbac_P2 | TTCCGTGTTCGGTATGGGAACGGGTGTGACCTCTTCGCTATCGCCACCAA |
| 265 | 16S_GPbac_P1 | TAGAAAGGAGGTGATCCAGCCGCACCTTCCGATACGGCTACCTTGTTACG |
| 266 | 16S_GPbac_P2 | TCTGTCCCACCTTCGGCGGCTGGCTCCTAAAAGGTTACCTCACCGACTTC |
| 267 | 16S_GPbac_P3 | TCGTGGTGTGACGGGCGGTGTGTACAAGGCCCGGGAACGTATTCACCGCG |
| 268 | 16S_GPbac_P4 | ATTACTAGCGATTCCAGCTTCACGCAGTCGAGTTGCAGACTGCGATCCGA |
| 269 | 16S_GPbac_P5 | GTGGGATTGGCTTAACCTCGCGGTTTCGCTGCCCTTTGTTCTGTCCATTG |
| 270 | 16S_GPbac_P6 | CCAGGTCATAAGGGGCATGATGATTTGACGTCATCCCCACCTTCCTCCGG |
| 271 | 16S_GPbac_P7 | CACCTTAGAGTGCCCAACTGAATGCTGGCAACTAAGATCAAGGGTTGCGC |
| 272 | 16S_GPbac_P8 | ACCCAACATCTCACGACACGAGCTGACGACAACCATGCACCACCTGTCAC |
| 273 | 16S_GPbac_P9 | GACGTCCTATCTCTAGGATTGTCAGAGGATGTCAAGACCTGGTAAGGTTC |
| 274 | 16S_GPbac_P10 | ATTAAACCACATGCTCCACCGCTTGTGCGGGCCCCCGTCAATTCCTTTGA |
| 275 | 16S_GPbac_P11 | CCGTACTCCCCAGGCGGAGTGCTTAATGCGTTAGCTGCAGCACTAAGGGG |
| 276 | 16S_GPbac_P12 | ACTTAGCACTCATCGTTTACGGCGTGGACTACCAGGGTATCTAATCCTGT |
| 277 | 16S_GPbac_P13 | TCGCTCCTCAGCGTCAGTTACAGACCAGAGAGTCGCCTTCGCCACTGGTG |
| 278 | 16S_GPbac_P14 | ACGCATTTCACCGCTACACGTGGAATTCCACTCTCCTCTTCTGCACTCAA |
| 279 | 16S_GPbac_P15 | ATGACCCTCCCCGGTTGAGCCGGGGCTTTCACATCAGACTTAAGAAACC |
| 280 | 16S_GPbac_P16 | ACGCCCAATAATTCCGGACAACGCTTGCCACCTACGTATTACCGCGGCTG |
| 281 | 16S_GPbac_P17 | CCGTGGCTTTCTGGTTAGGTACCGTCAAGGTACCGCCCTATTCGAACGGT |
| 282 | 16S_GPbac_P18 | ACAACAGAGCTTTACGATCCGAAAACCTTCATCACTCACGCGGCGTTGCT |

TABLE 1-continued

DNA probe sequences for unwanted RNA depletion

| SEQ ID NO | Probe name | Probe sequence 5'-3' |
|---|---|---|
| 283 | 16S_GPbac_P19 | CCATTGCGGAAGATTCCCTACTGCTGCCTCCCGTAGGAGTCTGGGCCGTG |
| 284 | 16S_GPbac_P20 | GGCCGATCACCCTCTCAGGTCGGCTACGCATCGTCGCCTTGGTGAGCCGT |
| 285 | 16S_GPbac_P21 | CTAATGCGCCGCGGGTCCATCTGTAAGTGGTAGCCGAAGCCACCTTTTAT |
| 286 | 16S_GPbac_P22 | TTCAAACAACCATCCGGTATTAGCCCCGGTTTCCCGGAGTTATCCCAGTC |
| 287 | 16S_GPbac_P23 | CCACGTGTTACTCACCCGTCCGCCGCTAACATCAGGGAGCAAGCTCCCAT |
| 288 | 16S_GPbac_P24 | GCATGTATTAGGCACGCCGCCAGCGTTCGTCCTGAGCCAGGATCAAACTC |
| 289 | 23S_GPbac_P1 | TGGTTAAGTCCTCGATCGATTAGTATCTGTCAGCTCCATGTGTCGCCACA |
| 290 | 23S_GPbac_P2 | TATCAACCTGATCATCTTTCAGGGATCTTACTTCCTTGCGGAATGGGAAA |
| 291 | 23S_GPbac_P3 | GGCTTCATGCTTAGATGCTTTCAGCACTTATCCCGTCCGCACATAGCTAC |
| 292 | 23S_GPbac_P4 | GCAGAACAACTGGTACACCAGCGGTGCGTCCATCCCGGTCCTCTCGTACT |
| 293 | 23S_GPbac_P5 | CAAATTTCCTGCGCCCGCGACGGATAGGGACCGAACTGTCTCACGACGTT |
| 294 | 23S_GPbac_P6 | GTACCGCTTTAATGGGCGAACAGCCCAACCCTTGGGACTGACTACAGCCC |
| 295 | 23S_GPbac_P7 | CGACATCGAGGTGCCAAACCTCCCCGTCGATGTGGACTCTTGGGGGAGAT |
| 296 | 23S_GPbac_P8 | GGGGTAGCTTTTATCCGTTGAGCGATGGCCCTTCCATGCGGAACCACCGG |
| 297 | 23S_GPbac_P9 | TTTCGTCCCTGCTCGACTTGTAGGTCTCGCAGTCAAGCTCCCTTGTGCCT |
| 298 | 23S_GPbac_P10 | GATTTCCAACCATTCTGAGGGAACCTTTGGGCGCCTCCGTTACCTTTTAG |
| 299 | 23S_GPbac_P11 | GTCAAACTGCCCACCTGACACTGTCTCCCCGCCCGATAAGGGCGGCGGGT |
| 300 | 23S_GPbac_P12 | GCCAGGGTAGTATCCCACCGATGCCTCCACCGAAGCTGGCGCTCCGGTTT |
| 301 | 23S_GPbac_P13 | ATCCTGTACAAGCTGTACCAACATTCAATATCAGGCTGCAGTAAAGCTCC |
| 302 | 23S_GPbac_P14 | CCTGTCGCGGGTAACCTGCATCTTCACAGGTACTATAATTTCACCGAGTC |
| 303 | 23S_GPbac_P15 | GCCCAGATCGTTGCGCCTTTCGTGCGGGTCGGAACTTACCCGACAAGGAA |
| 304 | 23S_GPbac_P16 | ACCGTTATAGTTACGGCCGCCGTTTACTGGGGCTTCAATTCGCACCTTCG |
| 305 | 23S_GPbac_P17 | CCTCTTAACCTTCCAGCACCGGGCAGGCGTCAGCCCCTATACTTCGCCTT |
| 306 | 23S_GPbac_P18 | CCTGTGTTTTTGCTAAACAGTCGCCTGGGCCTATTCACTGCGGCTCTCTC |
| 307 | 23S_GPbac_P19 | CAGAGCACCCCTTCTCCCGAAGTTACGGGGTCATTTTGCCGAGTTCCTTA |
| 308 | 23S_GPbac_P20 | ATCACCTTAGGATTCTCTCCTCGCCTACCTGTGTCGGTTTGCGGTACGGG |
| 309 | 23S_GPbac_P21 | TAGAGGCTTTTCTTGGCAGTGTGGAATCAGGAACTTCGCTACTATATTTC |
| 310 | 23S_GPbac_P22 | TCAGCCTTATGGGAAACGGATTTGCCTATTTCCCAGCCTAACTGCTTGGA |
| 311 | 23S_GPbac_P23 | CCGCGCTTACCCTATCCTCCTGCGTCCCCCATTGCTCAAATGGTGAGGA |
| 312 | 23S_GPbac_P24 | TCAACCTGTTGTCCATCGCCTACGCCTTTCGGCCTCGGCTTAGGTCCCGA |
| 313 | 23S_GPbac_P25 | CGAGCCTTCCTCAGGAAACCTTAGGCATTCGGTGGAGGGGATTCTCACCC |
| 314 | 23S_GPbac_P26 | TACCGGCATTCTCACTTCTAAGCGCTCCACCAGTCCTTCCGGTCTGGCTT |
| 315 | 23S_GPbac_P27 | GCTCTCCTACCACTGTTCGAAGAACAGTCCGCAGCTTCGGTGATACGTTT |
| 316 | 23S_GPbac_P28 | TCGGCGCAGAGTCACTCGACCAGTGAGCTATTACGCACTCTTTAAATGGT |
| 317 | 23S_GPbac_P29 | AACATCCTGGTTGTCTAAGCAACTCCACATCCTTTTCCACTTAACGTATA |
| 318 | 23S_GPbac_P30 | TGGCGGTCTGGGCTGTTTCCCTTTCGACTACGGATCTTATCACTCGCAGT |
| 319 | 23S_GPbac_P31 | AAGTCATTGGCATTCGGAGTTTGACTGAATTCGGTAACCCGGTAGGGGCC |

TABLE 1-continued

DNA probe sequences for unwanted RNA depletion

| SEQ ID NO | Probe name | Probe sequence 5'-3' |
|---|---|---|
| 320 | 23S_GPbac_P32 | GCTCTACCTCCAAGACTCTTACCTTGAGGCTAGCCCTAAAGCTATTTCGG |
| 321 | 23S_GPbac_P33 | TCCAGGTTCGATTGGCATTTCACCCCTACCCACACCTCATCCCCGCACTT |
| 322 | 23S_GPbac_P34 | TTCGGGCCTCCATTCAGTGTTACCTGAACTTCACCCTGGACATGGGTAGA |
| 323 | 23S_GPbac_P35 | TCTACGACCACGTACTCATGCGCCCTATTCAGACTCGCTTTCGCTGCGGC |
| 324 | 23S_GPbac_P36 | TAACCTTGCACGGGATCGTAACTCGCCGGTTCATTCTACAAAAGGCACGC |
| 325 | 23S_GPbac_P37 | GGCTCTGACTACTTGTAGGCACACGGTTTCAGGATCTCTTTCACTCCCCT |
| 326 | 23S_GPbac_P38 | ACCTTTCCCTCACGGTACTGGTTCACTATCGGTCACTAGGGAGTATTTAG |
| 327 | 23S_GPbac_P39 | CTCCCGGATTCCGACGGAATTTCACGTGTTCCGCCGTACTCAGGATCCAC |
| 328 | 23S_GPbac_P40 | GTTTTGACTACAGGGCTGTTACCTCCTATGGCGGGCCTTTCCAGACCTCT |
| 329 | 23S_GPbac_P41 | CTTTGTAACTCCGTACAGAGTGTCCTACAACCCCAAGAGGCAAGCCTCTT |
| 330 | 23S_GPbac_P42 | CGTTTCGCTCGCCGCTACTCAGGGAATCGCATTTGCTTTCTCTTCCTCCG |
| 331 | 23S_GPbac_P43 | CAGTTCCCCGGGTCTGCCTTCTCATATCCTATGAATTCAGATATGGATAC |
| 332 | 23S_GPbac_P44 | GGTGGGTTTCCCCATTCGGAAATCTCCGGATCAAAGCTTGCTTACAGCTC |
| 333 | 23S_GPbac_P45 | TGTTCGTCCCGTCCTTCATCGGCTCCTAGTGCCAAGGCATCCACCGTGCG |
| 334 | 16S:A1 | AAACTAGATTCGAATATAACAAAACATTACATCCTCATCCAATCCCTTTT |
| 335 | 16S:A2 | GCGGTGTGTGCAAGGAGCAGGGACGTATTCACCGCGCGATTGTGACACGC |
| 336 | 16S:A3 | GCCTTTCGGCGTCGGAACCCATTGTCTCAGCCATTGTAGCCCGCGTGTTG |
| 337 | 16S:A4 | GCATACGGACCTACCGTCGTCCACTCCTTCCTCCTATTTATCATAGGCGG |
| 338 | 16S:A5 | CGGCATCCAAAAAAGGATCCGCTGGTAACTAAGAGCGTGGGTCTCGCTCG |
| 339 | 16S:A6 | CAACCTGGCTATCATACAGCTGTCGCCTCTGGTGAGATGTCCGGCGTTGA |
| 340 | 16S:A7 | AGGCTCCACGCGTTGTGGTGCTCCCCCGCCAATTCCTTTAAGTTTCAGTC |
| 341 | 16S:A8 | CCAGGCGGCGGACTTAACAGCTTCCCTTCGGCACTGGGACAGCTCAAAGC |
| 342 | 16S:A9 | TCCGCATCGTTTACAGCTAGGACTACCCGGGTATCTAATCCGGTTCGCGC |
| 343 | 16S:A10 | TTCCCACAGTTAAGCTGCAGGATTTCACCAGAGACTTATTAAACCGGCTA |
| 344 | 16S:A12 | CTCTTATTCCAAAAGCTCTTTACACTAATGAAAAGCCATCCCGTTAAGAA |
| 345 | 16S:A13 | CCCCCGTCGCGATTTCTCACATTGCGGAGGTTTCGCGCCTGCTGCACCCC |
| 346 | 16S:A14 | TTGTCTCAGGTTCCATCTCCGGGCTCTTGCTCTCACAACCCGTACCGATC |
| 347 | 16S:A16 | CATTACCTAACCAACTACCTAATCGGCCGCAGACCCATCCTTAGGCGAAA |
| 348 | 16S:A17 | AAACCATTACAGGAATAATTGCCTATCCAGTATTATCCCCAGTTTCCCAG |
| 349 | 16S:A18 | AAGGGTAGGTTATCCACGTGTTACTGAGCCGTACGCCACGAGCCTAAACT |
| 350 | 23S:A1 | ACCTAGCGCGTAGCTGCCCGGCACTGCCTTATCAGACAACGGTCGACCA |
| 351 | 23S:A2 | CGTTCCTCTCGTACTGGAGCCACCTTCCCCTCAGACTACTAACACATCCA |
| 352 | 23S:A3 | CCTGTCTCACGACGGTCTAAACCCAGCTCACGTTCCCCTTTAATGGGCGA |
| 353 | 23S:A4 | GGTGCTGCTGCACACCCAGGATGGAAAGAACCGACATCGAAGTAGCAAGC |
| 354 | 23S:A5 | GGCTCTTGCCTGCGACCACCCAGTTATCCCCGAGGTAGTTTTTCTGTCAT |
| 355 | 23S:A6 | AGGAGGACTCTGAGGTTCGCTAGGCCCGGCTTTCGCCTCTGGATTTCTTG |
| 356 | 23S:A7 | CAAAGTAAGTTAGAAACACAGTCATAAGAAAGTGGTGTCTCAAGAACGAA |

TABLE 1-continued

DNA probe sequences for unwanted RNA depletion

| SEQ ID NO | Probe name | Probe sequence 5'-3' |
|---|---|---|
| 357 | 23S:A8 | GACTTATAATCGAATTCTCCCACTTACACTGCATACCTATAACCAAGCTT |
| 358 | 23S:A9 | GTAAAACTCTACGGGTCTTCGCTTCCCAATGGAAGACTCTGGCTTGTGC |
| 359 | 23S:A10 | TCACTAAGTTCTAGCTAGGGACAGTGGGGACCTCGTTCTACCATTCATGC |
| 360 | 23S:A11 | CGACAAGGCATTTCGCTACCTTAAGAGGGTTATAGTTACCCCCGCCGTTT |
| 361 | 23S:A12 | AACTGAACTCCAGCTTCACGTGCCAGCACTGGGCAGGTGTCGCCCTCTGT |
| 362 | 23S:A13 | CTAGCAGAGAGCTATGTTTTTATTAAACAGTCGGGCCCCCCTAGTCACTG |
| 363 | 23S:A14 | TTAAAACGCCTTAGCCTACTCAGCTAGGGGCACCTGTGACGGATCTCGGT |
| 364 | 23S:A15 | ACAAAACTAACTCCCTTTTCAAGGACTCCATGAATCAGTTAAACCAGTAC |
| 365 | 23S:A16 | ATAATGCCTACACCTGGTTCTCGCTATTACACCTCTCCCCAGGCTTAAAC |
| 366 | 23S:A17 | CAATCCTACAAAACATATCTCGAAGTGTCAGAAATTAGCCCTCAACGTCA |
| 367 | 23S:A18 | CTTTGCTGCTACTACTACCAGGATCCACATACCTGCAAGGTCCAAAGGAA |
| 368 | 23S:A19 | CAACCCACACAGGTCGCCACTCTACACAATCACCAAAAAAAAGGTGTTCC |
| 369 | 23S:A20 | GGATTAATTCCCGTCCATTTTAGGTGCCTCTGACCTCGATGGGTGATCTG |
| 370 | 23S:A21 | AGGGTGGCTGCTTCTAAGCCCACCTTCCCATTGTCTTGGGCCAAAGACTC |
| 371 | 23S:A22 | GTATTTAGGGGCCTTAACCATAGTCTGAGTTGTTTCTCTTTCGGGACACA |
| 372 | 23S:A23 | CCTCACTCCAACCTTCTACGACGGTGACGAGTTCGGAGTTTTACAGTACG |
| 373 | 23S:A24 | CCCTAAACGTCCAATTAGTGCTCTACCCCGCCACCAACCTCCAGTCAGGC |
| 374 | 23S:A25 | AATAGATCGACCGGCTTCGGGTTTCAATGCTGTGATTCCAGGCCCTATTA |
| 375 | 23S:A26 | ACAACGCTGCGGGCATATCGGTTTCCCTACGACTACAAGGATAAAAACCT |
| 376 | 23S:A27 | ACAAAGAACTCCCTGGCCCGTGTTTCAAGACGGACGATGCAACACTAGTC |
| 377 | 23S:A28 | ACAATGTTACCACTGATTCTTTCGGAAGAATTCATTCCTTACGCGCCACA |
| 378 | 23S:A29 | CTGGTTTCAGGTACTTTTCACCCCCCTATAGGGGTACTTTTCAGCATTCC |
| 379 | 23S:A30 | CTCTATCGGTCTTGAGACGTATTTAGAATTGGAAGTTGATGCCTCCCACA |
| 380 | 23S:A31 | ATCACCCTCTACGGTTCTAAAATTCCAAATAAAATTCGATTTATCCCACG |
| 381 | 23S:A32 | TCTATACACCACATCTCCCTAATATTACTAAAAGGGATTCAGTTTGTTCT |
| 382 | 23S:A33 | GCCGTTACTAACGACATCGCATATTGCTTTCTTTTCCTCCGCCTACTAAG |
| 383 | 23S:A34 | GGGTTCCCAATCCTACACGGATCAACACAAAAAAAATGTGCTAGGAAGTC |
| 384 | 5S:A1 | ACTACTGGGATCGAAACGAGACCAGGTATAACCCCCATGCTATGACCGCA |
| 385 | MM_16S_P10 | GCGTATGCCTGGAGAATTGGAATTCTTGTTACTCATACTAACAGTGTTGC |
| 386 | MM_16S_P11 | GATTAACCCAATTTTAAGTTTAGGAAGTTGGTGTAAATTATGGAATTAAT |
| 387 | MM_16S_P12 | AGCTTGAACGCTTTCTTTATTGGTGGCTGCTTTTAGGCCTACAATGGTTA |
| 388 | MM_16S_P13 | ATTATTCACTATTAAAGGTTTTTTCCGTTCCAGAAGAGCTGTCCCTCTTT |
| 389 | MM_16S_P14 | CTTACTTTTTGATTTTGTTGTTTTTTAGCAAGTTTAAAATTGAACTTAA |
| 390 | MM_16S_P15 | AACCAGCTATCACCAAGCTCGTTAGGCTTTTCACCTCTACCTAAAAATCT |
| 391 | MM_16S_P7 | AATACTTGTAATGCTAGAGGTGATGTTTTTGGTAAACAGGCGGGGTTCTT |
| 392 | MM_16S_P8 | TTTATCTTTTTGGATCTTTCCTTTAGGCATTCCGGTGTTGGGTTAACAGA |
| 393 | MM_16S_P9 | TTATTTATAGTGTGATTATTGCCTATAGTCTGATTAACTAACAATGGTTA |

TABLE 1-continued

DNA probe sequences for unwanted RNA depletion

| SEQ ID NO | Probe name | Probe sequence 5'-3' |
|---|---|---|
| 394 | RN_16S_P4 | AGTGATTGTAGTTGTTTATTCACTATTTAAGGTTTTTTCCTTTTCCTAAA |
| 395 | RN_16S_P5 | TGGCTATATTTTAAGTTTACATTTTGATTTGTTGTTCTGATGGTAAGCTT |
| 396 | RN_16S_P6 | TTTTTTTAATCTTTCCTTAAAGCACGCCTGTGTTGGGCTAACGAGTTAGG |
| 397 | RN_16S_P7 | TGTTGGGTTAGTACCTATGATTCGATAATTGACAATGGTTATCCGGGTTG |
| 398 | RN_16S_P8 | AGGAGAATTGGTTCTTGTTACTCATATTAACAGTATTTCATCTATGGATC |
| 399 | RN_16S_P9 | TTTGTGATATAGGAATTTATTGAGGTTTGTGGAATTAGTGTGTGTAAGTA |
| 400 | MM_28S_P1 | GCCGGGGAGTGGGTCTTCCGTACGCCACATTTCCCACGCCGCGACGCGCG |
| 401 | MM_28S_P10 | ACCTCGGGCCCCCGGGCGGGGCCCTTCACCTTCATTGCGCCACGGCGGCT |
| 402 | MM_28S_P14 | TCGCGTCCAGAGTCGCCGCCGCCGCCGGCCCCCCGAGTGTCCGGGCCCCC |
| 403 | MM_28S_P15 | CGCTGGTTCCTCCCGCTCCGGAACCCCGCGGGGTTGGACCCGCCGCCCC |
| 404 | MM_28S_P16 | CGCCGACCCCCGACCCGCCCCCCGACGGGAAGAAGGAGGGGGGAAGAGAG |
| 405 | MM_28S_P17 | GGGACGACGGGGCCCCGCGGGGAAGAGGGGAGGGCGGGCCCGGGCGGAAA |
| 406 | MM_28S_P18 | GGCGCCGCGCGGAAAACCGCGGCCCGGGGGGCGGACCCGGCGGGGGAACA |
| 407 | MM_28S_P19 | CCCCCACACGCGCGGGACACGCCCGCCCGCCCCCGCCACGCACCTCGGGA |
| 408 | MM_28S_P2 | CACCCGCTTTGGGCTGCATTCCCAAGCAACCCGACTCCGGGAAGACCCGA |
| 409 | MM_28S_P20 | TGGAGCGAGGCCCCGCGGGGAGGGGACCCGCGCCGGCACCCGCCGGGCTC |
| 410 | MM_28S_P21 | CGAGGCCGGCGTGCCCCGACCCCGACGCGAGGACGGGGCCGGGCGCCGGG |
| 411 | MM_28S_P22 | TCCCCGGAGCGGGTCGCGCCCGCCCGCACGCGCGGGACGGACGCTTGGCG |
| 412 | MM_28S_P23 | TCCACACGAACGTGCGTTCAACGTGACGGGCGAGAGGGCGGCCCCCTTTC |
| 413 | MM_28S_P24 | TCCCAAGACGAACGGCTCTCCGCACCGGACCCCGGTCCCGACGCCCGGCG |
| 414 | MM_28S_P25 | CCGCCGCGGGGACGACGCGGGGACCCCGCCGAGCGGGGACGGACGGGGAC |
| 415 | MM_28S_P3 | GCACCGCCACGGTGGAAGTGCGCCCGGCGGCGGCCGGTCGCCGGCCGGGG |
| 416 | MM_28S_P6 | CCCACCGGGCCCCGAGAGAGGCGACGGAGGGGGTGGGAGAGCGGTCGCG |
| 417 | MM_28S_P7 | CCCGGCCCCCACCCCACGCCCGCCCGGGAGGCGGACGGGGGGAGAGGGA |
| 418 | MM_28S_P8 | TATCTGGCTTCCTCGGCCCCGGGATTCGGCGAAAGCGCGGCCGGAGGGCT |
| 419 | MM_28S_P9 | CGCCGCCGACCCCGTGCGCTCGGCTTCGTCGGGAGACGCGTGACCGACGG |
| 420 | RN_28S_P12 | GCGCCCCCCGCACCCGCCCCGTCCCCCCCGCGGACGGGGAAGAAGGGAG |
| 421 | RN_28S_P14 | CGAACCCCGGGAACCCCCGACCCCGCGGAGGGGAAGGGGAGGACGAGG |
| 422 | RN_28S_P16 | CACCCGGGGGGCGACGAGGCGGGGACCCGCCGGACGGGGACGGACGGGG |
| 423 | RN_28S_P17 | GCCAACCGAGGCTCCTTCGGCGCTGCCGTATCGTTCCGCTTGGGCGGATT |
| 424 | RN_28S_P4 | CCCGGGCCCCCGGACCCCCGAGAGGGACGACGGAGGCGACGGGGGGTGGG |
| 425 | RN_28S_P5 | TGGGAGGGGCGGCCCGGCCCCCGCGACCGCCCCCCTTTCCGCCACCCCAC |
| 426 | RN_28S_P6 | GGGAGAGGCCGGGGGAGAGCGCGGCGACGGGTATCCGGCTCCCTCGGCC |
| 427 | RN_28S_P7 | CGCTGCTGCCGGGGGGCTGTAACACTCGGGGCGGGGTGGTCCGGCGCCCA |
| 428 | RN_28S_P8 | CGCCGCCGACCCCGTGCGCTCGGCTTCGCTCCCCCCCACCCCGAGAAGGG |

In one embodiment, the RNA sample is from a human and the DNA probe set includes probes specific to human unwanted RNA species such as rRNA and mitochondrial mRNA transcripts as described in this disclosure. In another embodiment, a DNA probe set for depleting unwanted RNA from a human RNA sample includes probes specific to human rRNA and mitochondrial mRNA transcripts, and probes specific to Gram positive and Gram negative unwanted RNA transcripts as described in this disclosure. In a further embodiment, a DNA probe set for depleting unwanted RNA from a human RNA sample includes probes specific to an Archaea bacterial species, an example of which is *M. smithii* as described in this disclosure. As such, in some embodiments, a DNA probe set for depleting rRNA from a human RNA sample comprises only probes directed to human unwanted RNA species or comprises a mixed DNA probe set that targets non-human unwanted RNA transcripts as well. A skilled artisan will understand that the probe set to be used for RNA depletion will depend on the research intentions for the sample, the environment from which the sample was taken, and any other factors that lead into an experimental design for RNA depletion of an RNA sample.

In one embodiment, the RNA sample is from a non-human eukaryote and the DNA probe set includes probes specific to unwanted RNA in that eukaryotic sourced sample. For example, if the RNA sample is from a mouse or rat, the DNA probe set would include probes specific to mouse or rat unwanted RNA species, which may also include DNA probes specific to unwanted Gram positive and Gram negative bacterial RNA species as well, or other bacterial species such as Archaea species.

In some embodiments, the DNA probes do not hybridize to the entire contiguous length of an RNA species to be deleted. Surprisingly, it was found during experimentation that the full length sequence of a RNA species targeted for depletion need not be targeted with a full-length DNA probe, or a probe set that tiles contiguously over the entire RNA sequence; indeed the DNA probes described herein leave gaps such that the DNA:RNA hybrids formed are not contiguous. Surprisingly, gaps of at least 5 nt, 10 nt, 15 nt or 20 nt between DNA:RNA hybrids provided efficient RNA depletion. Further, probe sets that include gaps can hybridize more efficiently to the unwanted RNA, as the DNA probes do not hinder hybridization of adjacent probes as could potentially occur with probes that cover the whole RNA sequence targeted for depletion, or probes that overlap one another.

In addition, probe sets can be supplemented to improve RNA depletion methods for a given species. A method of supplementing a probe set for use in depleting off-target RNA nucleic acid molecules from a nucleic acid sample can comprise: a) contacting a nucleic acid sample comprising at least one RNA or DNA target sequence and at least one off-target RNA molecule from a first species with a probe set comprising at least two DNA probes complementary to discontiguous sequences along the full length of the at least one off-target RNA molecule from a second species, thereby hybridizing the DNA probes to the off-target RNA molecules to form DNA:RNA hybrids, wherein each DNA:RNA hybrid is at least 5 bases apart, or at least 10 bases apart, along a given off-target RNA molecule sequence from any other DNA:RNA hybrid; b) contacting the DNA:RNA hybrids with a ribonuclease that degrades the RNA from the DNA:RNA hybrids, thereby degrading the off-target RNA molecules in the nucleic acid sample to form a degraded mixture; c) separating the degraded RNA from the sample; d) sequencing the remaining RNA from the sample; e) evaluating the remaining RNA sequences for the presence of off-target RNA molecules from the first species, thereby determining gap sequence regions; and f) supplementing the probe set with at least one DNA probe complementary to discontiguous sequences in one or more of the gap sequence regions. In some embodiments, the gap sequence regions comprise at least 50, or at least 60, or at least 70 base pairs. In some embodiments, the first species is a non-human species and the second species is human. In some embodiments, the first species is rat or mouse. Exemplary methods for supplementing a probe set for improved depletion of off-target rRNA nucleic acid molecules in mouse samples are outlined in Example 8 and FIG. 9.

In some embodiments, a first species is a non-human species and a second species is human. In some embodiments, a first species is rat or mouse. In some embodiments, the second species is human, Gram-positive bacteria, Gram-negative bacteria, or a mixture thereof.

Compositions and Kits

In one embodiment, the present disclosure relates to compositions comprising a probe set as described herein. In some embodiments, the composition comprises the probe set and a ribonuclease capable of degrading RNA in a DNA:RNA hybrid, such as RNase H or Hybridase. In some embodiments, the probe set comprises at least two DNA probes complementary to at least one off-target rRNA molecule in the nucleic acid sample, wherein the probes are non-overlapping and are discontiguous relative to the length of the off-target rRNA molecule (e.g., at least 5 or at least 10 bases apart along the full length). In some embodiments, the composition comprises the probe set comprising at least two DNA probes hybridized to at least one off-target RNA molecule, wherein each DNA probe is hybridized at least 5, or at least 10, bases apart along the length of the off-target RNA molecule from any other DNA probe in the probe set. In some embodiments, the composition comprises a nucleic acid destabilizing chemical such as formamide, betaine, DMSO, glycerol, or derivatives or mixtures thereof. In one embodiment, the destabilizing chemical is formamide or a derivative thereof which is present in a concentration of between 10-45% of the hybridization total reaction volume.

In one embodiment, the present disclosure describes a kit comprising a probe set comprising at least two DNA probes complementary to discontiguous sequences along the full length of at least one off-target rRNA molecule (e.g., at least 5 bases apart or at least 10 bases apart along the full length) in a nucleic acid sample, a ribonuclease capable of degrading RNA in a DNA:RNA hybrid. In some embodiments, the probe set comprises any of the DNA probes described herein, or any combination thereof.

In some embodiments, a kit comprises a buffer and nucleic acid purification medium. In some embodiments, the kit comprises one or more of a buffer, a nucleic acid purification medium, and a DNA probe set as described herein. In some embodiments, the probe set comprises two or more sequences of SEQ ID NOs: 1-333. In some embodiments, the probe set comprises two or more sequences of SEQ ID NOs: 1-428. In some embodiments, a probe set comprises two or more, or five or more, or 10 or more, or 25 or more, or 50 or more, or 100 or more, or 150 or more, or 200 or more, or 250 or more, or 300 or more, or 350 or more, or 377 sequences from SEQ ID NOs: 1-377 (human, Gram-positive bacteria, Gram-negative bacteria, and Archaea). In some embodiments, a probe set comprises two or more, or five or more, or 10 or more, or 25 or more, or 50 or more, or 100 or more, or 150 or more, or 200 or more, or 250 or more, or 300 or more, or 350 or more, or 384 sequences from SEQ ID NOs: 1-333 and SEQ ID NOs: 378-428 (human, Gram-positive bacteria, Gram-negative bacteria, mouse, and rat). In some embodiments, a probe set comprises two or more, or five or more, or 10 or more, or 25 or more, or 44 sequences from SEQ ID NOs: 334-377 (Archaea). In some embodiments, a probe set comprises two or more, or five or more, or 10 or more, or 25 or more, or 50 or more, or 51 sequences from SEQ ID NOs: 378-428 (mouse and rat).

In some embodiments, the kit comprises: 1) probe set as described herein; 2) a ribonuclease; 3) a DNase; and 4) RNA purification beads. In some embodiments, the kit comprises an RNA depletion buffer, a probe depletion buffer, and a probe removal buffer.

Analysis of Depleted Samples

The disclosed methods also find utility in analyzing transcriptomes from single or mixed samples. Transcriptomic analysis can be impeded by high relative abundance of ribosomal RNA, for example a sample may comprise ≥85% of rRNA molecules in total RNA from bacterial cells. With such high amounts of rRNA competing for sequencing or other analysis reagents it can be difficult to focus on the more informative parts of a transcriptome which can get lost in the background of unwanted rRNA analysis. The disclosed methods can facilitate rich transcriptome analysis of microbial or eukaryotic isolates, for example, at low inputs of DNA, leading to lower rRNA sequencing reads, enabling lower sequencing costs and enabling metatranscriptomic analysis of low biomass samples. This is exemplified in Example 4, where low input amounts (<80 ng) from mixed samples were evaluated using the RNase H rRNA depletion methods described in this disclosure. The methods described herein can be used in conjunction with a variety of downstream applications, such as creating libraries for nucleic acid sequencing techniques, using the enriched samples in RT-PCR followed by microarray analysis, PCR, qPCR, etc. However, it should be understood that the enriched RNA samples resulting from the RNA depletion methods described here are not limited to any particular downstream application, such as sequencing.

As an example, the RNA depleted samples can be used to create sequencing libraries, such that the libraries created can be attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

Sequencing methodologies that can leverage the RNA depletion workflows and RNA enriched samples include, but are not limited to, cycle sequencing that is accomplished by stepwise addition of reversible terminator nucleotides containing, for example, a cleavable or photobleachable dye. Examples of Illumina instruments that can leverage the methods described herein include HiSeq™, MiSeq™, NextSeq™, NovaSeq™, NextSeq™, and iSeq™ commercial instruments.

Additional sequencing techniques include sequencing by ligation. Such techniques utilize DNA ligase to incorporate oligonucleotides and identify the incorporation of such oligonucleotides.

Further, nanopore sequencing can also use the disclosed RNA depleted samples for library preparation. Nanopore sequencing methods sequence a strand of nucleic acids that pass through a pore wherein change is current through the pore is characteristic of which nucleotide is passing through the pore.

Further, sequencing using real-time monitoring of DNA polymerase activity can utilize the RNA depleted samples.

Additional SBS technologies that can create libraries for sequencing using the RNA depleted samples described herein include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary).

Additional downstream application that can leverage the enriched samples following RNA depletion as described herein include PCR, qPCR, microarray analysis, etc. For example, microarray analysis is a powerful technique for studying gene expression. The enriched samples can be used in microarray analysis by converting the enriched RNA to cDNA following methods known to a skilled artisan (e.g., reverse-transcriptase polymerase chain reaction RT-PCR). The cDNA could then be immobilized on substrates, microarray probes applied and expression analysis determined following any number of microarray analysis methodologies (for example, Agilent, Affymetrix, and Illumina to name a few sell commercial microarray analysis systems). Polymerase chain reaction (PCR) or quantitative PCR (qPCR) could also utilize the enriched sample as a substrate following established techniques (Current Protocols for Molecular Biology).

As such, the RNA depleted samples resulting from the methods described herein can be used to create sequencing libraries, amplification products, and the like which can be utilized for downstream analysis methodologies. The disclosed methods are not limited by any downstream application.

EXAMPLES

The following examples are illustrative only and are not intended to limit the scope of the application. Modifications will be apparent and understood by skilled artisans and are included within the spirit and under the disclosure of this application.

Example 1—Depletion of Unwanted RNA Species from a Sample

In this example total RNA is the target nucleic acid in the sample, and RNA depletion involves four main steps: 1) hybridization, 2) RNase H treatment, 3) DNase treatment, and 4) target RNA clean up.

Hybridization is accomplished by annealing a defined DNA probe set to denatured RNA in a sample. A RNA sample, 10-100 ng, is incubated in a tube with 1 µL of a 1 µM/oligo DNA oligo probe set (probes corresponding to SEQ ID NOs: 1-333, as listed in Table 1), 3 µL of 5× Hybridization buffer (500 mM Tris HCl pH 7.5 and 1000 mM KCl), 2.5 µL of 100% formamide and enough water for a total reaction volume of 15 µL. The hybridization reaction is incubated at 95° C. for 2 min to denature the nucleic acids, slow cooled to 37° C. by decreasing temperature 0.1° C./sec and held at 37° C. No incubation time needed once the reaction reaches 37° C. The total time it takes for denaturation to reach 37° C. is about 15 min.

Following hybridization, the following components are added to the reaction tube for RNase H removal of the unwanted RNA species from the DNA:RNA duplex; 4 µL 5× RNase H buffer (100 mM Tris pH 7.5, 5 mM DTT, 40 mM $MgCl_2$) and 1 µL RNase H enzyme. The enzymatic reaction is incubated at 37° C. for 30 min. The reaction tube can be held on ice.

Following the removal of the RNA from the DNA:RNA hybrid, the DNA probes are degraded. To the 20 µL reaction tube, the following components are added: 3 µL 10× Turbo DNase buffer (200 mM Tris pH 7.5, 50 mM $CaCl_2$), 20 mM $MgCl_2$), 1.5 µL Turbo DNase (Thermo Fisher Scientific) and 5.5 µL $H_2O$ for a total volume of 30 µL. The enzymatic reaction is incubated at 37° C. for 30 min followed by 75° C. for 15 min. The 75° C. incubation can serve to fragment the target total RNA to desired insert sizes for use in downstream processing, in this example the target insert size is around 200 nt of total RNA. The timing of this incubation step can be adjusted depending on the insert size needed for subsequent reactions, as known to a skilled artisan. Following incubation, the reaction tube can be held on ice.

After hybridization of the probes to the unwanted RNA, removal of the RNA, and removal of the DNA, the target total RNA in the sample can be isolated from the reaction conditions. The reaction tube is taken from 4° C. and allowed to come to room temperature and 60 µL of RNA-Clean XP beads (Beckman Coulter) are added and the reaction tube is incubated for 5 min. Following incubation, the tube is placed on a magnet for 5 min., after which the supernatant is gently removed and discarded. While still on the magnet, the beads with the attached total RNA are washed twice in 175 µL fresh 80% EtOH. After the second wash, the beads are spun down in a microcentrifuge to pellet the beads at the bottom of the tube, the tube is placed back on the magnet and the EtOH is removed, being careful to remove as much of the residual EtOH as possible without disturbing the beads. The beads are air dried for a few minutes, resuspended in 9.5 µL of ELB buffer (Illumina), allowed to sit a few more minutes at RT and placed back on the magnet to collect the beads. 8.5 µL of the supernatant is transferred to a fresh tube and placed on ice for additional downstream processing, such as created cDNA from the target total RNA.

In another example, 100 ng total RNA is diluted in 11 µL nuclease-free ultrapure water in each well of a 96-well PCR plate. To each well is added 4 µL of DNA probes (SEQ ID NOs: 1-333) in hybridization buffer and the well contents are mixed and optionally centrifuged. The plate is heated at 95° C. for 2 min and then the temperature is reduced at 0.1° C. per second until the temperature reaches 37° C. and then held at 37° C. to hybridize the probes. The plate is centrifuged at 280×g for 10 seconds. To degrade the DNA:RNA hybrids, to each well is added 5 µL of RNase in buffer and the well contents are mixed. The plate is heated at 37° C. for 15 min and then held at 4° C. To each well is added 10 µL of DNase in buffer and the well contents are mixed. The plate is heated at 37° C. for 15 min and then held at 4° C. The sample plate is centrifuged at 280×g for 10 seconds. To each well is added 60 µL RNAClean XP beads and the well contents are mixed. The plate is incubated at room temperature for 5 min. The plate is placed on a magnetic stand until the supernatant is clear (about 5 min). The supernatant in each well is removed and discarded. The beads are washed twice with 80% ethanol. Residual ethanol is removed from each well and the plate is air-dried on the magnetic stand for 1 min. To each well is added 10.5 µL of elution buffer, the well contents are mixed, and the plate is incubated at room temperature for 2 min. The plate is sealed and centrifuged at 280×g for 10 seconds. The plate is placed on a magnetic stand until the supernatant is clear (about 2 min). From each well, 8.5 µL of supernatant is transferred to the corresponding well of a new plate.

Example 2—cDNA Synthesis

Further processing of the RNA from Example 1 could be making a library preparation from the RNA target nucleic acids that can be sequenced for example by NGS. To 8.5 µL of the final reaction from Example 1, 8.5 µL of Elute, Prime High Concentration Random Hexamer Mix buffer (EPH buffer, TruSeq Stranded Total RNA Kit, Illumina) is added for a total volume of 17 µL. The sample is incubated at 65° C. for 2 min to denature the nucleic acids. Following denaturation, the reaction tube can be held on ice. First strand synthesis is performed by adding 8 µL of a reverse transcription enzyme mix (9 µL First Strand Synthesis Mix (FSA, TruSeq Stranded Total RNA Kit, Illumina) and 1 µL Protoscript II RT, (NEB)) to the denatured sample for a total volume of 25 µL. The reaction mix is incubated in a heated lid thermocycler under the following conditions: 25° C. for 5 min, 42° C. for 25 min, 70° C. for 15 min. Once the first strand synthesis reaction is complete the reaction tube can be held on ice.

Second strand cDNA synthesis can be performed by adding 5 µL Resuspension Buffer (RSB, TruSeq Stranded Total RNA Kit, Illumina) and 20 µL Second Strand Marking Mix (SSM buffer, TruSeq Stranded Total RNA Kit, Illumina) to the iced sample. The reaction tube is incubated at 16° C. for 60 min, and the sample may then be held on ice.

Following the cDNA synthesis steps, the cDNA can be cleaned up and separated from reaction components by, for example, adding 90 µL of SPB (Illumina) to the reaction tube and incubating for 5 min at RT. Following incubation, the tube is placed on a magnet for around 8 min to collect the paramagnetic beads and the supernatant is gently removed and discarded. While still on the magnet, the beads are washed twice with 175 µL fresh 80% EtOH. Following the washes, the beads are centrifuged to the bottom of the tube, the tube is place back on the magnet and EtOH is gently removed and discarded. The beads are dried for a few minutes and resuspended in 18.5 µL RSB, mixed well and allowed to incubate at RT for around 5 min before placed back on the magnet. Depending on the downstream application, the desired amount of purified cDNA can be removed to a new tube. In this example, a library prep for downstream sequencing is being made so 17.5 µL of the supernatant is transferred to a new tube which can be kept on ice.

Example 3—Library Preparation for Next Generation Sequencing

One method for preparing a library for sequencing includes A-tailing cDNA fragments, ligating adaptors, amplifying target fragments, and quantifying resultant fragments prior to sequencing.

The tube with 17.5 µL of purified cDNA from Example 2 is used for processing. To the purified cDNA is added 12.5 µL ATL (Illumina) for A-tailing the fragments. The reaction tube is incubated at 37° C. for 30 min followed by incubating at 70° C. for 5 min and the tube is put back on ice. Adaptors are ligated to the A-tailed sample by added in order: 2.5 µL RSB, 2.5 µL Index Adaptors (TruSeq Stranded Total RNA Kit, Illumina) and 2.5 µL of Ligation buffer (Illumina). The reaction tube is incubated at 30° C. for 10 min after which point 5 µL of Stop Ligation buffer (Illumina) is added and the reaction is held on ice.

Once the adaptor ligation reaction is completed, the ligated fragments are separated from the reaction components. To purify the adaptor ligated fragments, 34 µL SPB is added to the reaction tube which is incubated at RT for around 5 min. The tube is then placed on a magnet for capturing the paramagnetic beads and the beads are washed twice with 175 µL 80% EtOH, the EtOH being gently removed after the second wash. Following a 3 min air dry of the beads, the beads are resuspended in 52 µL RSB, the slurry in mixed, allowed to sit at RT for an additional 5 min, and placed back on the magnet. The supernatant (50 µL) is transferred to a fresh tube for a second round of bead cleanup.

For the second round, 40 µL SPB is added to the 50 µL sample and the process described above is repeated except the final purified fragments are resuspended in 21 µL of RSB and 20 µL of the final purified sample is transferred to a new reaction tube for subsequent amplification which increases the amount of target sequence for optimized sequencing results.

To the 20 µL of purified adaptor ligated sample, 5 µL of PCR primer cocktail (PPC, TruSeq Stranded Total RNA Kit, Illumina) and 25 µL PPM (TruSeq Stranded Total RNA Kit, Illumina) are added and the following amplification program in a heated lid thermocycler is performed: 98° C. for 30 sec followed by the cycled program 98° C. at 10 sec, 60° C. at 30 sec, 72° C. at 30 sec. The number of amplification cycles is dependent on the amount of RNA input at the beginning of the whole process. For example, for 100 ng RNA, approximately 12-13 cycles can be adequate, for 10 ng 15-16 cycles, and for 1 ng 17-18 cycles may be needed. The number of amplification cycles is typically optimized for any preparation as known to a skilled artisan.

The amplicons can be purified away from reaction conditions by adding 50 µL SPB to the reaction tube, incubate at RT, centrifuge the tube to pellet the beads and magnetically capture the beads. The supernatant can be discarded and the beads washed as previously stated followed by resuspension of the washed beads in 26 µL RSB, magnetic bead capture and transfer of the supernatant containing the DNA library for sequencing to a fresh tube. The library is typically quantified and analyzed prior to sequencing, for example by measuring an aliquot using the Qubit™ High Sensitivity kit (Thermo Fisher Scientific) and/or running an aliquot on a Bioanalyzer (Agilent). A skilled artisan will appreciate the many ways in which nucleic acids in a sample can be quantitated.

The resulting library preparation can then be used for next generation sequencing, microarray analysis or other downstream applications. For applications such as sequencing, the library preparation methodology is determined by the sequencing instrument being used and the companion library preparation method defined for that sequencing instrument. In this example, the library preparation method is characteristic of library creation when sequencing on Illumina sequencing instruments. A skilled artisan will understand that library preparation methods may vary depending in sequencing instrumentation, as such the present examples are exemplary only and the present RNA depletion methods are not limited to any particular library preparation workflow. Indeed, the present methods provide a RNA depleted sample that can input into any downstream applications that would benefit from a RNA sample depleted of unwanted RNA species.

Example 4—Microbial Transcriptome Analysis

In this example, microbial isolates, a mixed sample of bacterial species, and a standard cell mix were obtained from ATCC for testing.

| Sample type | Microbial species tested |
| --- | --- |
| Microbial isolates | E. coli, B. subtilis, S. Epidermidis, E. cloacae and B. cereus |
| ATCC-MSA2002 20 strain mix | A. baumannii, A. odontolyhticus, B. cereus, B. vulgatus, B. adolescentis, C. beijerinckii, C. acnes, D. radiodurans, E. faecalis, E. coli, H. pylori, L. gasseri., N. meningitidis, P. gingivalis, P. aeruginosa, R. sphaeroides, S. aureus, S. epidermidis, S. agalactiae, S. mutans |
| ATCC MSA2006 Human gut mix | B. tragilis, B. vulgatus, B. adolescentis, C. difficile, E. faecalis, L. plantarum, E. cloacae, E. coli, H. pylori, S. enterica, y. enterocolitica, F. nucleatum |

Total RNA can be extracted using the RNeasy Power Microbiome Kit (Qiagen) following manufacturer's protocol and evaluated for integrity and quantified by Bioanalyzer RNA Electrophoresis (Agilent). 10-250 ng of total RNA from each sample can be used for rRNA depletion following either the RiboZero methodology (Illumina, following manufacturer's protocol) or the methods disclosed herein using RNase H enzymatic degradation of unwanted rRNA. Ribo-depleted and non-ribo depleted RNA (control) samples can be prepared for sequencing using the TruSeq Stranded Total RNA Sample prep kit (Illumina) following manufacturer's instructions. Libraries can be pooled and sequenced, for example, on a MiSeq or NextSeq sequencing instrument (Illumina) for 2×76 paired end reads.

Sequence filtering, alignment, and transcript coverage can be performed using the online BaseSpace Sequencing Hub (BSSH) and the following exemplary workflows, for example: 1) Partition rRNA Sequences App (parse rRNA sequences to denote as abundant sequences in analysis), 2) RNA Custom Genome Builder App (create STAR-compatible microbial transcriptome), and 3) RNA-Seq Alignment App (STAR-alignment and salmon-transcript quantification). To quantify rRNA from multiple strains within the microbial samples rRNA sequences can be retrieved from NCBI annotated genomes and used as inputs to the BSSH workflow.

Figure 5:
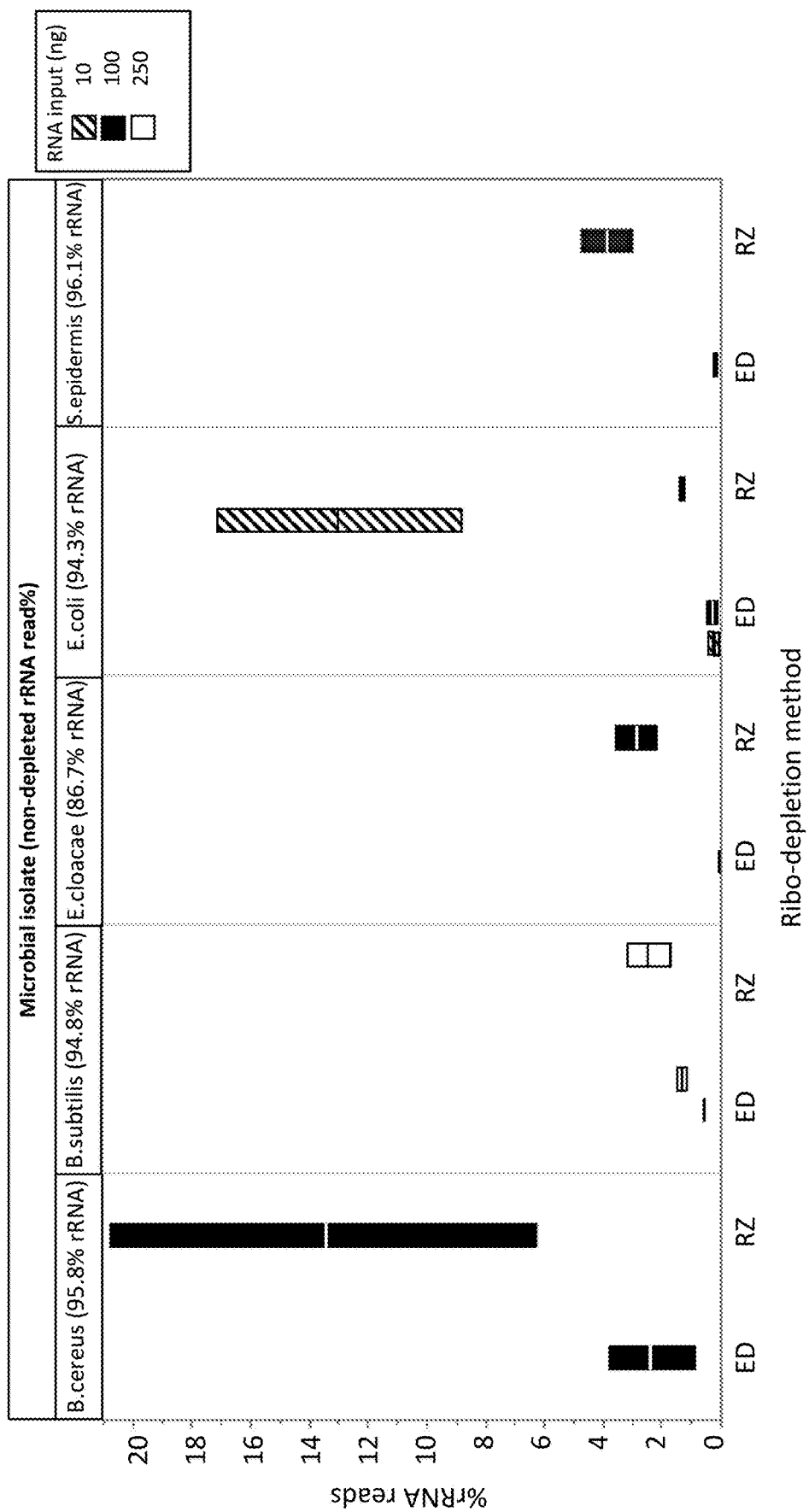
FIG. 5 shows exemplary data from removal of rRNA from different microbial species using low sample inputs comparing RiboZero® and RNase H enzymatic removal rRNA depletion methodologies. All sample read-depths were normalized. The X axis shows the rRNA depletion method (RZ=RiboZero or ED=RNase H enzymatic depletion method) and the Y axis shows the % rRNA reads.

The transcriptomes of the microbial isolates, microbial mixtures and control samples were sequenced and % rRNA reads compared. The RNase H enzymatic method disclosed herein is highly effective in depleting unwanted rRNA in the tested species (<5% rRNA reads). Ribosomal RNA depletion is most significant for the *E. coli* low input sample (10 ng) using the RNase H method comparative to the established RiboZero method; <0.5% vs 13% average rRNA reads, respectively (FIG. 5).

Figure 6:
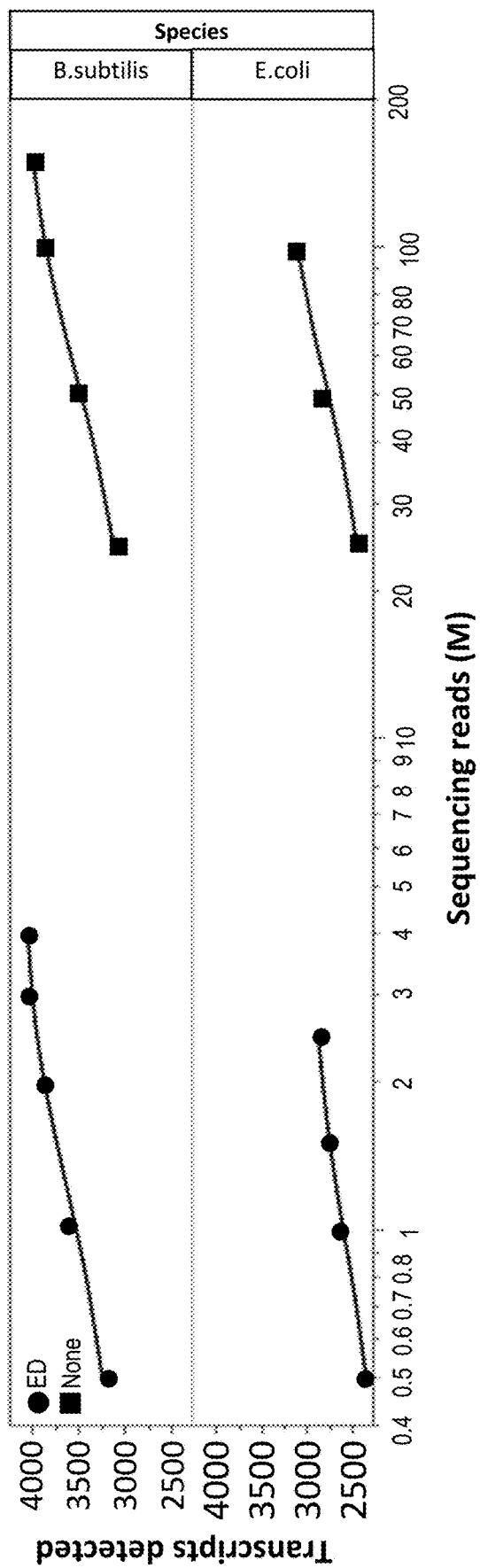
FIG. 6 shows exemplary transcript detection data at various read depths for B. subtilis and E. coli following RNase H rRNA depletion (ED) on the left side of the graph compared to no rRNA depletion (None) on the right side of the graph. The X axis shows the sequencing reads (M) and the Y axis shows the number of transcripts detected.

Data was used to access the enrichment of biologically important RNA reads when the RNase H rRNA depletion method was used and compared to no rRNA depletion. FIG. 6 demonstrates the results of an assessment where, in general, a 20-50× reduction in read depth was seen for a *B. subtilis* or *E. coli* sample if the sample was rRNA depleted prior to library preparation and sequencing using the RNase H methods compared to no rRNA depletion.

Figure 7A:
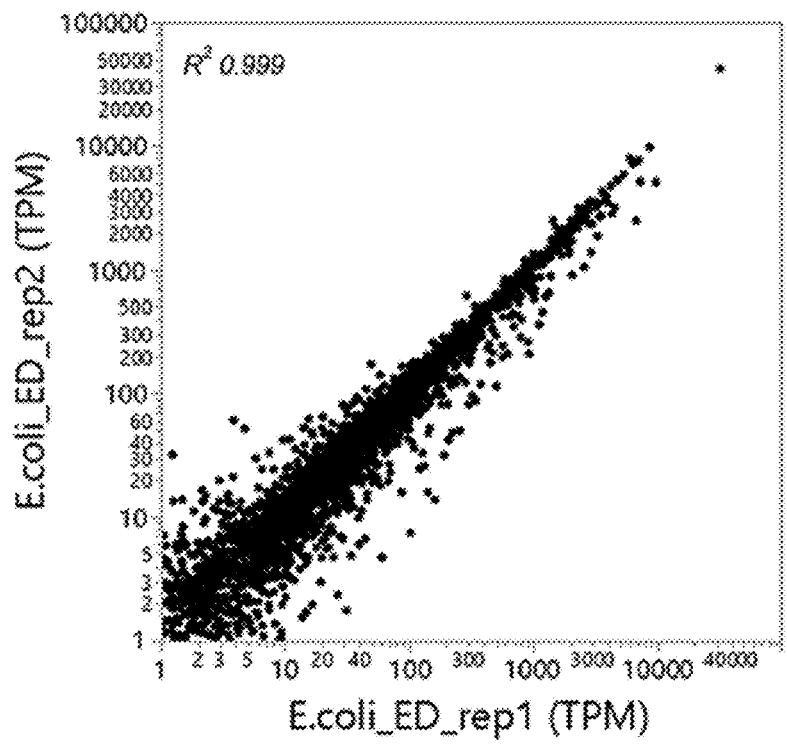
FIGS. 7A-7B show exemplary graphs for gene expression pairwise linear regression data demonstrating the reproducibility of the disclosed methods for rRNA depletion. Panel 7A exemplifies two E. coli replicate gene expression levels and Panel 7B exemplifies two B. subtilis replicate gene expression levels. Both bacterial types demonstrate high correlation between gene expression level replicates following RNase H rRNA depletion.
Figure 7B:
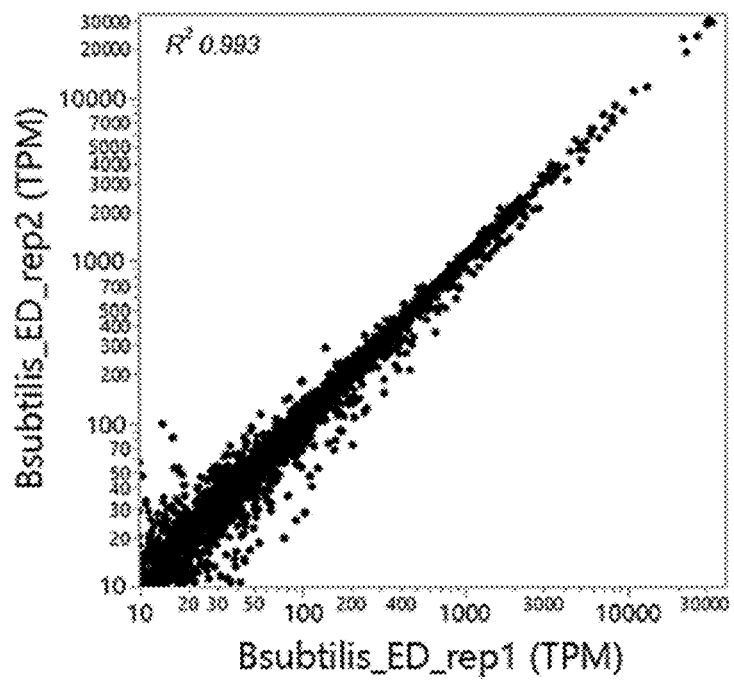

Data collected was evaluated to determine the reproducibility of the experimental microbial transcriptome sequencing efforts. Pairwise linear regression of gene expression levels was determined between the RNase H rRNA depleted replicates for *E. coli* and *B. subtilis* as example systems. High correlation ($R^2$>0.99) indicated the ability of the RNase H rRNA depletion method to reproducibly remove rRNA from samples (FIG. 7).

Figure 8:
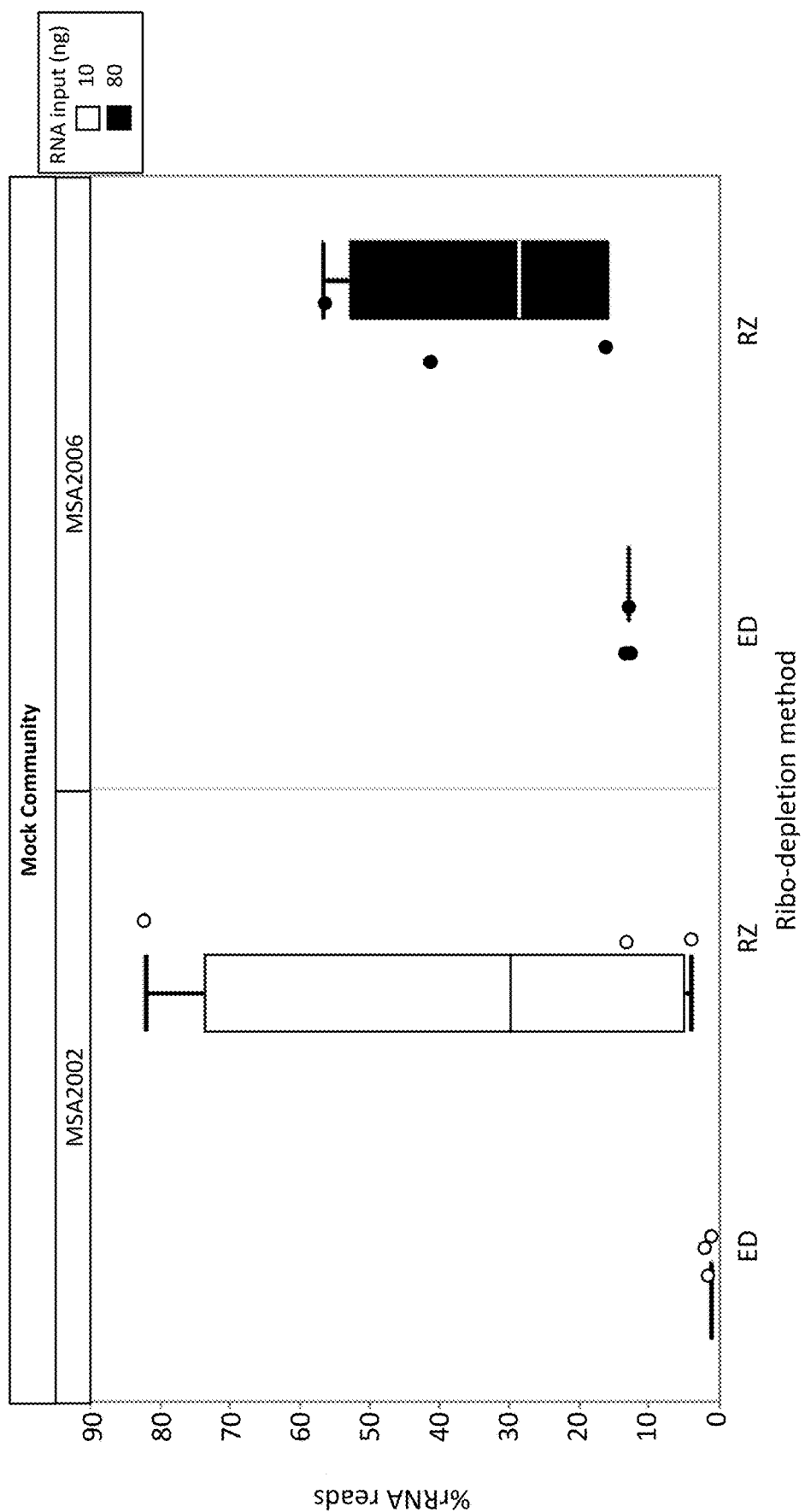
FIG. 8 shows exemplary triplicate rRNA read data for a 20 strain (MSA-2002, left side) and a 12 strain (MSA-2006, right side) mixed sample. The mixed sample triplicates were rRNA depleted by the RiboZero method (RZ) or the RNase H (ED) depletion method described herein. RNA input for the MSA2002 samples was 10 ng while that for the MSA2006 was 80 ng. The X axis shows the rRNA depletion method and the Y axis shows the % rRNA reads.

For evaluating whether the RNase H enzymatic rRNA depletion method might be useful for rRNA depletion of mixed samples, FIG. 8 demonstrates exemplary data for the mixed samples of 20 strain MSA2002 and human gut MSA2006 in triplicate. Low input samples of 10 mg total RNA from MSA2002 or 80 ng total RNA from MSA2006 was used for rRNA depletion methods. For the 20 strain MSA2002 samples, the RNase H rRNA depletion method reduced rRNA reads by 83% or <2% of sequence reads while the RiboZero method of rRNA depletion resulted in a more variable and higher rRNA abundance compared to non-depleted samples. For the 12 strain MSA2006 samples, the same outcome was seen where RNase H method reduced rRNA reads by approximately 95% to <13% of the sequencing reads comparative to non-depleted samples, the RiboZero method yielded more variable results.

As such, it was determined that in experiments for evaluating samples, either mixed or otherwise, the RNase H rRNA depletion method provides a robust and effective workflow for reducing unwanted rRNA in samples for high quality microbial whole transcriptome research. The RNase H rRNA depletion method was also very effective and compatible with low input samples.

Example 5—Effect of Formamide on RNA Depletion

Figure 2A:
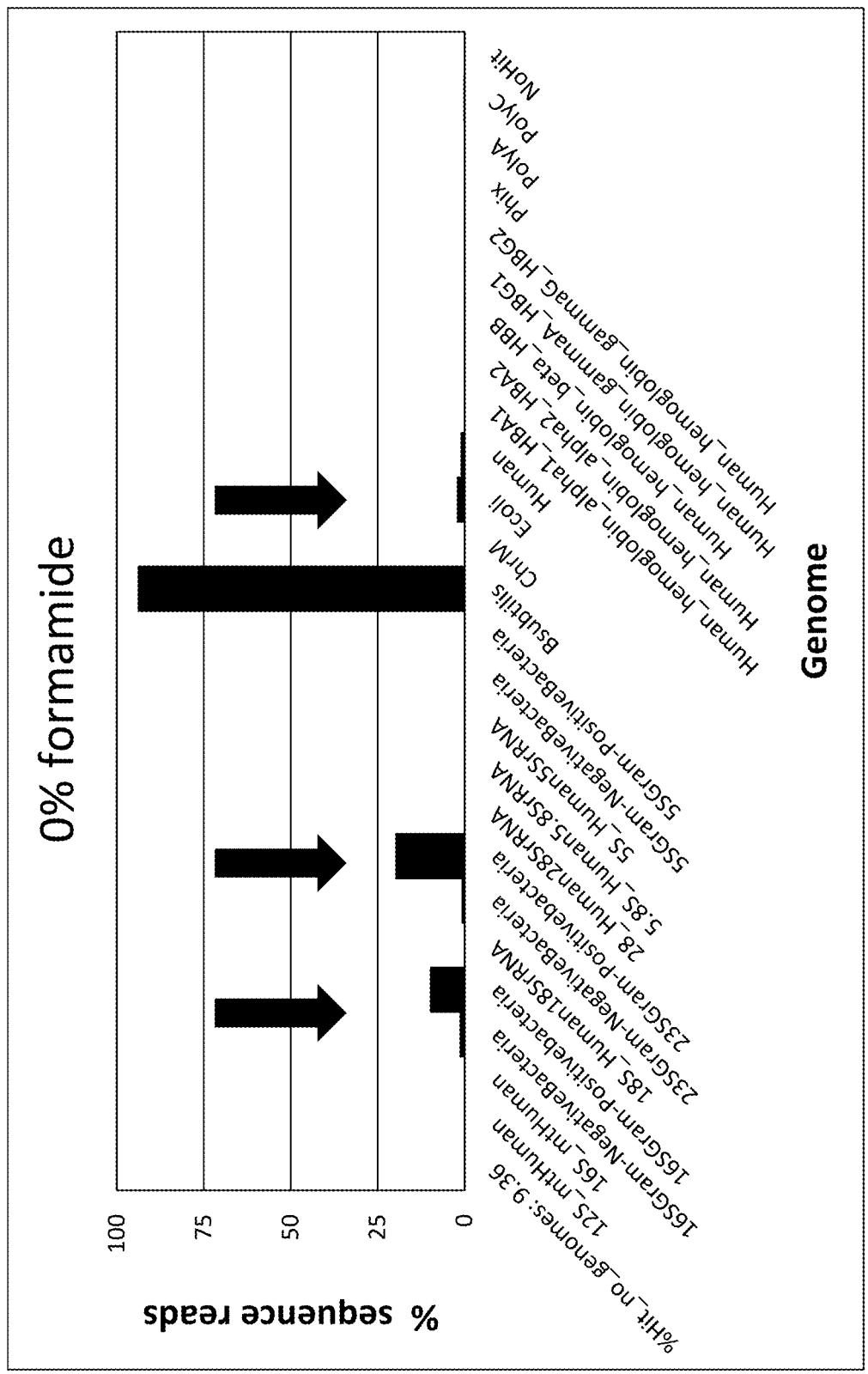
FIGS. 2A-2C show exemplary data for rRNA depletion from a sample of B. subtilis when formamide is added to the rRNA depletion workflow (2A) 0% formamide, (2B) 25% formamide, (2C) 45% formamide). In each panel, the X axis lists the detected rRNA species and the Y axis shows percent depletion through percent sequence reads.
Figure 2B:
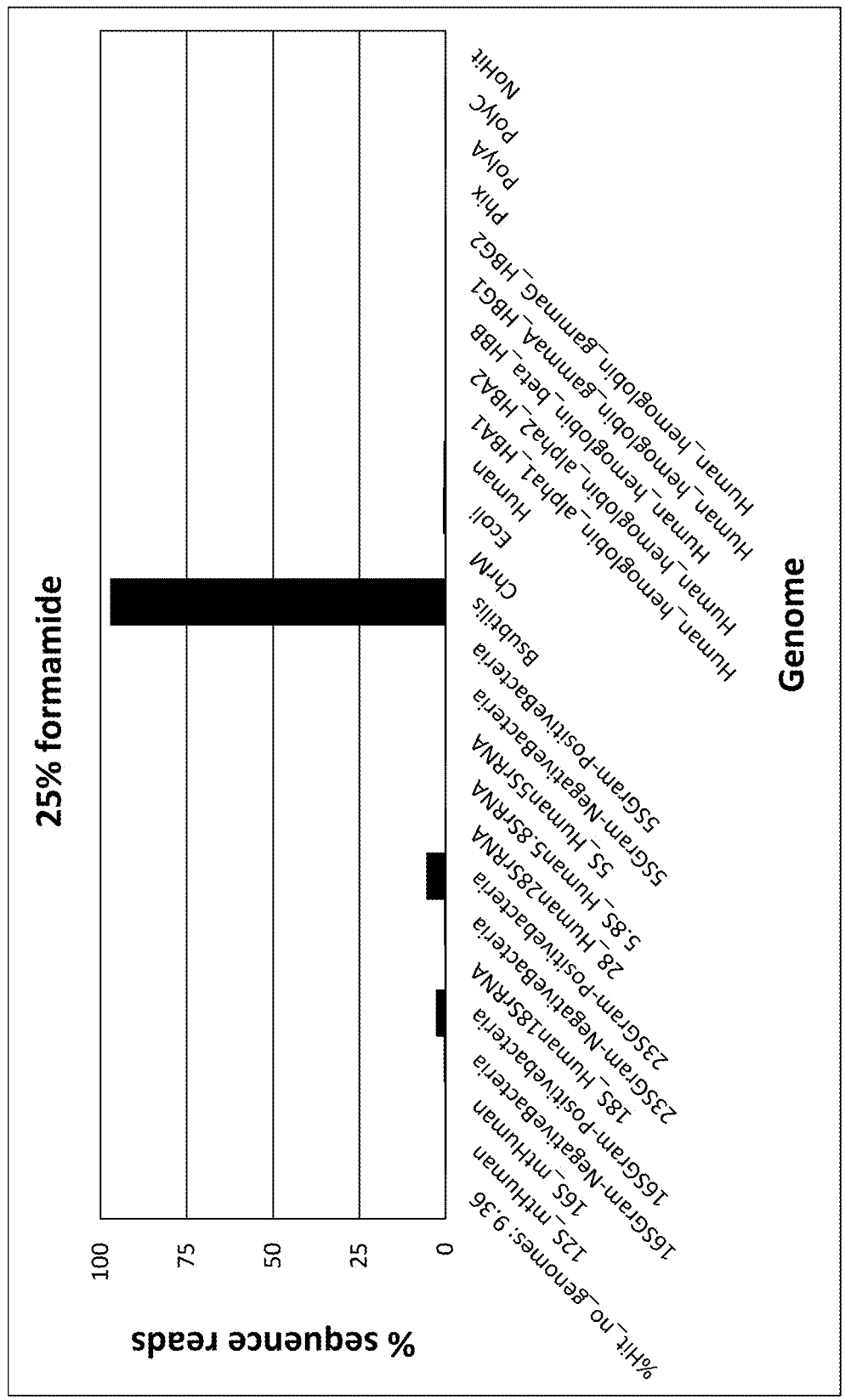
Figure 2C:
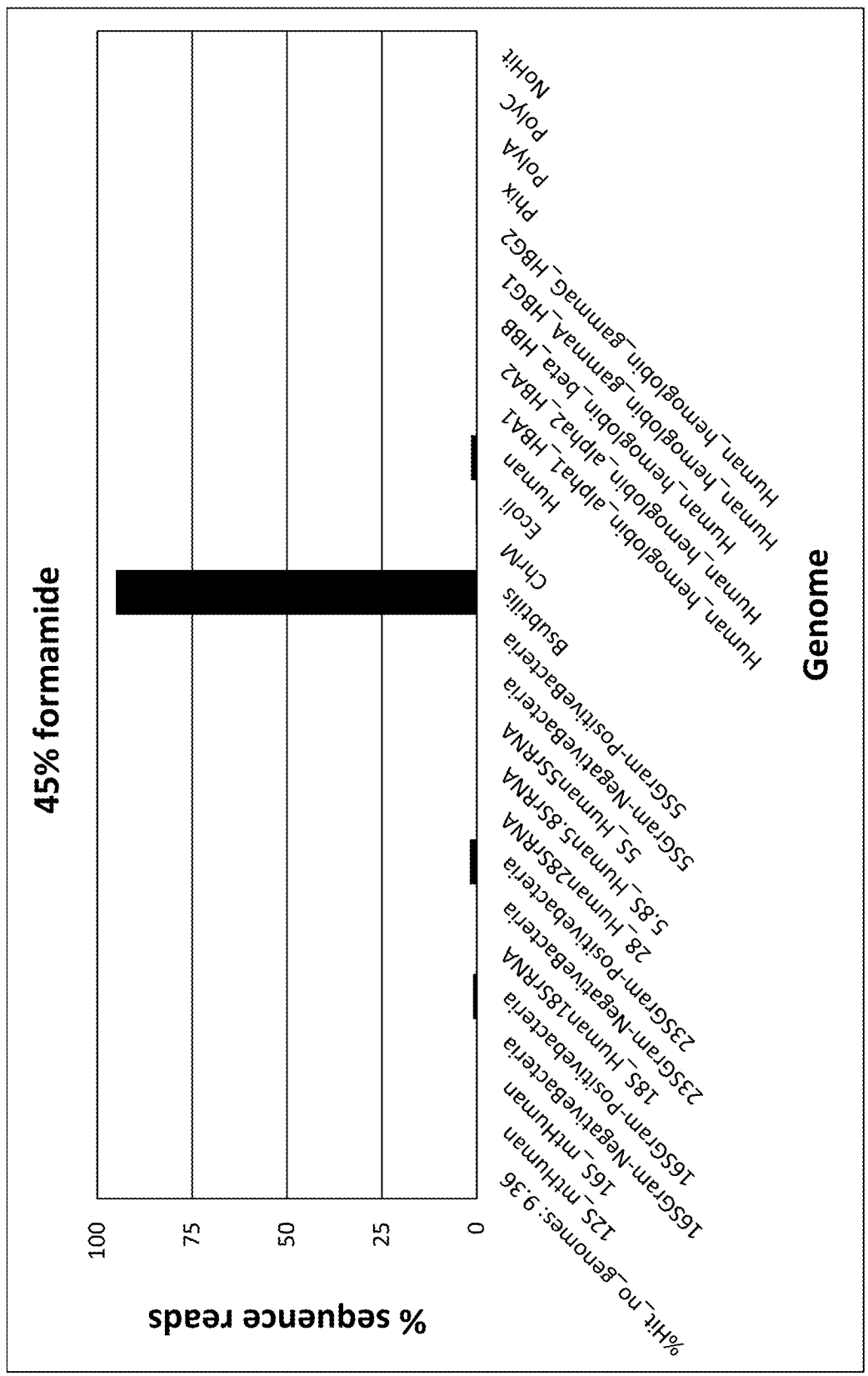

FIG. 2 shows exemplary data where an RNA sample has been depleted of unwanted RNA species. The RNA sample was depleted of unwanted RNA using the methods described herein, while evaluating the effects of formamide concentration on unwanted RNA depletion. In this example, the DNA probes targeted depletion of unwanted rRNA species from Gram positive bacteria (23S, 16S, 5S), Gram negative bacteria (23S, 16S, 5S including), human mitochondria (16S, 12S), human rRNAs (28S, 18S, 5.8S, 5S), human hemoglobin mRNAs (HBA-A1, HBA-A2, HBB, HBG1, HBG2) while the target RNA species is total RNA from *B. subtilis*. As the concentration of formamide increases the percentage of unwanted RNA species reads significantly decreases. For example, no formamide during RNA depletion resulted in off target RNA reads for Gram positive 23S and 16S and Gram negative (including *E. coli*) bacteria 23S and 16S, including *E. coli* specific sequences. The addition of 25% formamide to the hybridization reaction resulted in undetectable off target reads for Gram negative 23S and 16S (with significant reduction in off targets reads specific to *E. coli*) and significantly reduced off target reads for the Gram positive 23S and 16S. The addition of formamide to 45% of the hybridization reaction saw additional significant decreases in off target reads for the Gram positive undesired rRNA 23S and 16S as well as a further drop in off target *E. coli* reads. As such, the addition of formamide to the RNA depletion hybridization reaction is shown to increase the amount of Gram positive and Gram negative undesired RNAs depleted as evidenced by the reduction in off target reads for those species. In general, it was found that the addition of formamide improves depletion of the unwanted rRNA transcripts. When using *B. subtilis* RNA as the target RNA for analysis, for example, assaying for *E. coli* and human rRNA sequences can provide a measure of potential contamination.

Example 6—Variation of Input Starting Material

Experiments were performed to identify the impact of input starting material on RNA depletion and subsequent downstream analysis, such as shown in FIG. 3 where RNA depleted and enriched RNA samples from human brain (HBR) and a universal human RNA (UHR) were used to create libraries for sequencing on the Illumina NextSeq™ 500 or 550 sequencing instrument. Following RNA depletion using 100 ng, 10 ng or 1 ng of input samples, sequencing libraries were prepared as exemplified in Examples 1-3. Sequencing was performed as recommended by the NextSeq™ user guide following by data analysis using two BaseSpace (Illumina) applications, RNASeq Alignment application and the RNAExpress application. Data analysis for *B. subtilis* and *E. coli* presence was also performed using a modified tool Fastqscreen (https://www.bioinformatics.babraham.ac.uk/projects/fastq_screen/). The data shows that the RNA depletion remains constant for both HBR and UHR regardless of amount of input of the RNA sample and the % total alignment for the target RNA, while decreasing with decreasing input amounts, still shows that actionable and useful sequence data can be gathered even when using 1 ng of input sample. Further, in a comparative experiment the current method for RNA depletion leads to fewer % abundance of non-target reads at all input levels (100 ng~3%, 25 ng~4%, 10 ng~3% and 1 ng~3%) when compared to data when using RiboZero rRNA depletion kit (Epicentre) for RNA depletion (100 ng~3%; 25 ng~5%, 10 ng~8% and 1 ng~35%) or NEBNext rRNA depletion methods (NEB) (100 ng~8%, 25 ng~8%, 10 ng~9% and 1 ng~30%).

Example 7—RNA Depletion of Mouse and Rat RNA Samples

To demonstrate that the RNA depletion methods can be useful for non-human RNA samples both mouse and rat RNA samples were used for RNA depletion methods. For FIG. 4, either mouse or rat RNA samples were depleted of unwanted RNA using equivalent methods and DNA probes as for human RNA samples. Formamide was again varied for each rodent species, including no formamide, 25% formamide or 45% formamide in the hybridization reaction. While total % aligned reads is not affected with the increase in formamide, there may be a trend toward an increase in detection of non-target reads as formamide increases. As such, the addition of formamide to the hybridization reaction may be useful in some sample types, as it can improve detection of some transcripts so its addition should be optimized.

Example 8—Preparation of Supplemental Mouse Probes

Within the pool of 333 DNA probes described above for enzymatic removal of unwanted sequences (SEQ ID NOs: 1-333), the DNA oligonucleotides for eukaryotic rRNA depletion were designed based upon the major human rRNA transcripts, namely 5S, 5.8S, 18S, and 28S, as well as the two mitochondrial rRNA sequences, 12S and 16S. When tested on human total RNA, this 333-DNA probe pool was very effective at removing rRNA reads. However, when tested with mouse (*Mus musculus*) or rat (*Rattus norvegicus*) total RNA samples, depletion was less robust, suggesting that the probes did not hybridize and remove some regions of rodent rRNA sequences efficiently because these mouse and rat regions were divergent from human sequences.

Figure 9:
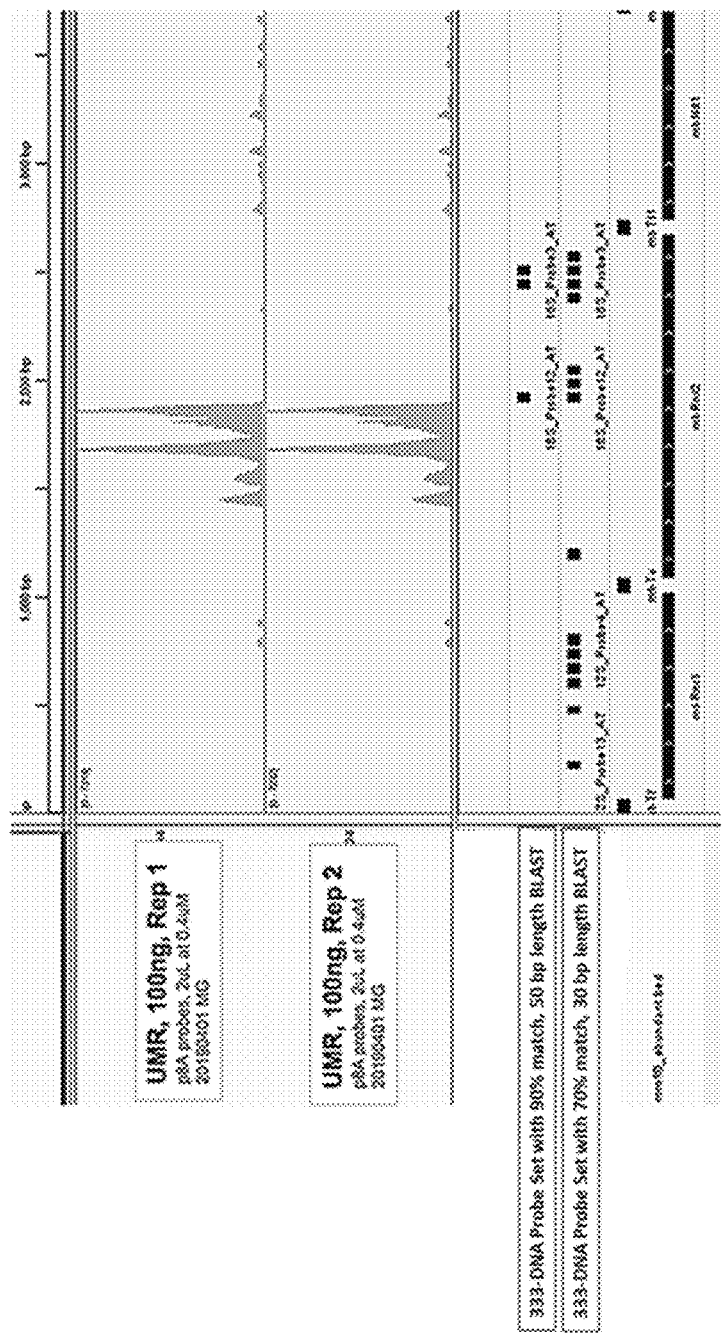
FIG. 9 shows sequencing read coverage of the mouse mitochondrial 12S (mt-Rnr1 and 16S (mt-Rnr2) rRNA loci (bottom of the figure) and the effect of the 333 DNA probe set (SEQ ID NOs: 1-333) on depleting mouse 16S rRNA from universal mouse reference RNA (UMR) samples. Squares indicate location of 90% match over 50 base length or 70% match over 30 base pair length with the 333 DNA probe set. In the absence of additional mouse and rat probes, gaps without probe coverage correspond to peaks in residual or undepleted rRNA for the two replicates (Rep 1 and Rep2) shown at the top of the figure.

The fastq files containing the total sequencing reads obtained from the 333-DNA probe experiment were aligned to mouse and rat ribosomal RNA sequences and to the 333 DNA probe sequences. The alignment results showed that probe coverage across all the ribosomal RNA sequences was generally good, but there were some regions where probe sequences did not align as well to rodent rRNAs. More specifically, the majority of the mouse and rat rRNA reads that did not align to the probe pool map belonged to either the 28S or 16S rodent rRNA transcripts (Table 2). The alignments were done with Bowtie2 (See Langmead and Salzberg, *Nature Methods* 2012, 9:357-359), version 2.1.0 with its default settings. Most of the ribosomal RNA that did not get depleted with the 333 DNA probe enzymatic method were from the same regions that lacked probe alignment (FIG. 9).

TABLE 2

| Mouse/Rat Genbank sequences used for the study | | |
|---|---|---|
| Genome | 16S | 28S |
| *Mus musculus* | NC_005089.1:1094-2675 | NR_003279.1 |
| *Rattus norvegicus* | NC_001665.2:1094-2664 | NR_046246.1 |

To deplete these regions more effectively, additional probes were designed to cover the regions identified above for mouse and rat ribosomal RNA sequences. To minimize the number of additional probes and probe redundancies, additional probes were designed against the gaps in mouse rRNA sequences, then these data were informatically pooled together with the 333 DNA probe set to identify any remaining gaps in rat rRNA coverage by aligning the combined pool to rat rRNA transcripts. This sequential process yielded a total of 44 additional oligonucleotide probes, to provide a supplemental pool of 377 probes. Sequencing experiments as described above were repeated with the 377 DNA probe set. In both mouse and rat samples, addition of the 44 new probes resulted in a decrease in the percentage of rRNA reads from the libraries compared to the 333-DNA probe set, showing increased depletion efficiency (Table 3).

TABLE 3

| Percent ribosomal RNA in sequencing reads with 333- and 377-Probe Sets | | |
|---|---|---|
| RNase H Probe Set | Mouse Sample | Rat Sample |
| 333 DNA Probe Set | 9.5% | 5.3% |
| 377 DNA Probe Set | 7.0% | 3.7% |

Supplementation of the 333 DNA probe pool with additional probes against certain rodent sequences improved rRNA depletion in the tested rodent samples. Exemplary probes against mouse 16S include SEQ ID NOs: 385 to 393. Exemplary probes against mouse 28S include SEQ ID NOs: 400 to 419. Exemplary probes against rat 16S include SEQ ID NOs: 394 to 399. Exemplary probes against rat 28S include SEQ ID NOs: 420 to 428.

The invention claimed is:

1. A method for depleting off-target RNA molecules from a nucleic acid sample comprising:
   a. contacting a nucleic acid sample comprising at least one target RNA or DNA sequence and at least one off-target RNA molecule with a probe set comprising at least 40 DNA probes complementary to discontiguous sequences along the full length of the at least one off-target RNA molecule, thereby hybridizing the at least 40 DNA probes to the off-target RNA molecules to form DNA:RNA hybrids, wherein
      i. each of the at least 40 DNA probes is 40 to 60 bases in length, and
      ii. each DNA:RNA hybrid is from 5 to 40 bases apart, along a given off-target RNA molecule sequence from any other DNA:RNA hybrid; and
   b. contacting the DNA:RNA hybrids with a ribonuclease that degrades the RNA from the DNA:RNA hybrids, thereby degrading the off-target RNA molecules in the nucleic acid sample to form a degraded mixture, optionally wherein the ribonuclease is RNase H or Hybridase.

2. The method of claim 1, comprising:
   c. optionally degrading any remaining DNA probes by contacting the degraded mixture with a DNA digesting enzyme, optionally wherein the DNA digesting enzyme is DNase I, to form a DNA degraded mixture; and
   d. separating the degraded RNA from the degraded mixture or the DNA degraded mixture.

3. The method of claim 1, wherein the contacting with the probe set comprises treating the nucleic acid sample with a destabilizer, wherein the destabilizer is
   a. heat, optionally wherein the heat is above the melting temperature of the at least one DNA:RNA hybrid; or
   b. a nucleic acid destabilizing chemical, optionally wherein the nucleic acid destabilizing chemical is betaine, DMSO, formamide, glycerol, or a derivative thereof, or a mixture thereof; further optionally wherein the formamide is present during the contacting with the probe set at a concentration of from about 10 to 45% by volume.

4. The method of claim 1, wherein the nucleic acid sample is from a human or from a non-human eukaryote, bacterium, virus, plant, soil, or a mixture thereof, optionally wherein the non-human eukaryote is a rat, mouse, or non-human primate.

5. The method of claim 1, wherein the off-target RNA is rRNA, mRNA, tRNA, or a mixture thereof; optionally wherein the off-target RNA is rRNA and globin mRNA.

6. The method of claim 1, wherein the probe set comprises at least two DNA probes that hybridize to at least one off-target RNA molecule:
   a. selected from 28S, 23S, 18S, 5.8S, 5S, 16S, 12S, HBA-A1, HBA-A2, HBB, HBB-B1, HBB-B2, HBG1, and HBG2, optionally wherein the probe set comprises at least two DNA probes that hybridize to two or more off-target RNA molecules selected from 28S, 18S, 5.8S, 5S, 16S, and/or 12S from humans;
   b. selected from HBA-A1, HBA-A2, HBB, HBG1, and HBG2 from hemoglobin, and 23S, 16S, and 5S from Gram positive or Gram negative bacteria;
   c. from an Archaea species; and/or
   d. from rat and/or mouse, optionally wherein the probe set comprises at least two DNA probes that hybridize to one or more off-target RNA molecules selected from rat 16S, rat 28S, mouse 16S, and mouse 28S, and combinations thereof.

7. The method of claim 1, wherein the probe set comprises DNA probes to a particular off-target RNA molecule that are complementary to about 80 to 85% of the sequence of the off-target RNA molecule, optionally wherein the DNA probes comprise:
   a. two or more sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
   or a combination thereof.

8. A composition comprising
   a. a probe set comprising at least 40 DNA probes complementary to discontiguous sequences along the full length of at least one off-target RNA molecule in a nucleic acid sample, wherein each of the at least 40 DNA probes is 40 to 60 bases in length; and
   b. a ribonuclease capable of degrading RNA in a DNA:RNA hybrid; optionally wherein the ribonuclease is RNase H and/or each DNA probe is hybridized from 5 to 40 bases apart along the full length of the at least one off-target RNA molecule from any other DNA probe in the probe set.

9. The composition of claim 8, wherein the composition comprises a destabilizing chemical; optionally wherein the destabilizing chemical is formamide.

10. The composition of claim 8, wherein the off-target RNA is rRNA, mRNA, tRNA, or a mixture thereof; optionally wherein the off-target RNA is rRNA and globin mRNA.

11. The composition of claim 8, wherein the probe set comprises at least two DNA probes that hybridize to at least one off-target RNA molecule:
   a. selected from 28S, 23S, 18S, 5.8S, 5S, 16S, 12S, HBA-A1, HBA-A2, HBB, HBG1, and HBG2, optionally wherein the probe set comprises at least two DNA probes that hybridize to two or more off-target RNA molecules selected from 28S, 18S, 5.8S, 5S, 16S, and/or 12S from humans;
b. selected from HBA-A1, HBA-A2, HBB, HBG1, and HBG2 from hemoglobin, and 23S, 16S, and 5S from Gram positive or Gram negative bacteria;
c. from an Archaea species; and/or
d. from rat and/or mouse, optionally wherein the probe set comprises at least two DNA probes that hybridize to one or more off-target RNA molecules selected from rat 16S, rat 28S, mouse 16S, and mouse 28S, and combinations thereof.

12. The composition of claim 8, wherein the probe set comprises DNA probes comprising:
   a. two or more sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
   or a combination thereof.

13. A kit comprising
   a. a probe set comprising at least 40 DNA probes complementary to discontiguous sequences that are from 5 to 40 bases apart along the full length of at least one off-target RNA molecule in a nucleic acid sample, wherein each of the at least 40 DNA probes is 40 to 60 bases in length; and
   b. a ribonuclease capable of degrading RNA in a DNA:RNA hybrid; optionally comprising a buffer and nucleic acid purification medium, and further optionally comprising a destabilizing chemical.

14. The kit of claim 13, wherein the off-target RNA is rRNA, mRNA, tRNA, or a mixture thereof, optionally wherein the off-target RNA is rRNA and globin mRNA.

15. The kit of claim 13, wherein the probe set comprises at least two DNA probes that hybridize to at least one off-target RNA molecule:
   a. selected from 28S, 23S, 18S, 5.8S, 5S, 16S, 12S, HBA-A1, HBA-A2, HBB, HBG1, and HBG2, optionally wherein the probe set comprises at least two DNA probes that hybridize to two or more off-target RNA molecules selected from 28S, 18S, 5.8S, 5S, 16S, and/or 12S from humans;
   b. selected from HBA-A1, HBA-A2, HBB, HBG1, and HBG2 from hemoglobin, and 23S, 16S, and 5S from Gram positive or Gram negative bacteria;
   c. from an Archaea species; and/or
   d. from rat and/or mouse, optionally wherein the probe set comprises at least two DNA probes that hybridize to one or more off-target RNA molecules selected from rat 16S, rat 28S, mouse 16S, and mouse 28S, and combinations thereof.

16. The kit of claim 13, wherein the probe set comprises DNA probes comprising:
   a. two or more sequences selected from SEQ ID NOs: 1-333; or
   b. two or more sequences selected from SEQ ID NOs: 1-428; or
   c. two or more sequences selected from SEQ ID NOs: 1-377; or
   d. two or more sequences selected from SEQ ID NOs: 1-333 and SEQ ID NOs: 378-428; or
   e. two or more sequences selected from SEQ ID NOs: 334-377; or
   f. two or more sequences selected from SEQ ID NOs: 378-428;
   or a combination thereof.

17. The kit of claim 13, comprising:
   a. a probe set comprising SEQ ID NOs: 1-333;
   b. a ribonuclease, optionally wherein the ribonuclease is RNase H;
   c. a DNase; and
   d. RNA purification beads;
   and optionally further comprising an RNA depletion buffer, a probe depletion buffer, and a probe removal buffer.

18. A method of supplementing a probe set for use in depleting off-target RNA nucleic acid molecules from a nucleic acid sample comprising:
   a. contacting a nucleic acid sample comprising at least one RNA or DNA target sequence and at least one off-target RNA molecule from a first species with a probe set comprising at least 40 DNA probes complementary to discontiguous sequences along the full length of the at least one off-target RNA molecule from a second species, thereby hybridizing the at least 40 DNA probes to the off-target RNA molecules to form DNA:RNA hybrids, wherein
      i. each of the at least 40 DNA probes is 40 to 60 bases in length, and
      ii. each DNA:RNA hybrid is from 5 to 40 bases apart, along a given off-target RNA molecule sequence from any other DNA:RNA hybrid, optionally wherein the first species is a non-human species and the second species is human, further optionally wherein the first species is rat or mouse;
   b. contacting the DNA:RNA hybrids with a ribonuclease that degrades the RNA from the DNA:RNA hybrids, thereby degrading the off-target RNA molecules in the nucleic acid sample to form a degraded mixture;
   c. separating the degraded RNA from the degraded mixture;
   d. sequencing the remaining RNA from the sample;
   e. evaluating the remaining RNA sequences for the presence of off-target RNA molecules from the first species, thereby determining gap sequence regions, optionally wherein the gap sequence regions comprise 50 or more base pairs; and
   f. supplementing the probe set with additional DNA probes complementary to discontiguous sequences in one or more of the gap sequence regions.

19. The method of claim 18, wherein the composition of claim 8 is used to supply the ribonuclease and the probe set comprising DNA probes complementary to discontiguous sequences along the full length of the at least one off-target RNA molecule of a human.

20. The method of claim 18, wherein the method is used to identify DNA probes that hybridize to one or more off-target RNA molecules from rat and/or mouse, optionally selected from rat 16S, rat 28S, mouse 16S, and mouse 28S, and combinations thereof.

* * * * *

SEQUENCE LISTING

```
<160> NUMBER OF SEQ ID NOS: 428

<210> SEQ ID NO 1
<211> LENGTH: 50
<212> TYPE: DNA
<213> ORGANISM: Artificial sequence
<220> FEATURE:
<223> OTHER INFORMATION: DNA Probe

<400> SEQUENCE: 1
gttcgtccaa gtgcactttc cagtacactt accatgttac gacttgtctc                50

<210> SEQ ID NO 2
<211> LENGTH: 50
<212> TYPE: DNA
<213> ORGANISM: Artificial sequence
<220> FEATURE:
<223> OTHER INFORMATION: DNA Probe
```

<400> SEQUENCE: 2
tagggttttt agttaaatgt cctttgaagt atacttgagg agggtgacgg          50

<210> SEQ ID NO 3
<211> LENGTH: 50
<212> TYPE: DNA
<213> ORGANISM: Artificial sequence
<220> FEATURE:
<223> OTHER INFORMATION: DNA Probe

<400> SEQUENCE: 3
ttcagggccc tgttcaacta agcactctac tctcagttta ctgctaaatc          50

<210> SEQ ID NO 4
<211> LENGTH: 50
<212> TYPE: DNA
<213> ORGANISM: Artificial sequence
<220> FEATURE:
<223> OTHER INFORMATION: DNA Probe

<400> SEQUENCE: 4
agtttcataa gggctatcgt agttttctgg ggtagaaaat gtagcccatt          50

<210> SEQ ID NO 5
<211> LENGTH: 50
<212> TYPE: DNA
<213> ORGANISM: Artificial sequence
<220> FEATURE:
<223> OTHER INFORMATION: DNA Probe

<400> SEQUENCE: 5
ggctacacct tgacctaacg tctttacgtg ggtacttgcg cttactttgt          50

<210> SEQ ID NO 6
<211> LENGTH: 50
<212> TYPE: DNA
<213> ORGANISM: Artificial sequence
<220> FEATURE:
<223> OTHER INFORMATION: DNA Probe

<400> SEQUENCE: 6
ttgctgaaga tggcggtata taggctgagc aagaggtggt gaggttgatc          50

<210> SEQ ID NO 7
<211> LENGTH: 50
<212> TYPE: DNA
<213> ORGANISM: Artificial sequence
<220> FEATURE:
<223> OTHER INFORMATION: DNA Probe

<400> SEQUENCE: 7
cagaacaggc tcctctagag ggatatgaag caccgccagg tcctttgagt          50

<210> SEQ ID NO 8
<211> LENGTH: 50
<212> TYPE: DNA
<213> ORGANISM: Artificial sequence
<220> FEATURE:
<223> OTHER INFORMATION: DNA Probe

<400> SEQUENCE: 8
gtagtgttct ggcgagcagt tttgttgatt taactgttga ggtttagggc          50

<210> SEQ ID NO 9
<211> LENGTH: 50

<212> TYPE: DNA
<213> ORGANISM: Artificial sequence
<220> FEATURE:
<223> OTHER INFORMATION: DNA Probe

<400> SEQUENCE: 9
atctaatccc agtttgggtc ttagctattg tgtgttcaga tatgttaaag         50

<210> SEQ ID NO 10
<211> LENGTH: 50
<212> TYPE: DNA
<213> ORGANISM: Artificial sequence
<220> FEATURE:
<223> OTHER INFORMATION: DNA Probe

<400> SEQUENCE: 10
attttgtgtc aactggagtt ttttacaact caggtgagtt ttagctttat         50

<210> SEQ ID NO 11
<211> LENGTH: 50
<212> TYPE: DNA
<213> ORGANISM: Artificial sequence
<220> FEATURE:
<223> OTHER INFORMATION: DNA Probe

<400> SEQUENCE: 11
ctaaaacact ctttacgccg gcttctattg acttgggtta atcgtgtgac         50

<210> SEQ ID NO 12
<211> LENGTH: 50
<212> TYPE: DNA
<213> ORGANISM: Artificial sequence
<220> FEATURE:
<223> OTHER INFORMATION: DNA Probe

<400> SEQUENCE: 12
gaaattgacc aaccctgggg ttagtatagc ttagttaaac tttcgtttat         50

<210> SEQ ID NO 13
<211> LENGTH: 50
<212> TYPE: DNA
<213> ORGANISM: Artificial sequence
<220> FEATURE:
<223> OTHER INFORMATION: DNA Probe

<400> SEQUENCE: 13
actgctgttt cccgtggggg tgtggctagg ctaagcgttt tgagctgcat         50

<210> SEQ ID NO 14
<211> LENGTH: 50
<212> TYPE: DNA
<213> ORGANISM: Artificial sequence
<220> FEATURE:
<223> OTHER INFORMATION: DNA Probe

<400> SEQUENCE: 14
gcttgtccct tttgatcgtg gtgatttaga gggtgaactc actggaacgg         50

<210> SEQ ID NO 15
<211> LENGTH: 50
<212> TYPE: DNA
<213> ORGANISM: Artificial sequence
<220> FEATURE:
<223> OTHER INFORMATION: DNA Probe

```
<400> SEQUENCE: 15
taatcttact aagagctaat agaaaggcta ggaccaaacc tatttgttta              50

<210> SEQ ID NO 16
<211> LENGTH: 50
<212> TYPE: DNA
<213> ORGANISM: Artificial sequence
<220> FEATURE:
<223> OTHER INFORMATION: DNA Probe

<400> SEQUENCE: 16
aaaccctgtt cttgggtggg tgtgggtata atactaagtt gagatgatat              50

<210> SEQ ID NO 17
<211> LENGTH: 50
<212> TYPE: DNA
<213> ORGANISM: Artificial sequence
<220> FEATURE:
<223> OTHER INFORMATION: DNA Probe

<400> SEQUENCE: 17
gcgctttgtg aagtaggcct tatttctctt gtcctttcgt acagggagga              50

<210> SEQ ID NO 18
<211> LENGTH: 50
<212> TYPE: DNA
<213> ORGANISM: Artificial sequence
<220> FEATURE:
<223> OTHER INFORMATION: DNA Probe

<400> SEQUENCE: 18
aaaccgacct ggattactcc ggtctgaact cagatcacgt aggactttaa              50

<210> SEQ ID NO 19
<211> LENGTH: 50
<212> TYPE: DNA
<213> ORGANISM: Artificial sequence
<220> FEATURE:
<223> OTHER INFORMATION: DNA Probe

<400> SEQUENCE: 19
acctttaata gcggctgcac catcgggatg tcctgatcca acatcgaggt              50

<210> SEQ ID NO 20
<211> LENGTH: 50
<212> TYPE: DNA
<213> ORGANISM: Artificial sequence
<220> FEATURE:
<223> OTHER INFORMATION: DNA Probe

<400> SEQUENCE: 20
tgatatggac tctagaatag gattgcgctg ttatccctag ggtaacttgt              50

<210> SEQ ID NO 21
<211> LENGTH: 50
<212> TYPE: DNA
<213> ORGANISM: Artificial sequence
<220> FEATURE:
<223> OTHER INFORMATION: DNA Probe

<400> SEQUENCE: 21
attggatcaa ttgagtatag tagttcgctt tgactggtga agtcttagca              50

<210> SEQ ID NO 22
```

<211> LENGTH: 50
<212> TYPE: DNA
<213> ORGANISM: Artificial sequence
<220> FEATURE:
<223> OTHER INFORMATION: DNA Probe

<400> SEQUENCE: 22
ttgggttctg ctccgaggtc gccccaaccg aaatttttaa tgcaggtttg        50

<210> SEQ ID NO 23
<211> LENGTH: 50
<212> TYPE: DNA
<213> ORGANISM: Artificial sequence
<220> FEATURE:
<223> OTHER INFORMATION: DNA Probe

<400> SEQUENCE: 23
tgggtttgtt aggtactgtt tgcattaata aattaaagct ccatagggtc        50

<210> SEQ ID NO 24
<211> LENGTH: 50
<212> TYPE: DNA
<213> ORGANISM: Artificial sequence
<220> FEATURE:
<223> OTHER INFORMATION: DNA Probe

<400> SEQUENCE: 24
gtcatgcccg cctcttcacg ggcaggtcaa tttcactggt taaaagtaag        50

<210> SEQ ID NO 25
<211> LENGTH: 50
<212> TYPE: DNA
<213> ORGANISM: Artificial sequence
<220> FEATURE:
<223> OTHER INFORMATION: DNA Probe

<400> SEQUENCE: 25
cgtggagcca ttcatacagg tccctattta aggaacaagt gattatgcta        50

<210> SEQ ID NO 26
<211> LENGTH: 50
<212> TYPE: DNA
<213> ORGANISM: Artificial sequence
<220> FEATURE:
<223> OTHER INFORMATION: DNA Probe

<400> SEQUENCE: 26
ggtaccgcgg ccgttaaaca tgtgtcactg ggcaggcggt gcctctaata        50

<210> SEQ ID NO 27
<211> LENGTH: 50
<212> TYPE: DNA
<213> ORGANISM: Artificial sequence
<220> FEATURE:
<223> OTHER INFORMATION: DNA Probe

<400> SEQUENCE: 27
gtgatgtttt tggtaaacag gcggggtaag gtttgccgag ttccttttac        50

<210> SEQ ID NO 28
<211> LENGTH: 50
<212> TYPE: DNA
<213> ORGANISM: Artificial sequence
<220> FEATURE:
<223> OTHER INFORMATION: DNA Probe

```
<400> SEQUENCE: 28
cttatgagca tgcctgtgtt gggttgacag tgagggtaat aatgacttgt            50

<210> SEQ ID NO 29
<211> LENGTH: 50
<212> TYPE: DNA
<213> ORGANISM: Artificial sequence
<220> FEATURE:
<223> OTHER INFORMATION: DNA Probe

<400> SEQUENCE: 29
attgggctgt taattgtcag ttcagtgttt tgatctgacg caggcttatg            50

<210> SEQ ID NO 30
<211> LENGTH: 50
<212> TYPE: DNA
<213> ORGANISM: Artificial sequence
<220> FEATURE:
<223> OTHER INFORMATION: DNA Probe

<400> SEQUENCE: 30
tcatgttact tatactaaca ttagttcttc tatagggtga tagattggtc            50

<210> SEQ ID NO 31
<211> LENGTH: 50
<212> TYPE: DNA
<213> ORGANISM: Artificial sequence
<220> FEATURE:
<223> OTHER INFORMATION: DNA Probe

<400> SEQUENCE: 31
agttcagtta tatgtttggg atttttagg tagtgggtgt tgagcttgaa             50

<210> SEQ ID NO 32
<211> LENGTH: 50
<212> TYPE: DNA
<213> ORGANISM: Artificial sequence
<220> FEATURE:
<223> OTHER INFORMATION: DNA Probe

<400> SEQUENCE: 32
tggctgcttt taggcctact atgggtgtta aattttttac tctctctaca            50

<210> SEQ ID NO 33
<211> LENGTH: 50
<212> TYPE: DNA
<213> ORGANISM: Artificial sequence
<220> FEATURE:
<223> OTHER INFORMATION: DNA Probe

<400> SEQUENCE: 33
gtccaaagag ctgttcctct ttggactaac agttaaattt acaaggggat            50

<210> SEQ ID NO 34
<211> LENGTH: 50
<212> TYPE: DNA
<213> ORGANISM: Artificial sequence
<220> FEATURE:
<223> OTHER INFORMATION: DNA Probe

<400> SEQUENCE: 34
ggcaaattta aagttgaact aagattctat cttggacaac cagctatcac            50

<210> SEQ ID NO 35
```

<211> LENGTH: 50
<212> TYPE: DNA
<213> ORGANISM: Artificial sequence
<220> FEATURE:
<223> OTHER INFORMATION: DNA Probe

<400> SEQUENCE: 35
tgtcgcctct acctataaat cttcccacta ttttgctaca tagacgggtg          50

<210> SEQ ID NO 36
<211> LENGTH: 50
<212> TYPE: DNA
<213> ORGANISM: Artificial sequence
<220> FEATURE:
<223> OTHER INFORMATION: DNA Probe

<400> SEQUENCE: 36
tcttaggtag ctcgtctggt ttcggggggtc ttagctttgg ctctccttgc          50

<210> SEQ ID NO 37
<211> LENGTH: 50
<212> TYPE: DNA
<213> ORGANISM: Artificial sequence
<220> FEATURE:
<223> OTHER INFORMATION: DNA Probe

<400> SEQUENCE: 37
taattcatta tgcagaaggt atagggggtta gtccttgcta tattatgctt          50

<210> SEQ ID NO 38
<211> LENGTH: 50
<212> TYPE: DNA
<213> ORGANISM: Artificial sequence
<220> FEATURE:
<223> OTHER INFORMATION: DNA Probe

<400> SEQUENCE: 38 tctttcccctt gcggtactat atctattgcg ccaggtttca atttctatcg          50

<210> SEQ ID NO 39
<211> LENGTH: 50
<212> TYPE: DNA
<213> ORGANISM: Artificial sequence
<220> FEATURE:
<223> OTHER INFORMATION: DNA Probe

<400> SEQUENCE: 39
ggtaaatggt ttggctaagg ttgtctggta gtaaggtgga gtgggtttgg          50

<210> SEQ ID NO 40
<211> LENGTH: 50
<212> TYPE: DNA
<213> ORGANISM: Artificial sequence
<220> FEATURE:
<223> OTHER INFORMATION: DNA Probe

<400> SEQUENCE: 40
taatgatcct tccgcaggtt cacctacgga aaccttgtta cgactttac          50

<210> SEQ ID NO 41
<211> LENGTH: 50
<212> TYPE: DNA
<213> ORGANISM: Artificial sequence
<220> FEATURE:
<223> OTHER INFORMATION: DNA Probe

<400> SEQUENCE: 41
aagttcgacc gtcttctcag cgctccgcca gggccgtggg ccgaccccgg         50

<210> SEQ ID NO 42
<211> LENGTH: 50
<212> TYPE: DNA
<213> ORGANISM: Artificial sequence
<220> FEATURE:
<223> OTHER INFORMATION: DNA Probe

<400> SEQUENCE: 42
ggcctcacta aaccatccaa tcggtagtag cgacgggcgg tgtgtacaaa         50

<210> SEQ ID NO 43
<211> LENGTH: 50
<212> TYPE: DNA
<213> ORGANISM: Artificial sequence
<220> FEATURE:
<223> OTHER INFORMATION: DNA Probe

<400> SEQUENCE: 43
caacgcaagc ttatgacccg cacttactcg ggaattccct cgttcatggg         50

<210> SEQ ID NO 44
<211> LENGTH: 50
<212> TYPE: DNA
<213> ORGANISM: Artificial sequence
<220> FEATURE:
<223> OTHER INFORMATION: DNA Probe

<400> SEQUENCE: 44
ccgatcccca tcacgaatgg ggttcaacgg gttacccgcg cctgccggcg         50

<210> SEQ ID NO 45
<211> LENGTH: 50
<212> TYPE: DNA
<213> ORGANISM: Artificial sequence
<220> FEATURE:
<223> OTHER INFORMATION: DNA Probe

<400> SEQUENCE: 45
ctgagccagt cagtgtagcg cgcgtgcagc cccggacatc taagggcatc         50

<210> SEQ ID NO 46
<211> LENGTH: 50
<212> TYPE: DNA
<213> ORGANISM: Artificial sequence
<220> FEATURE:
<223> OTHER INFORMATION: DNA Probe

<400> SEQUENCE: 46
ctcaatctcg ggtggctgaa cgccacttgt ccctctaaga agttggggga         50

<210> SEQ ID NO 47
<211> LENGTH: 50
<212> TYPE: DNA
<213> ORGANISM: Artificial sequence
<220> FEATURE:
<223> OTHER INFORMATION: DNA Probe

<400> SEQUENCE: 47
ggtcgcgtaa ctagttagca tgccagagtc tcgttcgtta tcggaattaa         50

<210> SEQ ID NO 48

<211> LENGTH: 50
<212> TYPE: DNA
<213> ORGANISM: Artificial sequence
<220> FEATURE:
<223> OTHER INFORMATION: DNA Probe

<400> SEQUENCE: 48
caccaactaa gaacggccat gcaccaccac ccacggaatc gagaaagagc    50

<210> SEQ ID NO 49
<211> LENGTH: 50
<212> TYPE: DNA
<213> ORGANISM: Artificial sequence
<220> FEATURE:
<223> OTHER INFORMATION: DNA Probe

<400> SEQUENCE: 49
cctgtccgtg tccgggccgg gtgaggtttc ccgtgttgag tcaaattaag    50

<210> SEQ ID NO 50
<211> LENGTH: 50
<212> TYPE: DNA
<213> ORGANISM: Artificial sequence
<220> FEATURE:
<223> OTHER INFORMATION: DNA Probe

<400> SEQUENCE: 50
ctggtggtgc ccttccgtca attcctttaa gtttcagctt tgcaaccata    50

<210> SEQ ID NO 51
<211> LENGTH: 50
<212> TYPE: DNA
<213> ORGANISM: Artificial sequence
<220> FEATURE:
<223> OTHER INFORMATION: DNA Probe

<400> SEQUENCE: 51
aaagactttg gtttcccgga agctgcccgg cgggtcatgg gaataacgcc    50

<210> SEQ ID NO 52
<211> LENGTH: 50
<212> TYPE: DNA
<213> ORGANISM: Artificial sequence
<220> FEATURE:
<223> OTHER INFORMATION: DNA Probe

<400> SEQUENCE: 52
ggcatcgttt atggtcggaa ctacgacggt atctgatcgt cttcgaacct    50

<210> SEQ ID NO 53
<211> LENGTH: 50
<212> TYPE: DNA
<213> ORGANISM: Artificial sequence
<220> FEATURE:
<223> OTHER INFORMATION: DNA Probe

<400> SEQUENCE: 53
gattaatgaa aacattcttg gcaaatgctt tcgctctggt ccgtcttgcg    50

<210> SEQ ID NO 54
<211> LENGTH: 50
<212> TYPE: DNA
<213> ORGANISM: Artificial sequence
<220> FEATURE:
<223> OTHER INFORMATION: DNA Probe

<400> SEQUENCE: 54
cacctctagc ggcgcaatac gaatgccccc ggccgtccct cttaatcatg    50

<210> SEQ ID NO 55
<211> LENGTH: 50
<212> TYPE: DNA
<213> ORGANISM: Artificial sequence
<220> FEATURE:
<223> OTHER INFORMATION: DNA Probe

<400> SEQUENCE: 55
accaacaaaa tagaaccgcg gtcctattcc attattccta gctgcggtat    50

<210> SEQ ID NO 56
<211> LENGTH: 50
<212> TYPE: DNA
<213> ORGANISM: Artificial sequence
<220> FEATURE:
<223> OTHER INFORMATION: DNA Probe

<400> SEQUENCE: 56
ctgctttgaa cactctaatt ttttcaaagt aaacgcttcg ggccccgcgg    50

<210> SEQ ID NO 57
<211> LENGTH: 50
<212> TYPE: DNA
<213> ORGANISM: Artificial sequence
<220> FEATURE:
<223> OTHER INFORMATION: DNA Probe

<400> SEQUENCE: 57
gcatcgaggg ggcgccgaga ggcaaggggc ggggacgggc ggtggctcgc    50

<210> SEQ ID NO 58
<211> LENGTH: 50
<212> TYPE: DNA
<213> ORGANISM: Artificial sequence
<220> FEATURE:
<223> OTHER INFORMATION: DNA Probe

<400> SEQUENCE: 58
ccgcccgctc ccaagatcca actacgagct ttttaactgc agcaacttta    50

<210> SEQ ID NO 59
<211> LENGTH: 50
<212> TYPE: DNA
<213> ORGANISM: Artificial sequence
<220> FEATURE:
<223> OTHER INFORMATION: DNA Probe

<400> SEQUENCE: 59
gctggaatta ccgcggctgc tggcaccaga cttgccctcc aatggatcct    50

<210> SEQ ID NO 60
<211> LENGTH: 50
<212> TYPE: DNA
<213> ORGANISM: Artificial sequence
<220> FEATURE:
<223> OTHER INFORMATION: DNA Probe

<400> SEQUENCE: 60
agtggactca ttccaattac agggcctcga aagagtcctg tattgttatt    50

<210> SEQ ID NO 61

<211> LENGTH: 50
<212> TYPE: DNA
<213> ORGANISM: Artificial sequence
<220> FEATURE:
<223> OTHER INFORMATION: DNA Probe

<400> SEQUENCE: 61
cccgggtcgg gagtgggtaa tttgcgcgcc tgctgccttc cttggatgtg         50

<210> SEQ ID NO 62
<211> LENGTH: 50
<212> TYPE: DNA
<213> ORGANISM: Artificial sequence
<220> FEATURE:
<223> OTHER INFORMATION: DNA Probe

<400> SEQUENCE: 62
gctccctctc cggaatcgaa ccctgattcc ccgtcacccg tggtcaccat         50

<210> SEQ ID NO 63
<211> LENGTH: 50
<212> TYPE: DNA
<213> ORGANISM: Artificial sequence
<220> FEATURE:
<223> OTHER INFORMATION: DNA Probe

<400> SEQUENCE: 63
taccatcgaa agttgatagg gcagacgttc gaatgggtcg tcgccgccac         50

<210> SEQ ID NO 64
<211> LENGTH: 50
<212> TYPE: DNA
<213> ORGANISM: Artificial sequence
<220> FEATURE:
<223> OTHER INFORMATION: DNA Probe

<400> SEQUENCE: 64
ggcccgaggt tatctagagt caccaaagcc gccggcgccc gcccccggc         50

<210> SEQ ID NO 65
<211> LENGTH: 50
<212> TYPE: DNA
<213> ORGANISM: Artificial sequence
<220> FEATURE:
<223> OTHER INFORMATION: DNA Probe

<400> SEQUENCE: 65
gctgaccggg ttggttttga tctgataaat gcacgcatcc ccccgcgaa         50

<210> SEQ ID NO 66
<211> LENGTH: 50
<212> TYPE: DNA
<213> ORGANISM: Artificial sequence
<220> FEATURE:
<223> OTHER INFORMATION: DNA Probe

<400> SEQUENCE: 66
tcggcatgta ttagctctag aattaccaca gttatccaag taggagagga         50

<210> SEQ ID NO 67
<211> LENGTH: 50
<212> TYPE: DNA
<213> ORGANISM: Artificial sequence
<220> FEATURE:
<223> OTHER INFORMATION: DNA Probe -continued

```
<400> SEQUENCE: 67
aaccataact gatttaatga gccattcgca gtttcactgt accggccgtg        50

<210> SEQ ID NO 68
<211> LENGTH: 50
<212> TYPE: DNA
<213> ORGANISM: Artificial sequence
<220> FEATURE:
<223> OTHER INFORMATION: DNA Probe

<400> SEQUENCE: 68
atggcttaat ctttgagaca agcatatgct actggcagga tcaaccaggt        50

<210> SEQ ID NO 69
<211> LENGTH: 50
<212> TYPE: DNA
<213> ORGANISM: Artificial sequence
<220> FEATURE:
<223> OTHER INFORMATION: DNA Probe

<400> SEQUENCE: 69
gacaaaccct tgtgtcgagg gctgactttc aatagatcgc agcgagggag        50

<210> SEQ ID NO 70
<211> LENGTH: 50
<212> TYPE: DNA
<213> ORGANISM: Artificial sequence
<220> FEATURE:
<223> OTHER INFORMATION: DNA Probe

<400> SEQUENCE: 70
cgaaaccccg acccagaagc aggtcgtcta cgaatggttt agcgccaggt        50

<210> SEQ ID NO 71
<211> LENGTH: 50
<212> TYPE: DNA
<213> ORGANISM: Artificial sequence
<220> FEATURE:
<223> OTHER INFORMATION: DNA Probe

<400> SEQUENCE: 71
ggtgcgtgac gggcgagggg gcggccgcct ttccggccgc gccccgtttc        50

<210> SEQ ID NO 72
<211> LENGTH: 50
<212> TYPE: DNA
<213> ORGANISM: Artificial sequence
<220> FEATURE:
<223> OTHER INFORMATION: DNA Probe

<400> SEQUENCE: 72
ctccgcaccg gaccccggtc ccggcgcgcg gcggggcacg cgccctcccg        50

<210> SEQ ID NO 73
<211> LENGTH: 50
<212> TYPE: DNA
<213> ORGANISM: Artificial sequence
<220> FEATURE:
<223> OTHER INFORMATION: DNA Probe

<400> SEQUENCE: 73 agggggggc ggcccgccgg cggggacagg cggggaccg gctatccgag         50

<210> SEQ ID NO 74
```

<211> LENGTH: 50
<212> TYPE: DNA
<213> ORGANISM: Artificial sequence
<220> FEATURE:
<223> OTHER INFORMATION: DNA Probe

<400> SEQUENCE: 74
gcggcgctgc cgtatcgttc gcctgggcgg gattctgact tagaggcgtt    50

<210> SEQ ID NO 75
<211> LENGTH: 50
<212> TYPE: DNA
<213> ORGANISM: Artificial sequence
<220> FEATURE:
<223> OTHER INFORMATION: DNA Probe

<400> SEQUENCE: 75
agatggtagc ttcgccccat tggctcctca gccaagcaca tacaccaaat    50

<210> SEQ ID NO 76
<211> LENGTH: 50
<212> TYPE: DNA
<213> ORGANISM: Artificial sequence
<220> FEATURE:
<223> OTHER INFORMATION: DNA Probe

<400> SEQUENCE: 76
tcctctcgta ctgagcagga ttaccatggc aacaacacat catcagtagg    50

<210> SEQ ID NO 77
<211> LENGTH: 50
<212> TYPE: DNA
<213> ORGANISM: Artificial sequence
<220> FEATURE:
<223> OTHER INFORMATION: DNA Probe

<400> SEQUENCE: 77
ctcacgacgg tctaaaccca gctcacgttc cctattagtg ggtgaacaat    50

<210> SEQ ID NO 78
<211> LENGTH: 50
<212> TYPE: DNA
<213> ORGANISM: Artificial sequence
<220> FEATURE:
<223> OTHER INFORMATION: DNA Probe

<400> SEQUENCE: 78
ttctgcttca caatgatagg aagagccgac atcgaaggat caaaaagcga    50

<210> SEQ ID NO 79
<211> LENGTH: 50
<212> TYPE: DNA
<213> ORGANISM: Artificial sequence
<220> FEATURE:
<223> OTHER INFORMATION: DNA Probe

<400> SEQUENCE: 79
ttggccgcca caagccagtt atccctgtgg taacttttct gacacctcct    50

<210> SEQ ID NO 80
<211> LENGTH: 50
<212> TYPE: DNA
<213> ORGANISM: Artificial sequence
<220> FEATURE:
<223> OTHER INFORMATION: DNA Probe

<400> SEQUENCE: 80
ggtcagaagg atcgtgaggc cccgctttca cggtctgtat tcgtactgaa                50

<210> SEQ ID NO 81
<211> LENGTH: 50
<212> TYPE: DNA
<213> ORGANISM: Artificial sequence
<220> FEATURE:
<223> OTHER INFORMATION: DNA Probe

<400> SEQUENCE: 81
agcttttgcc cttctgctcc acgggaggtt tctgtcctcc ctgagctcgc                50

<210> SEQ ID NO 82
<211> LENGTH: 50
<212> TYPE: DNA
<213> ORGANISM: Artificial sequence
<220> FEATURE:
<223> OTHER INFORMATION: DNA Probe

<400> SEQUENCE: 82
ttaccgtttg acaggtgtac cgccccagtc aaactcccca cctggcactg                50

<210> SEQ ID NO 83
<211> LENGTH: 50
<212> TYPE: DNA
<213> ORGANISM: Artificial sequence
<220> FEATURE:
<223> OTHER INFORMATION: DNA Probe

<400> SEQUENCE: 83
gcgcccggcc gggcgggcgc ttggcgccag aagcgagagc ccctcgggct                50

<210> SEQ ID NO 84
<211> LENGTH: 50
<212> TYPE: DNA
<213> ORGANISM: Artificial sequence
<220> FEATURE:
<223> OTHER INFORMATION: DNA Probe

<400> SEQUENCE: 84
ccgggtcagt gaaaaaacga tcagagtagt ggtatttcac cggcggcccg                50

<210> SEQ ID NO 85
<211> LENGTH: 50
<212> TYPE: DNA
<213> ORGANISM: Artificial sequence
<220> FEATURE:
<223> OTHER INFORMATION: DNA Probe

<400> SEQUENCE: 85
cgccccgggc ccctcgcggg gacaccgggg gggcgccggg ggcctcccac                50

<210> SEQ ID NO 86
<211> LENGTH: 50
<212> TYPE: DNA
<213> ORGANISM: Artificial sequence
<220> FEATURE:
<223> OTHER INFORMATION: DNA Probe

<400> SEQUENCE: 86
catgtctctt caccgtgcca gactagagtc aagctcaaca gggtcttctt                50

<210> SEQ ID NO 87

<211> LENGTH: 50
<212> TYPE: DNA
<213> ORGANISM: Artificial sequence
<220> FEATURE:
<223> OTHER INFORMATION: DNA Probe

<400> SEQUENCE: 87
ccaagcccgt tcccttggct gtggtttcgc tggatagtag gtagggacag        50

<210> SEQ ID NO 88
<211> LENGTH: 50
<212> TYPE: DNA
<213> ORGANISM: Artificial sequence
<220> FEATURE:
<223> OTHER INFORMATION: DNA Probe

<400> SEQUENCE: 88
tccattcatg cgcgtcacta attagatgac gaggcatttg gctaccttaa        50

<210> SEQ ID NO 89
<211> LENGTH: 50
<212> TYPE: DNA
<213> ORGANISM: Artificial sequence
<220> FEATURE:
<223> OTHER INFORMATION: DNA Probe

<400> SEQUENCE: 89
tcccgccgtt tacccgcgct tcattgaatt tcttcacttt gacattcaga        50

<210> SEQ ID NO 90
<211> LENGTH: 50
<212> TYPE: DNA
<213> ORGANISM: Artificial sequence
<220> FEATURE:
<223> OTHER INFORMATION: DNA Probe

<400> SEQUENCE: 90
cacatcgcgt caacacccgc cgcgggcctt cgcgatgctt tgttttaatt        50

<210> SEQ ID NO 91
<211> LENGTH: 50
<212> TYPE: DNA
<213> ORGANISM: Artificial sequence
<220> FEATURE:
<223> OTHER INFORMATION: DNA Probe

<400> SEQUENCE: 91
cctggtccgc accagttcta agtcggctgc taggcgccgg ccgaggcgag        50

<210> SEQ ID NO 92
<211> LENGTH: 50
<212> TYPE: DNA
<213> ORGANISM: Artificial sequence
<220> FEATURE:
<223> OTHER INFORMATION: DNA Probe

<400> SEQUENCE: 92
cggccccggg ggcggacccg gcgggggga ccggcccgcg gccsctccgc        50

<210> SEQ ID NO 93
<211> LENGTH: 50
<212> TYPE: DNA
<213> ORGANISM: Artificial sequence
<220> FEATURE:
<223> OTHER INFORMATION: DNA Probe

```
<400> SEQUENCE: 93
ccgccgcgcg ccgaggagga gggggggaacg gggggcggac ggggccgggg              50

<210> SEQ ID NO 94
<211> LENGTH: 50
<212> TYPE: DNA
<213> ORGANISM: Artificial sequence
<220> FEATURE:
<223> OTHER INFORMATION: DNA Probe

<400> SEQUENCE: 94
acgaaccgcc ccgccccgcc gcccgccgac cgccgccgcc cgaccgctcc              50

<210> SEQ ID NO 95
<211> LENGTH: 50
<212> TYPE: DNA
<213> ORGANISM: Artificial sequence
<220> FEATURE:
<223> OTHER INFORMATION: DNA Probe

<400> SEQUENCE: 95
cgcgcgcgac cgagacgtgg ggtgggggtg ggggcgcgc cgcgccgccg              50

<210> SEQ ID NO 96
<211> LENGTH: 50
<212> TYPE: DNA
<213> ORGANISM: Artificial sequence
<220> FEATURE:
<223> OTHER INFORMATION: DNA Probe

<400> SEQUENCE: 96
gcggccgcga cgcccgccgc agctggggcg atccacggga agggcccggc              50

<210> SEQ ID NO 97
<211> LENGTH: 50
<212> TYPE: DNA
<213> ORGANISM: Artificial sequence
<220> FEATURE:
<223> OTHER INFORMATION: DNA Probe

<400> SEQUENCE: 97
gcgccgccgc cggccccccg ggtccccggg gccccctcg cggggacctg              50

<210> SEQ ID NO 98
<211> LENGTH: 50
<212> TYPE: DNA
<213> ORGANISM: Artificial sequence
<220> FEATURE:
<223> OTHER INFORMATION: DNA Probe

<400> SEQUENCE: 98
ccggcggccg ccgcgcggcc cctgccgccc cgacccttct ccccccgccg              50

<210> SEQ ID NO 99
<211> LENGTH: 50
<212> TYPE: DNA
<213> ORGANISM: Artificial sequence
<220> FEATURE:
<223> OTHER INFORMATION: DNA Probe

<400> SEQUENCE: 99 ctccccccggg gagggggggag gacggggagc gggggagaga gagagagaga              50

<210> SEQ ID NO 100
```

<210> SEQ ID NO 100
<211> LENGTH: 50
<212> TYPE: DNA
<213> ORGANISM: Artificial sequence
<220> FEATURE:
<223> OTHER INFORMATION: DNA Probe

<400> SEQUENCE: 100
agggagcgag cggcgcgcgc gggtggggcg ggggagggcc gcgaggggggg    50

<210> SEQ ID NO 101
<211> LENGTH: 50
<212> TYPE: DNA
<213> ORGANISM: Artificial sequence
<220> FEATURE:
<223> OTHER INFORMATION: DNA Probe

<400> SEQUENCE: 101
gggggcgcgc gcctcgtcca gccgcggcgc gcgcccagcc ccgcttcgcg    50

<210> SEQ ID NO 102
<211> LENGTH: 50
<212> TYPE: DNA
<213> ORGANISM: Artificial sequence
<220> FEATURE:
<223> OTHER INFORMATION: DNA Probe

<400> SEQUENCE: 102 cccagcccctt agagccaatc cttatcccga agttacggat ccggcttgcc    50

<210> SEQ ID NO 103
<211> LENGTH: 50
<212> TYPE: DNA
<213> ORGANISM: Artificial sequence
<220> FEATURE:
<223> OTHER INFORMATION: DNA Probe

<400> SEQUENCE: 103
cattgttcca acatgccaga ggctgttcac cttggagacc tgctgcggat    50

<210> SEQ ID NO 104
<211> LENGTH: 50
<212> TYPE: DNA
<213> ORGANISM: Artificial sequence
<220> FEATURE:
<223> OTHER INFORMATION: DNA Probe

<400> SEQUENCE: 104
cgcgagattt acaccctctc ccccggattt tcaagggcca gcgagagctc    50

<210> SEQ ID NO 105
<211> LENGTH: 50
<212> TYPE: DNA
<213> ORGANISM: Artificial sequence
<220> FEATURE:
<223> OTHER INFORMATION: DNA Probe

<400> SEQUENCE: 105
aaccgcgacg ctttccaagg cacgggcccc tctctcgggg cgaacccatt    50

<210> SEQ ID NO 106
<211> LENGTH: 50
<212> TYPE: DNA
<213> ORGANISM: Artificial sequence
<220> FEATURE:
<223> OTHER INFORMATION: DNA Probe -continued

<400> SEQUENCE: 106
cttcacaaag aaaagagaac tctccccggg gctcccgccg gcttctccgg         50

<210> SEQ ID NO 107
<211> LENGTH: 50
<212> TYPE: DNA
<213> ORGANISM: Artificial sequence
<220> FEATURE:
<223> OTHER INFORMATION: DNA Probe

<400> SEQUENCE: 107
cgcactggac gcctcgcggc gcccatctcc gccactccgg attcggggat         50

<210> SEQ ID NO 108
<211> LENGTH: 50
<212> TYPE: DNA
<213> ORGANISM: Artificial sequence
<220> FEATURE:
<223> OTHER INFORMATION: DNA Probe

<400> SEQUENCE: 108
tttcgatcgg ccgagggcaa cggaggccat cgcccgtccc ttcggaacgg         50

<210> SEQ ID NO 109
<211> LENGTH: 50
<212> TYPE: DNA
<213> ORGANISM: Artificial sequence
<220> FEATURE:
<223> OTHER INFORMATION: DNA Probe

<400> SEQUENCE: 109
caggaccgac tgacccatgt tcaactgctg ttcacatgga acccttctcc         50

<210> SEQ ID NO 110
<211> LENGTH: 50
<212> TYPE: DNA
<213> ORGANISM: Artificial sequence
<220> FEATURE:
<223> OTHER INFORMATION: DNA Probe

<400> SEQUENCE: 110
gttctcgttt gaatatttgc tactaccacc aagatctgca cctgcggcgg         50

<210> SEQ ID NO 111
<211> LENGTH: 50
<212> TYPE: DNA
<213> ORGANISM: Artificial sequence
<220> FEATURE:
<223> OTHER INFORMATION: DNA Probe

<400> SEQUENCE: 111
cgccctaggc ttcaaggctc accgcagcgg ccctcctact cgtcgcggcg         50

<210> SEQ ID NO 112
<211> LENGTH: 50
<212> TYPE: DNA
<213> ORGANISM: Artificial sequence
<220> FEATURE:
<223> OTHER INFORMATION: DNA Probe

<400> SEQUENCE: 112
tccgggggcg gggagcgggg cgtgggcggg aggaggggag gaggcgtggg         50

<210> SEQ ID NO 113

<211> LENGTH: 50
<212> TYPE: DNA
<213> ORGANISM: Artificial sequence
<220> FEATURE:
<223> OTHER INFORMATION: DNA Probe

<400> SEQUENCE: 113
aggaccccac accccgccg ccgccgccgc cgccgccctc cgacgcacac        50

<210> SEQ ID NO 114
<211> LENGTH: 50
<212> TYPE: DNA
<213> ORGANISM: Artificial sequence
<220> FEATURE:
<223> OTHER INFORMATION: DNA Probe

<400> SEQUENCE: 114
gcgcgccgcc cccgccgctc ccgtccactc tcgactgccg gcgacggccg        50

<210> SEQ ID NO 115
<211> LENGTH: 50
<212> TYPE: DNA
<213> ORGANISM: Artificial sequence
<220> FEATURE:
<223> OTHER INFORMATION: DNA Probe

<400> SEQUENCE: 115
ctccagcgcc atccattttc agggctagtt gattcggcag gtgagttgtt        50

<210> SEQ ID NO 116
<211> LENGTH: 50
<212> TYPE: DNA
<213> ORGANISM: Artificial sequence
<220> FEATURE:
<223> OTHER INFORMATION: DNA Probe

<400> SEQUENCE: 116
gattccgact tccatggcca ccgtcctgct gtctatatca accaacacct        50

<210> SEQ ID NO 117
<211> LENGTH: 50
<212> TYPE: DNA
<213> ORGANISM: Artificial sequence
<220> FEATURE:
<223> OTHER INFORMATION: DNA Probe

<400> SEQUENCE: 117
gagcgtcggc atcgggcgcc ttaacccggc gttcggttca tcccgcagcg        50

<210> SEQ ID NO 118
<211> LENGTH: 50
<212> TYPE: DNA
<213> ORGANISM: Artificial sequence
<220> FEATURE:
<223> OTHER INFORMATION: DNA Probe

<400> SEQUENCE: 118
aaaagtggcc cactaggcac tcgcattcca cgcccggctc cacgccagcg        50

<210> SEQ ID NO 119
<211> LENGTH: 50
<212> TYPE: DNA
<213> ORGANISM: Artificial sequence
<220> FEATURE:
<223> OTHER INFORMATION: DNA Probe

<400> SEQUENCE: 119
ccatttaaag tttgagaata ggttgagatc gtttcggccc caagacctct          50

<210> SEQ ID NO 120
<211> LENGTH: 50
<212> TYPE: DNA
<213> ORGANISM: Artificial sequence
<220> FEATURE:
<223> OTHER INFORMATION: DNA Probe

<400> SEQUENCE: 120
cggataaaac tgcgtggcgg gggtgcgtcg ggtctgcgag agcgccagct          50

<210> SEQ ID NO 121
<211> LENGTH: 50
<212> TYPE: DNA
<213> ORGANISM: Artificial sequence
<220> FEATURE:
<223> OTHER INFORMATION: DNA Probe

<400> SEQUENCE: 121
tcggagggaa ccagctacta gatggttcga ttagtctttc gccctatac           50

<210> SEQ ID NO 122
<211> LENGTH: 50
<212> TYPE: DNA
<213> ORGANISM: Artificial sequence
<220> FEATURE:
<223> OTHER INFORMATION: DNA Probe

<400> SEQUENCE: 122
gatttgcacg tcaggaccgc tacggacctc caccagagtt tcctctggct          50

<210> SEQ ID NO 123
<211> LENGTH: 50
<212> TYPE: DNA
<213> ORGANISM: Artificial sequence
<220> FEATURE:
<223> OTHER INFORMATION: DNA Probe

<400> SEQUENCE: 123
atagttcacc atctttcggg tcctaacacg tgcgctcgtg ctccacctcc          50

<210> SEQ ID NO 124
<211> LENGTH: 50
<212> TYPE: DNA
<213> ORGANISM: Artificial sequence
<220> FEATURE:
<223> OTHER INFORMATION: DNA Probe

<400> SEQUENCE: 124
agacgggccg gtggtgcgcc ctcggcggac tggagaggcc tcgggatccc          50

<210> SEQ ID NO 125
<211> LENGTH: 50
<212> TYPE: DNA
<213> ORGANISM: Artificial sequence
<220> FEATURE:
<223> OTHER INFORMATION: DNA Probe

<400> SEQUENCE: 125
cgcgccggcc ttcaccttca ttgcgccacg gcggctttcg tgcgagcccc          50

<210> SEQ ID NO 126

```
<211> LENGTH: 50
<212> TYPE: DNA
<213> ORGANISM: Artificial sequence
<220> FEATURE:
<223> OTHER INFORMATION: DNA Probe

<400> SEQUENCE: 126
ttagactcct tggtccgtgt ttcaagacgg gtcgggtggg tagccgacgt          50

<210> SEQ ID NO 127
<211> LENGTH: 50
<212> TYPE: DNA
<213> ORGANISM: Artificial sequence
<220> FEATURE:
<223> OTHER INFORMATION: DNA Probe

<400> SEQUENCE: 127
gcgctcgctc cgccgtcccc ctcttcgggg gacgcgcgcg tggccccgag          50

<210> SEQ ID NO 128
<211> LENGTH: 50
<212> TYPE: DNA
<213> ORGANISM: Artificial sequence
<220> FEATURE:
<223> OTHER INFORMATION: DNA Probe

<400> SEQUENCE: 128
cccgacggcg cgacccgccc ggggcgcact ggggacagtc cgccccgccc          50

<210> SEQ ID NO 129
<211> LENGTH: 50
<212> TYPE: DNA
<213> ORGANISM: Artificial sequence
<220> FEATURE:
<223> OTHER INFORMATION: DNA Probe

<400> SEQUENCE: 129
gcaccccccc cgtcgccggg gcggggggcgc ggggaggagg ggtgggagag         50

<210> SEQ ID NO 130
<211> LENGTH: 50
<212> TYPE: DNA
<213> ORGANISM: Artificial sequence
<220> FEATURE:
<223> OTHER INFORMATION: DNA Probe

<400> SEQUENCE: 130
aggggtggcc cggccccccc acgaggagac gccggcgcgc ccccgcgggg          50

<210> SEQ ID NO 131
<211> LENGTH: 50
<212> TYPE: DNA
<213> ORGANISM: Artificial sequence
<220> FEATURE:
<223> OTHER INFORMATION: DNA Probe

<400> SEQUENCE: 131
ggggattccc cgcggggtg ggcgccggga gggggagag cgcggcgacg            50

<210> SEQ ID NO 132
<211> LENGTH: 50
<212> TYPE: DNA
<213> ORGANISM: Artificial sequence
<220> FEATURE:
<223> OTHER INFORMATION: DNA Probe
```

<400> SEQUENCE: 132
gccccgggat tcggcgagtg ctgctgccgg gggggctgta acactcgggg          50

<210> SEQ ID NO 133
<211> LENGTH: 50
<212> TYPE: DNA
<213> ORGANISM: Artificial sequence
<220> FEATURE:
<223> OTHER INFORMATION: DNA Probe

<400> SEQUENCE: 133 ccgccccgc cgccgccgcc accgccgccg ccgccgccgc cccgacccgc          50

<210> SEQ ID NO 134
<211> LENGTH: 50
<212> TYPE: DNA
<213> ORGANISM: Artificial sequence
<220> FEATURE:
<223> OTHER INFORMATION: DNA Probe

<400> SEQUENCE: 134
aggacgcggg gccggggggc ggagacgggg gaggaggagg acggacggac          50

<210> SEQ ID NO 135
<211> LENGTH: 50
<212> TYPE: DNA
<213> ORGANISM: Artificial sequence
<220> FEATURE:
<223> OTHER INFORMATION: DNA Probe

<400> SEQUENCE: 135
agccaccttc cccgccgggc cttcccagcc gtcccggagc cggtcgcggc          50

<210> SEQ ID NO 136
<211> LENGTH: 50
<212> TYPE: DNA
<213> ORGANISM: Artificial sequence
<220> FEATURE:
<223> OTHER INFORMATION: DNA Probe

<400> SEQUENCE: 136
aaatgcgccc ggcggcggcc ggtcgccggt cggggacgg tcccccgccg          50

<210> SEQ ID NO 137
<211> LENGTH: 50
<212> TYPE: DNA
<213> ORGANISM: Artificial sequence
<220> FEATURE:
<223> OTHER INFORMATION: DNA Probe

<400> SEQUENCE: 137
ccgcccgccc accccgcac ccgccggagc ccgcccctc cggggaggag          50

<210> SEQ ID NO 138
<211> LENGTH: 50
<212> TYPE: DNA
<213> ORGANISM: Artificial sequence
<220> FEATURE:
<223> OTHER INFORMATION: DNA Probe

<400> SEQUENCE: 138
gggaagggag ggcgggtgga ggggtcggga ggaacggggg gcgggaaaga          50

<210> SEQ ID NO 139

<211> LENGTH: 50
<212> TYPE: DNA
<213> ORGANISM: Artificial sequence
<220> FEATURE:
<223> OTHER INFORMATION: DNA Probe

<400> SEQUENCE: 139
acacggccgg acccgccgcc gggttgaatc ctccgggcgg actgcgcgga        50

<210> SEQ ID NO 140
<211> LENGTH: 50
<212> TYPE: DNA
<213> ORGANISM: Artificial sequence
<220> FEATURE:
<223> OTHER INFORMATION: DNA Probe

<400> SEQUENCE: 140
tcttaacggt ttcacgccct cttgaactct ctcttcaaag ttcttttcaa        50

<210> SEQ ID NO 141
<211> LENGTH: 50
<212> TYPE: DNA
<213> ORGANISM: Artificial sequence
<220> FEATURE:
<223> OTHER INFORMATION: DNA Probe

<400> SEQUENCE: 141
cttgttgact atcggtctcg tgccggtatt tagccttaga tggagtttac        50

<210> SEQ ID NO 142
<211> LENGTH: 50
<212> TYPE: DNA
<213> ORGANISM: Artificial sequence
<220> FEATURE:
<223> OTHER INFORMATION: DNA Probe

<400> SEQUENCE: 142
gcattcccaa gcaacccgac tccgggaaga cccgggcgcg cgccggccgc        50

<210> SEQ ID NO 143
<211> LENGTH: 50
<212> TYPE: DNA
<213> ORGANISM: Artificial sequence
<220> FEATURE:
<223> OTHER INFORMATION: DNA Probe

<400> SEQUENCE: 143
gtccacgggc tgggcctcga tcagaaggac ttgggccccc cacgagcggc        50

<210> SEQ ID NO 144
<211> LENGTH: 50
<212> TYPE: DNA
<213> ORGANISM: Artificial sequence
<220> FEATURE:
<223> OTHER INFORMATION: DNA Probe

<400> SEQUENCE: 144
ttccgtacgc cacatgtccc gcgccccgcg gggcggggat tcggcgctgg        50

<210> SEQ ID NO 145
<211> LENGTH: 50
<212> TYPE: DNA
<213> ORGANISM: Artificial sequence
<220> FEATURE:
<223> OTHER INFORMATION: DNA Probe

<400> SEQUENCE: 145
ctcgccgtta ctgagggaat cctggttagt ttcttttcct ccgctgacta          50

<210> SEQ ID NO 146
<211> LENGTH: 50
<212> TYPE: DNA
<213> ORGANISM: Artificial sequence
<220> FEATURE:
<223> OTHER INFORMATION: DNA Probe

<400> SEQUENCE: 146
gcgggtcgcc acgtctgatc tgaggtcgcg tctcggaggg ggacgggccg          50

<210> SEQ ID NO 147
<211> LENGTH: 50
<212> TYPE: DNA
<213> ORGANISM: Artificial sequence
<220> FEATURE:
<223> OTHER INFORMATION: DNA Probe

<400> SEQUENCE: 147
aagcgacgct cagacaggcg tagccccggg aggaacccgg ggccgcaagt          50

<210> SEQ ID NO 148
<211> LENGTH: 50
<212> TYPE: DNA
<213> ORGANISM: Artificial sequence
<220> FEATURE:
<223> OTHER INFORMATION: DNA Probe

<400> SEQUENCE: 148
gcagctagct gcgttcttca tcgacgcacg agccgagtga tccaccgcta          50

<210> SEQ ID NO 149
<211> LENGTH: 50
<212> TYPE: DNA
<213> ORGANISM: Artificial sequence
<220> FEATURE:
<223> OTHER INFORMATION: DNA Probe

<400> SEQUENCE: 149
aaagcctaca gcacccggta ttcccaggcg gtctcccatc caagtactaa          50

<210> SEQ ID NO 150
<211> LENGTH: 50
<212> TYPE: DNA
<213> ORGANISM: Artificial sequence
<220> FEATURE:
<223> OTHER INFORMATION: DNA Probe

<400> SEQUENCE: 150
ttccgagatc agacgagatc gggcgcgttc aggtggtat ggccgtagac           50

<210> SEQ ID NO 151
<211> LENGTH: 50
<212> TYPE: DNA
<213> ORGANISM: Artificial sequence
<220> FEATURE:
<223> OTHER INFORMATION: DNA Probe

<400> SEQUENCE: 151
gccgcccact cagactttat tcaaagacca cgggggtacg ggtgcaggaa          50

<210> SEQ ID NO 152

```
<211> LENGTH: 50
<212> TYPE: DNA
<213> ORGANISM: Artificial sequence
<220> FEATURE:
<223> OTHER INFORMATION: DNA Probe

<400> SEQUENCE: 152
gggggaggcc caagggcaa gaagcatggc caccgaggct ccagcttaac           50

<210> SEQ ID NO 153
<211> LENGTH: 50
<212> TYPE: DNA
<213> ORGANISM: Artificial sequence
<220> FEATURE:
<223> OTHER INFORMATION: DNA Probe

<400> SEQUENCE: 153
gcacggtgct cacagaagcc aggaacttgt ccagggaggc gtgcaccgca           50

<210> SEQ ID NO 154
<211> LENGTH: 50
<212> TYPE: DNA
<213> ORGANISM: Artificial sequence
<220> FEATURE:
<223> OTHER INFORMATION: DNA Probe

<400> SEQUENCE: 154
gggaggtggg cggccagggt caccagcagg cagtggctta ggagcttgaa           50

<210> SEQ ID NO 155
<211> LENGTH: 50
<212> TYPE: DNA
<213> ORGANISM: Artificial sequence
<220> FEATURE:
<223> OTHER INFORMATION: DNA Probe

<400> SEQUENCE: 155
ccgaagcttg tgcgcgtgca ggtcgctcag ggcggacagc gcgttgggca           50

<210> SEQ ID NO 156
<211> LENGTH: 50
<212> TYPE: DNA
<213> ORGANISM: Artificial sequence
<220> FEATURE:
<223> OTHER INFORMATION: DNA Probe

<400> SEQUENCE: 156
ccacggcgtt ggtcagcgcg tcggccacct tcttgccgtg gcccttaacc           50

<210> SEQ ID NO 157
<211> LENGTH: 50
<212> TYPE: DNA
<213> ORGANISM: Artificial sequence
<220> FEATURE:
<223> OTHER INFORMATION: DNA Probe

<400> SEQUENCE: 157
ctcaggtcga agtgcgggaa gtaggtcttg gtggtggga aggacaggaa           50

<210> SEQ ID NO 158
<211> LENGTH: 50
<212> TYPE: DNA
<213> ORGANISM: Artificial sequence
<220> FEATURE:
<223> OTHER INFORMATION: DNA Probe
```

```
<400> SEQUENCE: 158
ctccgcacca tactcgccag cgtgcgcgcc gaccttaccc caggcggcct            50

<210> SEQ ID NO 159
<211> LENGTH: 50
<212> TYPE: DNA
<213> ORGANISM: Artificial sequence
<220> FEATURE:
<223> OTHER INFORMATION: DNA Probe

<400> SEQUENCE: 159
cggcaggaga cagcaccatg gtgggttctc tctgagtctg tggggaccag            50

<210> SEQ ID NO 160
<211> LENGTH: 50
<212> TYPE: DNA
<213> ORGANISM: Artificial sequence
<220> FEATURE:
<223> OTHER INFORMATION: DNA Probe

<400> SEQUENCE: 160 gagggagga gggcccgttg ggaggcccag cgggcaggag aacggctac             50

<210> SEQ ID NO 161
<211> LENGTH: 50
<212> TYPE: DNA
<213> ORGANISM: Artificial sequence
<220> FEATURE:
<223> OTHER INFORMATION: DNA Probe

<400> SEQUENCE: 161
acggtatttg gaggtcagca cggtgctcac agaagccagg aacttgtcca            50

<210> SEQ ID NO 162
<211> LENGTH: 50
<212> TYPE: DNA
<213> ORGANISM: Artificial sequence
<220> FEATURE:
<223> OTHER INFORMATION: DNA Probe

<400> SEQUENCE: 162
caggggtgaa ctcggcgggg aggtgggcgg ccagggtcac cagcaggcag            50

<210> SEQ ID NO 163
<211> LENGTH: 50
<212> TYPE: DNA
<213> ORGANISM: Artificial sequence
<220> FEATURE:
<223> OTHER INFORMATION: DNA Probe

<400> SEQUENCE: 163
aagttgaccg ggtccacccg aagcttgtgc gcgtgcaggt cgctcagggc            50

<210> SEQ ID NO 164
<211> LENGTH: 50
<212> TYPE: DNA
<213> ORGANISM: Artificial sequence
<220> FEATURE:
<223> OTHER INFORMATION: DNA Probe

<400> SEQUENCE: 164
catgtcgtcc acgtgcgcca cggcgttggt cagcgcgtcg gccaccttct            50

<210> SEQ ID NO 165
```

```
<211> LENGTH: 50
<212> TYPE: DNA
<213> ORGANISM: Artificial sequence
<220> FEATURE:
<223> OTHER INFORMATION: DNA Probe

<400> SEQUENCE: 165
cctgggcaga gccgtggctc aggtcgaagt gcgggaagta ggtcttggtg            50

<210> SEQ ID NO 166
<211> LENGTH: 50
<212> TYPE: DNA
<213> ORGANISM: Artificial sequence
<220> FEATURE:
<223> OTHER INFORMATION: DNA Probe

<400> SEQUENCE: 166
aacatcctct ccagggcctc cgcaccatac tcgccagcgt gcgcgccgac            50

<210> SEQ ID NO 167
<211> LENGTH: 50
<212> TYPE: DNA
<213> ORGANISM: Artificial sequence
<220> FEATURE:
<223> OTHER INFORMATION: DNA Probe

<400> SEQUENCE: 167
cttgacgttg gtcttgtcgg caggagacag caccatggtg ggttctctct            50

<210> SEQ ID NO 168
<211> LENGTH: 50
<212> TYPE: DNA
<213> ORGANISM: Artificial sequence
<220> FEATURE:
<223> OTHER INFORMATION: DNA Probe

<400> SEQUENCE: 168
gcaatgaaaa taaatgtttt ttattaggca gaatccagat gctcaaggcc            50

<210> SEQ ID NO 169
<211> LENGTH: 50
<212> TYPE: DNA
<213> ORGANISM: Artificial sequence
<220> FEATURE:
<223> OTHER INFORMATION: DNA Probe

<400> SEQUENCE: 169
cagtttagta gttggactta gggaacaaag gaacctttaa tagaaattgg            50

<210> SEQ ID NO 170
<211> LENGTH: 50
<212> TYPE: DNA
<213> ORGANISM: Artificial sequence
<220> FEATURE:
<223> OTHER INFORMATION: DNA Probe

<400> SEQUENCE: 170
gcttagtgat acttgtgggc cagggcatta gccacaccag ccaccacttt            50

<210> SEQ ID NO 171
<211> LENGTH: 50
<212> TYPE: DNA
<213> ORGANISM: Artificial sequence
<220> FEATURE:
<223> OTHER INFORMATION: DNA Probe
```

<400> SEQUENCE: 171
cactggtggg gtgaattctt tgccaaagtg atgggccagc acacagacca          50

<210> SEQ ID NO 172
<211> LENGTH: 50
<212> TYPE: DNA
<213> ORGANISM: Artificial sequence
<220> FEATURE:
<223> OTHER INFORMATION: DNA Probe

<400> SEQUENCE: 172
gcctgaagtt ctcaggatcc acgtgcagct tgtcacagtg cagctcactc          50

<210> SEQ ID NO 173
<211> LENGTH: 50
<212> TYPE: DNA
<213> ORGANISM: Artificial sequence
<220> FEATURE:
<223> OTHER INFORMATION: DNA Probe

<400> SEQUENCE: 173
cccttgaggt tgtccaggtg agccaggcca tcactaaagg caccgagcac          50

<210> SEQ ID NO 174
<211> LENGTH: 50
<212> TYPE: DNA
<213> ORGANISM: Artificial sequence
<220> FEATURE:
<223> OTHER INFORMATION: DNA Probe

<400> SEQUENCE: 174
cttcacctta gggttgccca taacagcatc aggagtggac agatccccaa          50

<210> SEQ ID NO 175
<211> LENGTH: 50
<212> TYPE: DNA
<213> ORGANISM: Artificial sequence
<220> FEATURE:
<223> OTHER INFORMATION: DNA Probe

<400> SEQUENCE: 175
tctgggtcca agggtagacc accagcagcc tgcccagggc ctcaccacca          50

<210> SEQ ID NO 176
<211> LENGTH: 50
<212> TYPE: DNA
<213> ORGANISM: Artificial sequence
<220> FEATURE:
<223> OTHER INFORMATION: DNA Probe

<400> SEQUENCE: 176
accttgcccc acagggcagt aacggcagac ttctcctcag gagtcagatg          50

<210> SEQ ID NO 177
<211> LENGTH: 50
<212> TYPE: DNA
<213> ORGANISM: Artificial sequence
<220> FEATURE:
<223> OTHER INFORMATION: DNA Probe

<400> SEQUENCE: 177
gtgatctctc agcagaatag atttattatt tgtattgctt gcagaataaa          50

<210> SEQ ID NO 178

```
<211> LENGTH: 50
<212> TYPE: DNA
<213> ORGANISM: Artificial sequence
<220> FEATURE:
<223> OTHER INFORMATION: DNA Probe

<400> SEQUENCE: 178
ctctgaatca tgggcagtga gctcagtggt atctggagga cagggcactg          50

<210> SEQ ID NO 179
<211> LENGTH: 50
<212> TYPE: DNA
<213> ORGANISM: Artificial sequence
<220> FEATURE:
<223> OTHER INFORMATION: DNA Probe

<400> SEQUENCE: 179
atcttctgcc aggaagcctg cacctcaggg gtgaattctt tgccgaaatg          50

<210> SEQ ID NO 180
<211> LENGTH: 50
<212> TYPE: DNA
<213> ORGANISM: Artificial sequence
<220> FEATURE:
<223> OTHER INFORMATION: DNA Probe

<400> SEQUENCE: 180
caccagcaca tttcccagga gcttgaagtt ctcaggatcc acatgcagct          50

<210> SEQ ID NO 181
<211> LENGTH: 50
<212> TYPE: DNA
<213> ORGANISM: Artificial sequence
<220> FEATURE:
<223> OTHER INFORMATION: DNA Probe

<400> SEQUENCE: 181
cactcagctg ggcaaaggtg cccttgagat catccaggtg ctttgtggca          50

<210> SEQ ID NO 182
<211> LENGTH: 50
<212> TYPE: DNA
<213> ORGANISM: Artificial sequence
<220> FEATURE:
<223> OTHER INFORMATION: DNA Probe

<400> SEQUENCE: 182
agcaccttct tgccatgtgc cttgactttg gggttgccca tgatggcaga          50

<210> SEQ ID NO 183
<211> LENGTH: 50
<212> TYPE: DNA
<213> ORGANISM: Artificial sequence
<220> FEATURE:
<223> OTHER INFORMATION: DNA Probe

<400> SEQUENCE: 183
gccaaagctg tcaaagaacc tctgggtcca tgggtagaca accaggagcc          50

<210> SEQ ID NO 184
<211> LENGTH: 50
<212> TYPE: DNA
<213> ORGANISM: Artificial sequence
<220> FEATURE:
<223> OTHER INFORMATION: DNA Probe
```

<400> SEQUENCE: 184
ctccagcatc ttccacattc accttgcccc acaggcttgt gatagtagcc      50

<210> SEQ ID NO 185
<211> LENGTH: 50
<212> TYPE: DNA
<213> ORGANISM: Artificial sequence
<220> FEATURE:
<223> OTHER INFORMATION: DNA Probe

<400> SEQUENCE: 185
aaatgaccca tggcgtctgg actaggagct tattgataac ctcagacgtt      50

<210> SEQ ID NO 186
<211> LENGTH: 50
<212> TYPE: DNA
<213> ORGANISM: Artificial sequence
<220> FEATURE:
<223> OTHER INFORMATION: DNA Probe

<400> SEQUENCE: 186
gtgatctctt agcagaatag atttattatt tgattgcttg cagaataaag      50

<210> SEQ ID NO 187
<211> LENGTH: 50
<212> TYPE: DNA
<213> ORGANISM: Artificial sequence
<220> FEATURE:
<223> OTHER INFORMATION: DNA Probe

<400> SEQUENCE: 187
tctgcatcat gggcagtgag ctcagtggta tctggaggac agggcactgg      50

<210> SEQ ID NO 188
<211> LENGTH: 50
<212> TYPE: DNA
<213> ORGANISM: Artificial sequence
<220> FEATURE:
<223> OTHER INFORMATION: DNA Probe

<400> SEQUENCE: 188
tcttctgcca ggaagcctgc acctcagggg tgaattcttt gccgaaatgg      50

<210> SEQ ID NO 189
<211> LENGTH: 50
<212> TYPE: DNA
<213> ORGANISM: Artificial sequence
<220> FEATURE:
<223> OTHER INFORMATION: DNA Probe

<400> SEQUENCE: 189
accagcacat ttcccaggag cttgaagttc tcaggatcca catgcagctt      50

<210> SEQ ID NO 190
<211> LENGTH: 50
<212> TYPE: DNA
<213> ORGANISM: Artificial sequence
<220> FEATURE:
<223> OTHER INFORMATION: DNA Probe

<400> SEQUENCE: 190
actcagctgg gcaaaggtgc ccttgagatc atccaggtgc tttatggcat      50

<210> SEQ ID NO 191

```
<211> LENGTH: 50
<212> TYPE: DNA
<213> ORGANISM: Artificial sequence
<220> FEATURE:
<223> OTHER INFORMATION: DNA Probe

<400> SEQUENCE: 191
gcaccttctt gccatgtgcc ttgactttgg ggttgcccat gatggcagag          50

<210> SEQ ID NO 192
<211> LENGTH: 50
<212> TYPE: DNA
<213> ORGANISM: Artificial sequence
<220> FEATURE:
<223> OTHER INFORMATION: DNA Probe

<400> SEQUENCE: 192
ccaaagctgt caaagaacct ctgggtccat gggtagacaa ccaggagcct          50

<210> SEQ ID NO 193
<211> LENGTH: 50
<212> TYPE: DNA
<213> ORGANISM: Artificial sequence
<220> FEATURE:
<223> OTHER INFORMATION: DNA Probe

<400> SEQUENCE: 193
tccagcatct tccacattca ccttgcccca caggcttgtg atagtagcct          50

<210> SEQ ID NO 194
<211> LENGTH: 50
<212> TYPE: DNA
<213> ORGANISM: Artificial sequence
<220> FEATURE:
<223> OTHER INFORMATION: DNA Probe

<400> SEQUENCE: 194
aatgacccat ggcgtctgga ctaggagctt attgataacc tcagacgttc          50

<210> SEQ ID NO 195
<211> LENGTH: 50
<212> TYPE: DNA
<213> ORGANISM: Artificial sequence
<220> FEATURE:
<223> OTHER INFORMATION: DNA Probe

<400> SEQUENCE: 195
atgcctggca gttccctact ctcgcatggg gagaccccac actaccatcg          50

<210> SEQ ID NO 196
<211> LENGTH: 50
<212> TYPE: DNA
<213> ORGANISM: Artificial sequence
<220> FEATURE:
<223> OTHER INFORMATION: DNA Probe

<400> SEQUENCE: 196
acttctgagt tcggcatggg gtcaggtggg accaccgcgc tacggccgcc          50

<210> SEQ ID NO 197
<211> LENGTH: 50
<212> TYPE: DNA
<213> ORGANISM: Artificial sequence
<220> FEATURE:
<223> OTHER INFORMATION: DNA Probe
```

<400> SEQUENCE: 197
ggttaccttg ttacgacttc accccagtca tgaatcacaa agtggtaagt        50

<210> SEQ ID NO 198
<211> LENGTH: 50
<212> TYPE: DNA
<213> ORGANISM: Artificial sequence
<220> FEATURE:
<223> OTHER INFORMATION: DNA Probe

<400> SEQUENCE: 198
aagctaccta cttcttttgc aacccactcc catggtgtga cgggcggtgt        50

<210> SEQ ID NO 199
<211> LENGTH: 50
<212> TYPE: DNA
<213> ORGANISM: Artificial sequence
<220> FEATURE:
<223> OTHER INFORMATION: DNA Probe

<400> SEQUENCE: 199
acgtattcac cgtggcattc tgatccacga ttactagcga ttccgacttc        50

<210> SEQ ID NO 200
<211> LENGTH: 50
<212> TYPE: DNA
<213> ORGANISM: Artificial sequence
<220> FEATURE:
<223> OTHER INFORMATION: DNA Probe

<400> SEQUENCE: 200
agactccaat ccggactacg acgcacttta tgaggtccgc ttgctctcgc        50

<210> SEQ ID NO 201
<211> LENGTH: 50
<212> TYPE: DNA
<213> ORGANISM: Artificial sequence
<220> FEATURE:
<223> OTHER INFORMATION: DNA Probe

<400> SEQUENCE: 201
tgtatgcgcc attgtagcac gtgtgtagcc ctggtcgtaa gggccatgat        50

<210> SEQ ID NO 202
<211> LENGTH: 50
<212> TYPE: DNA
<213> ORGANISM: Artificial sequence
<220> FEATURE:
<223> OTHER INFORMATION: DNA Probe

<400> SEQUENCE: 202
ccaccttcct ccagtttatc actggcagtc tcctttgagt tcccggccgg        50

<210> SEQ ID NO 203
<211> LENGTH: 50
<212> TYPE: DNA
<213> ORGANISM: Artificial sequence
<220> FEATURE:
<223> OTHER INFORMATION: DNA Probe

<400> SEQUENCE: 203
ggataagggt tgcgctcgtt gcgggactta acccaacatt tcacaacacg        50

<210> SEQ ID NO 204

<211> LENGTH: 50
<212> TYPE: DNA
<213> ORGANISM: Artificial sequence
<220> FEATURE:
<223> OTHER INFORMATION: DNA Probe

<400> SEQUENCE: 204
tgcagcacct gtctcacggt tcccgaaggc acattctcat ctctgaaaac        50

<210> SEQ ID NO 205
<211> LENGTH: 50
<212> TYPE: DNA
<213> ORGANISM: Artificial sequence
<220> FEATURE:
<223> OTHER INFORMATION: DNA Probe

<400> SEQUENCE: 205
gaccaggtaa ggttcttcgc gttgcatcga attaaaccac atgctccacc        50

<210> SEQ ID NO 206
<211> LENGTH: 50
<212> TYPE: DNA
<213> ORGANISM: Artificial sequence
<220> FEATURE:
<223> OTHER INFORMATION: DNA Probe

<400> SEQUENCE: 206
cgtcaattca tttgagtttt aaccttgcgg ccgtactccc caggcggtcg        50

<210> SEQ ID NO 207
<211> LENGTH: 50
<212> TYPE: DNA
<213> ORGANISM: Artificial sequence
<220> FEATURE:
<223> OTHER INFORMATION: DNA Probe

<400> SEQUENCE: 207
tccggaagcc acgcctcaag ggcacaacct ccaagtcgac atcgtttacg        50

<210> SEQ ID NO 208
<211> LENGTH: 50
<212> TYPE: DNA
<213> ORGANISM: Artificial sequence
<220> FEATURE:
<223> OTHER INFORMATION: DNA Probe

<400> SEQUENCE: 208
gtatctaatc ctgtttgctc cccacgcttt cgcactgagc gtcagtcttc        50

<210> SEQ ID NO 209
<211> LENGTH: 50
<212> TYPE: DNA
<213> ORGANISM: Artificial sequence
<220> FEATURE:
<223> OTHER INFORMATION: DNA Probe

<400> SEQUENCE: 209
ttcgccaccg gtattcctcc agatctctac gcatttcacc gctacacctg        50

<210> SEQ ID NO 210
<211> LENGTH: 50
<212> TYPE: DNA
<213> ORGANISM: Artificial sequence
<220> FEATURE:
<223> OTHER INFORMATION: DNA Probe

<400> SEQUENCE: 210
ctacgagact caagcttgcc agtatcagat gcagttccca ggttgagccc            50

<210> SEQ ID NO 211
<211> LENGTH: 50
<212> TYPE: DNA
<213> ORGANISM: Artificial sequence
<220> FEATURE:
<223> OTHER INFORMATION: DNA Probe

<400> SEQUENCE: 211
gacttaacaa accgcctgcg tgcgctttac gcccagtaat tccgattaac            50

<210> SEQ ID NO 212
<211> LENGTH: 50
<212> TYPE: DNA
<213> ORGANISM: Artificial sequence
<220> FEATURE:
<223> OTHER INFORMATION: DNA Probe

<400> SEQUENCE: 212
attaccgcgg ctgctggcac ggagttagcc ggtgcttctt ctgcgggtaa            50

<210> SEQ ID NO 213
<211> LENGTH: 50
<212> TYPE: DNA
<213> ORGANISM: Artificial sequence
<220> FEATURE:
<223> OTHER INFORMATION: DNA Probe

<400> SEQUENCE: 213
gtattaactt tactcccttc ctccccgctg aaagtacttt acaacccgaa            50

<210> SEQ ID NO 214
<211> LENGTH: 50
<212> TYPE: DNA
<213> ORGANISM: Artificial sequence
<220> FEATURE:
<223> OTHER INFORMATION: DNA Probe

<400> SEQUENCE: 214
cgcggcatgg ctgcatcagg cttgcgccca ttgtgcagta ttccccactg            50

<210> SEQ ID NO 215
<211> LENGTH: 50
<212> TYPE: DNA
<213> ORGANISM: Artificial sequence
<220> FEATURE:
<223> OTHER INFORMATION: DNA Probe

<400> SEQUENCE: 215
gtctggaccg tgtctcagtt ccagtgtggc tggtcatcct ctcagaccag            50

<210> SEQ ID NO 216
<211> LENGTH: 50
<212> TYPE: DNA
<213> ORGANISM: Artificial sequence
<220> FEATURE:
<223> OTHER INFORMATION: DNA Probe

<400> SEQUENCE: 216
taggtgagcc gttaccccac ctactagcta atcccatctg ggcacatccg            50

<210> SEQ ID NO 217

<210> SEQ ID NO 217
<211> LENGTH: 50
<212> TYPE: DNA
<213> ORGANISM: Artificial sequence
<220> FEATURE:
<223> OTHER INFORMATION: DNA Probe

<400> SEQUENCE: 217
aaggtccccc tctttggtct tgcgacgtta tgcggtatta gctaccgttt          50

<210> SEQ ID NO 218
<211> LENGTH: 50
<212> TYPE: DNA
<213> ORGANISM: Artificial sequence
<220> FEATURE:
<223> OTHER INFORMATION: DNA Probe

<400> SEQUENCE: 218
ctccatcagg cagtttccca gacattactc acccgtccgc cactcgtcag          50

<210> SEQ ID NO 219
<211> LENGTH: 50
<212> TYPE: DNA
<213> ORGANISM: Artificial sequence
<220> FEATURE:
<223> OTHER INFORMATION: DNA Probe

<400> SEQUENCE: 219
aaggttaagc ctcacggttc attagtaccg gttagctcaa cgcatcgctg          50

<210> SEQ ID NO 220
<211> LENGTH: 50
<212> TYPE: DNA
<213> ORGANISM: Artificial sequence
<220> FEATURE:
<223> OTHER INFORMATION: DNA Probe

<400> SEQUENCE: 220
cctatcaacg tcgtcgtctt caacgttcct tcaggaccct taaagggtca          50

<210> SEQ ID NO 221
<211> LENGTH: 50
<212> TYPE: DNA
<213> ORGANISM: Artificial sequence
<220> FEATURE:
<223> OTHER INFORMATION: DNA Probe

<400> SEQUENCE: 221
ggggcaagtt tcgtgcttag atgctttcag cacttatctc ttccgcattt          50

<210> SEQ ID NO 222
<211> LENGTH: 50
<212> TYPE: DNA
<213> ORGANISM: Artificial sequence
<220> FEATURE:
<223> OTHER INFORMATION: DNA Probe

<400> SEQUENCE: 222
ccattggcat gacaacccga acaccagtga tgcgtccact ccggtcctct          50

<210> SEQ ID NO 223
<211> LENGTH: 50
<212> TYPE: DNA
<213> ORGANISM: Artificial sequence
<220> FEATURE:
<223> OTHER INFORMATION: DNA Probe

<400> SEQUENCE: 223 cccctcagt tctccagcgc ccacggcaga tagggaccga actgtctcac        50

<210> SEQ ID NO 224
<211> LENGTH: 50
<212> TYPE: DNA
<213> ORGANISM: Artificial sequence
<220> FEATURE:
<223> OTHER INFORMATION: DNA Probe

<400> SEQUENCE: 224
gctcgcgtac cactttaaat ggcgaacagc catacccttg ggacctactt        50

<210> SEQ ID NO 225
<211> LENGTH: 50
<212> TYPE: DNA
<213> ORGANISM: Artificial sequence
<220> FEATURE:
<223> OTHER INFORMATION: DNA Probe

<400> SEQUENCE: 225
atgagccgac atcgaggtgc caaacaccgc cgtcgatatg aactcttggg        50

<210> SEQ ID NO 226
<211> LENGTH: 50
<212> TYPE: DNA
<213> ORGANISM: Artificial sequence
<220> FEATURE:
<223> OTHER INFORMATION: DNA Probe

<400> SEQUENCE: 226
atccccggag tacctttat ccgttgagcg atggcccttc cattcagaac         50

<210> SEQ ID NO 227
<211> LENGTH: 50
<212> TYPE: DNA
<213> ORGANISM: Artificial sequence
<220> FEATURE:
<223> OTHER INFORMATION: DNA Probe

<400> SEQUENCE: 227
acctgctttc gcacctgctc gcgccgtcac gctcgcagtc aagctggctt        50

<210> SEQ ID NO 228
<211> LENGTH: 50
<212> TYPE: DNA
<213> ORGANISM: Artificial sequence
<220> FEATURE:
<223> OTHER INFORMATION: DNA Probe

<400> SEQUENCE: 228
cctcctgatg tccgaccagg attagccaac cttcgtgctc ctccgttact        50

<210> SEQ ID NO 229
<211> LENGTH: 50
<212> TYPE: DNA
<213> ORGANISM: Artificial sequence
<220> FEATURE:
<223> OTHER INFORMATION: DNA Probe

<400> SEQUENCE: 229
gccccagtca aactacccac cagacactgt ccgcaacccg gattacgggt        50

<210> SEQ ID NO 230

-continued

```
<211> LENGTH: 50
<212> TYPE: DNA
<213> ORGANISM: Artificial sequence
<220> FEATURE:
<223> OTHER INFORMATION: DNA Probe

<400> SEQUENCE: 230
aaacattaaa gggtggtatt tcaaggtcgg ctccatgcag actggcgtcc         50

<210> SEQ ID NO 231
<211> LENGTH: 50
<212> TYPE: DNA
<213> ORGANISM: Artificial sequence
<220> FEATURE:
<223> OTHER INFORMATION: DNA Probe

<400> SEQUENCE: 231
ccacctatcc tacacatcaa ggctcaatgt tcagtgtcaa gctatagtaa         50

<210> SEQ ID NO 232
<211> LENGTH: 50
<212> TYPE: DNA
<213> ORGANISM: Artificial sequence
<220> FEATURE:
<223> OTHER INFORMATION: DNA Probe

<400> SEQUENCE: 232
ttccgtcttg ccgcgggtac actgcatctt cacagcgagt tcaatttcac         50

<210> SEQ ID NO 233
<211> LENGTH: 50
<212> TYPE: DNA
<213> ORGANISM: Artificial sequence
<220> FEATURE:
<223> OTHER INFORMATION: DNA Probe

<400> SEQUENCE: 233
gacagcctgg ccatcattac gccattcgtg caggtcggaa cttacccgac         50

<210> SEQ ID NO 234
<211> LENGTH: 50
<212> TYPE: DNA
<213> ORGANISM: Artificial sequence
<220> FEATURE:
<223> OTHER INFORMATION: DNA Probe

<400> SEQUENCE: 234
cttaggaccg ttatagttac ggccgccgtt taccggggct tcgatcaaga         50

<210> SEQ ID NO 235
<211> LENGTH: 50
<212> TYPE: DNA
<213> ORGANISM: Artificial sequence
<220> FEATURE:
<223> OTHER INFORMATION: DNA Probe

<400> SEQUENCE: 235
accccatcaa ttaaccttcc ggcaccgggc aggcgtcaca ccgtatacgt         50

<210> SEQ ID NO 236
<211> LENGTH: 50
<212> TYPE: DNA
<213> ORGANISM: Artificial sequence
<220> FEATURE:
<223> OTHER INFORMATION: DNA Probe
```

-continued

<400> SEQUENCE: 236
cacagtgctg tgtttttaat aaacagttgc agccagctgg tatcttcgac    50

<210> SEQ ID NO 237
<211> LENGTH: 50
<212> TYPE: DNA
<213> ORGANISM: Artificial sequence
<220> FEATURE:
<223> OTHER INFORMATION: DNA Probe

<400> SEQUENCE: 237
ccgcgaggga cctcacctac atatcagcgt gccttctccc gaagttacgg    50

<210> SEQ ID NO 238
<211> LENGTH: 50
<212> TYPE: DNA
<213> ORGANISM: Artificial sequence
<220> FEATURE:
<223> OTHER INFORMATION: DNA Probe

<400> SEQUENCE: 238
ttccttcacc cgagttctct caagcgcctt ggtattctct acctgaccac    50

<210> SEQ ID NO 239
<211> LENGTH: 50
<212> TYPE: DNA
<213> ORGANISM: Artificial sequence
<220> FEATURE:
<223> OTHER INFORMATION: DNA Probe

<400> SEQUENCE: 239
gtacgatttg atgttacctg atgcttagag gcttttcctg aagcagggc    50

<210> SEQ ID NO 240
<211> LENGTH: 50
<212> TYPE: DNA
<213> ORGANISM: Artificial sequence
<220> FEATURE:
<223> OTHER INFORMATION: DNA Probe

<400> SEQUENCE: 240
accgtagtgc ctcgtcatca cgcctcagcc ttgattttcc ggatttgcct    50

<210> SEQ ID NO 241
<211> LENGTH: 50
<212> TYPE: DNA
<213> ORGANISM: Artificial sequence
<220> FEATURE:
<223> OTHER INFORMATION: DNA Probe

<400> SEQUENCE: 241
acgcttaaac cgggacaacc gtcgcccggc caacatagcc ttctccgtcc    50

<210> SEQ ID NO 242
<211> LENGTH: 50
<212> TYPE: DNA
<213> ORGANISM: Artificial sequence
<220> FEATURE:
<223> OTHER INFORMATION: DNA Probe

<400> SEQUENCE: 242
accaagtaca ggaatattaa cctgtttccc atcgactacg cctttcggcc    50

<210> SEQ ID NO 243

```
<211> LENGTH: 50
<212> TYPE: DNA
<213> ORGANISM: Artificial sequence
<220> FEATURE:
<223> OTHER INFORMATION: DNA Probe

<400> SEQUENCE: 243
actcaccctg ccccgattaa cgttggacag gaacccttgg tcttccggcg                50

<210> SEQ ID NO 244
<211> LENGTH: 50
<212> TYPE: DNA
<213> ORGANISM: Artificial sequence
<220> FEATURE:
<223> OTHER INFORMATION: DNA Probe

<400> SEQUENCE: 244
cgctttatcg ttacttatgt cagcattcgc acttctgata cctccagcat                50

<210> SEQ ID NO 245
<211> LENGTH: 50
<212> TYPE: DNA
<213> ORGANISM: Artificial sequence
<220> FEATURE:
<223> OTHER INFORMATION: DNA Probe

<400> SEQUENCE: 245
ttcgcaggct tacagaacgc tcccctaccc aacaacgcat aagcgtcgct                50

<210> SEQ ID NO 246
<211> LENGTH: 50
<212> TYPE: DNA
<213> ORGANISM: Artificial sequence
<220> FEATURE:
<223> OTHER INFORMATION: DNA Probe

<400> SEQUENCE: 246
catggtttag ccccgttaca tcttccgcgc aggccgactc gaccagtgag                50

<210> SEQ ID NO 247
<211> LENGTH: 50
<212> TYPE: DNA
<213> ORGANISM: Artificial sequence
<220> FEATURE:
<223> OTHER INFORMATION: DNA Probe

<400> SEQUENCE: 247
taaatgatgg ctgcttctaa gccaacatcc tggctgtctg ggccttccca                50

<210> SEQ ID NO 248
<211> LENGTH: 50
<212> TYPE: DNA
<213> ORGANISM: Artificial sequence
<220> FEATURE:
<223> OTHER INFORMATION: DNA Probe

<400> SEQUENCE: 248
aaccatgact ttgggacctt agctggcggt ctgggttgtt tccctcttca                50

<210> SEQ ID NO 249
<211> LENGTH: 50
<212> TYPE: DNA
<213> ORGANISM: Artificial sequence
<220> FEATURE:
<223> OTHER INFORMATION: DNA Probe
```

<400> SEQUENCE: 249
cccgccgtgt gtctcccgtg ataacattct ccggtattcg cagtttgcat    50

<210> SEQ ID NO 250
<211> LENGTH: 50
<212> TYPE: DNA
<213> ORGANISM: Artificial sequence
<220> FEATURE:
<223> OTHER INFORMATION: DNA Probe

<400> SEQUENCE: 250
ggatgacccc cttgccgaaa cagtgctcta cccccggaga tgaattcacg    50

<210> SEQ ID NO 251
<211> LENGTH: 50
<212> TYPE: DNA
<213> ORGANISM: Artificial sequence
<220> FEATURE:
<223> OTHER INFORMATION: DNA Probe

<400> SEQUENCE: 251
agctttcggg gagaaccagc tatctcccgg tttgattggc ctttcacccc    50

<210> SEQ ID NO 252
<211> LENGTH: 50
<212> TYPE: DNA
<213> ORGANISM: Artificial sequence
<220> FEATURE:
<223> OTHER INFORMATION: DNA Probe

<400> SEQUENCE: 252
cgctaatttt tcaacattag tcggttcggt cctccagtta gtgttaccca    50

<210> SEQ ID NO 253
<211> LENGTH: 50
<212> TYPE: DNA
<213> ORGANISM: Artificial sequence
<220> FEATURE:
<223> OTHER INFORMATION: DNA Probe

<400> SEQUENCE: 253
atggctagat caccgggttt cgggtctata ccctgcaact taacgcccag    50

<210> SEQ ID NO 254
<211> LENGTH: 50
<212> TYPE: DNA
<213> ORGANISM: Artificial sequence
<220> FEATURE:
<223> OTHER INFORMATION: DNA Probe

<400> SEQUENCE: 254
ccttcggctc ccctattcgg ttaaccttgc tacagaatat aagtcgctga    50

<210> SEQ ID NO 255
<211> LENGTH: 50
<212> TYPE: DNA
<213> ORGANISM: Artificial sequence
<220> FEATURE:
<223> OTHER INFORMATION: DNA Probe

<400> SEQUENCE: 255
gtacgcagtc acacgcctaa gcgtgctccc actgcttgta cgtacacggt    50

<210> SEQ ID NO 256

```
<211> LENGTH: 50
<212> TYPE: DNA
<213> ORGANISM: Artificial sequence
<220> FEATURE:
<223> OTHER INFORMATION: DNA Probe

<400> SEQUENCE: 256
actcccctcg ccggggttct tttcgccttt ccctcacggt actggttcac                50

<210> SEQ ID NO 257
<211> LENGTH: 50
<212> TYPE: DNA
<213> ORGANISM: Artificial sequence
<220> FEATURE:
<223> OTHER INFORMATION: DNA Probe

<400> SEQUENCE: 257
agtatttagc cttggaggat ggtccccca tattcagaca ggataccacg                 50

<210> SEQ ID NO 258
<211> LENGTH: 50
<212> TYPE: DNA
<213> ORGANISM: Artificial sequence
<220> FEATURE:
<223> OTHER INFORMATION: DNA Probe

<400> SEQUENCE: 258
atcgagctca cagcatgtgc attttgtgt acggggctgt caccctgtat                 50

<210> SEQ ID NO 259
<211> LENGTH: 50
<212> TYPE: DNA
<213> ORGANISM: Artificial sequence
<220> FEATURE:
<223> OTHER INFORMATION: DNA Probe

<400> SEQUENCE: 259
acgcttccac taacacacac actgattcag gctctgggct gctcccgtt                 50

<210> SEQ ID NO 260
<211> LENGTH: 50
<212> TYPE: DNA
<213> ORGANISM: Artificial sequence
<220> FEATURE:
<223> OTHER INFORMATION: DNA Probe

<400> SEQUENCE: 260
ggggaatctc ggttgatttc ttttcctcgg ggtacttaga tgtttcagtt                50

<210> SEQ ID NO 261
<211> LENGTH: 50
<212> TYPE: DNA
<213> ORGANISM: Artificial sequence
<220> FEATURE:
<223> OTHER INFORMATION: DNA Probe

<400> SEQUENCE: 261
attaacctat ggattcagtt aatgatagtg tgtcgaaaca cactgggttt                50

<210> SEQ ID NO 262
<211> LENGTH: 50
<212> TYPE: DNA
<213> ORGANISM: Artificial sequence
<220> FEATURE:
<223> OTHER INFORMATION: DNA Probe
```

<400> SEQUENCE: 262
gccggttata acggttcata tcaccttacc gacgcttatc gcagattagc  50

<210> SEQ ID NO 263
<211> LENGTH: 50
<212> TYPE: DNA
<213> ORGANISM: Artificial sequence
<220> FEATURE:
<223> OTHER INFORMATION: DNA Probe

<400> SEQUENCE: 263
gcttggcggc gtcctactct cacaggggga aaccccgac taccatcggc  50

<210> SEQ ID NO 264
<211> LENGTH: 50
<212> TYPE: DNA
<213> ORGANISM: Artificial sequence
<220> FEATURE:
<223> OTHER INFORMATION: DNA Probe

<400> SEQUENCE: 264
ttccgtgttc ggtatgggaa cgggtgtgac ctcttcgcta tcgccaccaa  50

<210> SEQ ID NO 265
<211> LENGTH: 50
<212> TYPE: DNA
<213> ORGANISM: Artificial sequence
<220> FEATURE:
<223> OTHER INFORMATION: DNA Probe

<400> SEQUENCE: 265
tagaaaggag gtgatccagc cgcaccttcc gatacggcta ccttgttacg  50

<210> SEQ ID NO 266
<211> LENGTH: 50
<212> TYPE: DNA
<213> ORGANISM: Artificial sequence
<220> FEATURE:
<223> OTHER INFORMATION: DNA Probe

<400> SEQUENCE: 266
tctgtcccac cttcggcggc tggctcctaa aaggttacct caccgacttc  50

<210> SEQ ID NO 267
<211> LENGTH: 50
<212> TYPE: DNA
<213> ORGANISM: Artificial sequence
<220> FEATURE:
<223> OTHER INFORMATION: DNA Probe

<400> SEQUENCE: 267
tcgtggtgtg acgggcggtg tgtacaaggc ccgggaacgt attcaccgcg  50

<210> SEQ ID NO 268
<211> LENGTH: 50
<212> TYPE: DNA
<213> ORGANISM: Artificial sequence
<220> FEATURE:
<223> OTHER INFORMATION: DNA Probe

<400> SEQUENCE: 268
attactagcg attccagctt cacgcagtcg agttgcagac tgcgatccga  50

<210> SEQ ID NO 269

```
<211> LENGTH: 50
<212> TYPE: DNA
<213> ORGANISM: Artificial sequence
<220> FEATURE:
<223> OTHER INFORMATION: DNA Probe

<400> SEQUENCE: 269
gtgggattgg cttaacctcg cggtttcgct gcccttttgtt ctgtccattg      50

<210> SEQ ID NO 270
<211> LENGTH: 50
<212> TYPE: DNA
<213> ORGANISM: Artificial sequence
<220> FEATURE:
<223> OTHER INFORMATION: DNA Probe

<400> SEQUENCE: 270
ccaggtcata aggggcatga tgatttgacg tcatccccac cttcctccgg      50

<210> SEQ ID NO 271
<211> LENGTH: 50
<212> TYPE: DNA
<213> ORGANISM: Artificial sequence
<220> FEATURE:
<223> OTHER INFORMATION: DNA Probe

<400> SEQUENCE: 271
caccttagag tgcccaactg aatgctggca actaagatca agggttgcgc      50

<210> SEQ ID NO 272
<211> LENGTH: 50
<212> TYPE: DNA
<213> ORGANISM: Artificial sequence
<220> FEATURE:
<223> OTHER INFORMATION: DNA Probe

<400> SEQUENCE: 272
acccaacatc tcacgacacg agctgacgac aaccatgcac cacctgtcac      50

<210> SEQ ID NO 273
<211> LENGTH: 50
<212> TYPE: DNA
<213> ORGANISM: Artificial sequence
<220> FEATURE:
<223> OTHER INFORMATION: DNA Probe

<400> SEQUENCE: 273
gacgtcctat ctctaggatt gtcagaggat gtcaagacct ggtaaggttc      50

<210> SEQ ID NO 274
<211> LENGTH: 50
<212> TYPE: DNA
<213> ORGANISM: Artificial sequence
<220> FEATURE:
<223> OTHER INFORMATION: DNA Probe

<400> SEQUENCE: 274
attaaaccac atgctccacc gcttgtgcgg gccccgtca attcctttga      50

<210> SEQ ID NO 275
<211> LENGTH: 50
<212> TYPE: DNA
<213> ORGANISM: Artificial sequence
<220> FEATURE:
<223> OTHER INFORMATION: DNA Probe
```

```
<400> SEQUENCE: 275
ccgtactccc caggcggagt gcttaatgcg ttagctgcag cactaagggg          50

<210> SEQ ID NO 276
<211> LENGTH: 50
<212> TYPE: DNA
<213> ORGANISM: Artificial sequence
<220> FEATURE:
<223> OTHER INFORMATION: DNA Probe

<400> SEQUENCE: 276
acttagcact catcgtttac ggcgtggact accagggtat ctaatcctgt          50

<210> SEQ ID NO 277
<211> LENGTH: 50
<212> TYPE: DNA
<213> ORGANISM: Artificial sequence
<220> FEATURE:
<223> OTHER INFORMATION: DNA Probe

<400> SEQUENCE: 277
tcgctcctca gcgtcagtta cagaccagag agtcgccttc gccactggtg          50

<210> SEQ ID NO 278
<211> LENGTH: 50
<212> TYPE: DNA
<213> ORGANISM: Artificial sequence
<220> FEATURE:
<223> OTHER INFORMATION: DNA Probe

<400> SEQUENCE: 278
acgcatttca ccgctacacg tggaattcca ctctcctctt ctgcactcaa          50

<210> SEQ ID NO 279
<211> LENGTH: 50
<212> TYPE: DNA
<213> ORGANISM: Artificial sequence
<220> FEATURE:
<223> OTHER INFORMATION: DNA Probe

<400> SEQUENCE: 279
atgaccctcc ccggttgagc cgggggcttt cacatcagac ttaagaaacc          50

<210> SEQ ID NO 280
<211> LENGTH: 50
<212> TYPE: DNA
<213> ORGANISM: Artificial sequence
<220> FEATURE:
<223> OTHER INFORMATION: DNA Probe

<400> SEQUENCE: 280
acgcccaata attccggaca acgcttgcca cctacgtatt accgcggctg          50

<210> SEQ ID NO 281
<211> LENGTH: 50
<212> TYPE: DNA
<213> ORGANISM: Artificial sequence
<220> FEATURE:
<223> OTHER INFORMATION: DNA Probe

<400> SEQUENCE: 281
ccgtggcttt ctggttaggt accgtcaagg taccgcccta ttcgaacggt          50

<210> SEQ ID NO 282
```

<211> LENGTH: 50
<212> TYPE: DNA
<213> ORGANISM: Artificial sequence
<220> FEATURE:
<223> OTHER INFORMATION: DNA Probe

<400> SEQUENCE: 282
acaacagagc tttacgatcc gaaaaccttc atcactcacg cggcgttgct          50

<210> SEQ ID NO 283
<211> LENGTH: 50
<212> TYPE: DNA
<213> ORGANISM: Artificial sequence
<220> FEATURE:
<223> OTHER INFORMATION: DNA Probe

<400> SEQUENCE: 283
ccattgcgga agattcccta ctgctgcctc ccgtaggagt ctgggccgtg          50

<210> SEQ ID NO 284
<211> LENGTH: 50
<212> TYPE: DNA
<213> ORGANISM: Artificial sequence
<220> FEATURE:
<223> OTHER INFORMATION: DNA Probe

<400> SEQUENCE: 284
ggccgatcac cctctcaggt cggctacgca tcgtcgcctt ggtgagccgt          50

<210> SEQ ID NO 285
<211> LENGTH: 50
<212> TYPE: DNA
<213> ORGANISM: Artificial sequence
<220> FEATURE:
<223> OTHER INFORMATION: DNA Probe

<400> SEQUENCE: 285
ctaatgcgcc gcgggtccat ctgtaagtgg tagccgaagc cacctttat          50

<210> SEQ ID NO 286
<211> LENGTH: 50
<212> TYPE: DNA
<213> ORGANISM: Artificial sequence
<220> FEATURE:
<223> OTHER INFORMATION: DNA Probe

<400> SEQUENCE: 286
ttcaaacaac catccggtat tagccccggt ttcccggagt tatcccagtc          50

<210> SEQ ID NO 287
<211> LENGTH: 50
<212> TYPE: DNA
<213> ORGANISM: Artificial sequence
<220> FEATURE:
<223> OTHER INFORMATION: DNA Probe

<400> SEQUENCE: 287
ccacgtgtta ctcacccgtc cgccgctaac atcagggagc aagctcccat          50

<210> SEQ ID NO 288
<211> LENGTH: 50
<212> TYPE: DNA
<213> ORGANISM: Artificial sequence
<220> FEATURE:
<223> OTHER INFORMATION: DNA Probe

<400> SEQUENCE: 288
gcatgtatta ggcacgccgc cagcgttcgt cctgagccag gatcaaactc        50

<210> SEQ ID NO 289
<211> LENGTH: 50
<212> TYPE: DNA
<213> ORGANISM: Artificial sequence
<220> FEATURE:
<223> OTHER INFORMATION: DNA Probe

<400> SEQUENCE: 289
tggttaagtc ctcgatcgat tagtatctgt cagctccatg tgtcgccaca        50

<210> SEQ ID NO 290
<211> LENGTH: 50
<212> TYPE: DNA
<213> ORGANISM: Artificial sequence
<220> FEATURE:
<223> OTHER INFORMATION: DNA Probe

<400> SEQUENCE: 290
tatcaacctg atcatctttc agggatctta cttccttgcg gaatgggaaa        50

<210> SEQ ID NO 291
<211> LENGTH: 50
<212> TYPE: DNA
<213> ORGANISM: Artificial sequence
<220> FEATURE:
<223> OTHER INFORMATION: DNA Probe

<400> SEQUENCE: 291
ggcttcatgc ttagatgctt tcagcactta tcccgtccgc acatagctac        50

<210> SEQ ID NO 292
<211> LENGTH: 50
<212> TYPE: DNA
<213> ORGANISM: Artificial sequence
<220> FEATURE:
<223> OTHER INFORMATION: DNA Probe

<400> SEQUENCE: 292
gcagaacaac tggtacacca gcggtgcgtc catcccggtc ctctcgtact        50

<210> SEQ ID NO 293
<211> LENGTH: 50
<212> TYPE: DNA
<213> ORGANISM: Artificial sequence
<220> FEATURE:
<223> OTHER INFORMATION: DNA Probe

<400> SEQUENCE: 293
caaatttcct gcgcccgcga cggataggga ccgaactgtc tcacgacgtt        50

<210> SEQ ID NO 294
<211> LENGTH: 50
<212> TYPE: DNA
<213> ORGANISM: Artificial sequence
<220> FEATURE:
<223> OTHER INFORMATION: DNA Probe

<400> SEQUENCE: 294
gtaccgcttt aatgggcgaa cagcccaacc cttgggactg actacagccc        50

<210> SEQ ID NO 295

<211> LENGTH: 50
<212> TYPE: DNA
<213> ORGANISM: Artificial sequence
<220> FEATURE:
<223> OTHER INFORMATION: DNA Probe

<400> SEQUENCE: 295
cgacatcgag gtgccaaacc tccccgtcga tgtggactct tgggggagat        50

<210> SEQ ID NO 296
<211> LENGTH: 50
<212> TYPE: DNA
<213> ORGANISM: Artificial sequence
<220> FEATURE:
<223> OTHER INFORMATION: DNA Probe

<400> SEQUENCE: 296
ggggtagctt ttatccgttg agcgatggcc cttccatgcg gaaccaccgg        50

<210> SEQ ID NO 297
<211> LENGTH: 50
<212> TYPE: DNA
<213> ORGANISM: Artificial sequence
<220> FEATURE:
<223> OTHER INFORMATION: DNA Probe

<400> SEQUENCE: 297
tttcgtccct gctcgacttg taggtctcgc agtcaagctc ccttgtgcct        50

<210> SEQ ID NO 298
<211> LENGTH: 50
<212> TYPE: DNA
<213> ORGANISM: Artificial sequence
<220> FEATURE:
<223> OTHER INFORMATION: DNA Probe

<400> SEQUENCE: 298
gatttccaac cattctgagg gaacctttgg gcgcctccgt tacctttag         50

<210> SEQ ID NO 299
<211> LENGTH: 50
<212> TYPE: DNA
<213> ORGANISM: Artificial sequence
<220> FEATURE:
<223> OTHER INFORMATION: DNA Probe

<400> SEQUENCE: 299
gtcaaactgc ccacctgaca ctgtctcccc gcccgataag ggcggcgggt        50

<210> SEQ ID NO 300
<211> LENGTH: 50
<212> TYPE: DNA
<213> ORGANISM: Artificial sequence
<220> FEATURE:
<223> OTHER INFORMATION: DNA Probe

<400> SEQUENCE: 300
gccagggtag tatcccaccg atgcctccac cgaagctggc gctccggttt        50

<210> SEQ ID NO 301
<211> LENGTH: 50
<212> TYPE: DNA
<213> ORGANISM: Artificial sequence
<220> FEATURE:
<223> OTHER INFORMATION: DNA Probe

<400> SEQUENCE: 301
atcctgtaca agctgtacca acattcaata tcaggctgca gtaaagctcc        50

<210> SEQ ID NO 302
<211> LENGTH: 50
<212> TYPE: DNA
<213> ORGANISM: Artificial sequence
<220> FEATURE:
<223> OTHER INFORMATION: DNA Probe

<400> SEQUENCE: 302
cctgtcgcgg gtaacctgca tcttcacagg tactataatt tcaccgagtc        50

<210> SEQ ID NO 303
<211> LENGTH: 50
<212> TYPE: DNA
<213> ORGANISM: Artificial sequence
<220> FEATURE:
<223> OTHER INFORMATION: DNA Probe

<400> SEQUENCE: 303
gcccagatcg ttgcgccttt cgtgcgggtc ggaacttacc cgacaaggaa        50

<210> SEQ ID NO 304
<211> LENGTH: 50
<212> TYPE: DNA
<213> ORGANISM: Artificial sequence
<220> FEATURE:
<223> OTHER INFORMATION: DNA Probe

<400> SEQUENCE: 304
accgttatag ttacggccgc cgtttactgg ggcttcaatt cgcaccttcg        50

<210> SEQ ID NO 305
<211> LENGTH: 50
<212> TYPE: DNA
<213> ORGANISM: Artificial sequence
<220> FEATURE:
<223> OTHER INFORMATION: DNA Probe

<400> SEQUENCE: 305
cctcttaacc ttccagcacc gggcaggcgt cagcccctat acttcgcctt        50

<210> SEQ ID NO 306
<211> LENGTH: 50
<212> TYPE: DNA
<213> ORGANISM: Artificial sequence
<220> FEATURE:
<223> OTHER INFORMATION: DNA Probe

<400> SEQUENCE: 306
cctgtgtttt tgctaaacag tcgcctgggc ctattcactg cggctctctc        50

<210> SEQ ID NO 307
<211> LENGTH: 50
<212> TYPE: DNA
<213> ORGANISM: Artificial sequence
<220> FEATURE:
<223> OTHER INFORMATION: DNA Probe

<400> SEQUENCE: 307
cagagcaccc cttctcccga agttacgggg tcattttgcc gagttcctta        50

<210> SEQ ID NO 308

<211> LENGTH: 50
<212> TYPE: DNA
<213> ORGANISM: Artificial sequence
<220> FEATURE:
<223> OTHER INFORMATION: DNA Probe

<400> SEQUENCE: 308
atcaccttag gattctctcc tcgcctacct gtgtcggttt gcggtacggg          50

<210> SEQ ID NO 309
<211> LENGTH: 50
<212> TYPE: DNA
<213> ORGANISM: Artificial sequence
<220> FEATURE:
<223> OTHER INFORMATION: DNA Probe

<400> SEQUENCE: 309
tagaggcttt tcttggcagt gtggaatcag gaacttcgct actatatttc          50

<210> SEQ ID NO 310
<211> LENGTH: 50
<212> TYPE: DNA
<213> ORGANISM: Artificial sequence
<220> FEATURE:
<223> OTHER INFORMATION: DNA Probe

<400> SEQUENCE: 310
tcagccttat gggaaacgga tttgcctatt tcccagccta actgcttgga          50

<210> SEQ ID NO 311
<211> LENGTH: 50
<212> TYPE: DNA
<213> ORGANISM: Artificial sequence
<220> FEATURE:
<223> OTHER INFORMATION: DNA Probe

<400> SEQUENCE: 311
ccgcgcttac cctatcctcc tgcgtccccc cattgctcaa atggtgagga          50

<210> SEQ ID NO 312
<211> LENGTH: 50
<212> TYPE: DNA
<213> ORGANISM: Artificial sequence
<220> FEATURE:
<223> OTHER INFORMATION: DNA Probe

<400> SEQUENCE: 312
tcaacctgtt gtccatcgcc tacgcctttc ggcctcggct taggtcccga          50

<210> SEQ ID NO 313
<211> LENGTH: 50
<212> TYPE: DNA
<213> ORGANISM: Artificial sequence
<220> FEATURE:
<223> OTHER INFORMATION: DNA Probe

<400> SEQUENCE: 313
cgagccttcc tcaggaaacc ttaggcattc ggtggagggg attctcaccc          50

<210> SEQ ID NO 314
<211> LENGTH: 50
<212> TYPE: DNA
<213> ORGANISM: Artificial sequence
<220> FEATURE:
<223> OTHER INFORMATION: DNA Probe

<400> SEQUENCE: 314
taccggcatt ctcacttcta agcgctccac cagtccttcc ggtctggctt              50

<210> SEQ ID NO 315
<211> LENGTH: 50
<212> TYPE: DNA
<213> ORGANISM: Artificial sequence
<220> FEATURE:
<223> OTHER INFORMATION: DNA Probe

<400> SEQUENCE: 315
gctctcctac cactgttcga agaacagtcc gcagcttcgg tgatacgttt              50

<210> SEQ ID NO 316
<211> LENGTH: 50
<212> TYPE: DNA
<213> ORGANISM: Artificial sequence
<220> FEATURE:
<223> OTHER INFORMATION: DNA Probe

<400> SEQUENCE: 316
tcggcgcaga gtcactcgac cagtgagcta ttacgcactc tttaaatggt              50

<210> SEQ ID NO 317
<211> LENGTH: 50
<212> TYPE: DNA
<213> ORGANISM: Artificial sequence
<220> FEATURE:
<223> OTHER INFORMATION: DNA Probe

<400> SEQUENCE: 317
aacatcctgg ttgtctaagc aactccacat cctttccac ttaacgtata              50

<210> SEQ ID NO 318
<211> LENGTH: 50
<212> TYPE: DNA
<213> ORGANISM: Artificial sequence
<220> FEATURE:
<223> OTHER INFORMATION: DNA Probe

<400> SEQUENCE: 318
tggcggtctg ggctgtttcc ctttcgacta cggatcttat cactcgcagt              50

<210> SEQ ID NO 319
<211> LENGTH: 50
<212> TYPE: DNA
<213> ORGANISM: Artificial sequence
<220> FEATURE:
<223> OTHER INFORMATION: DNA Probe

<400> SEQUENCE: 319
aagtcattgg cattcggagt ttgactgaat tcggtaaccc ggtaggggcc              50

<210> SEQ ID NO 320
<211> LENGTH: 50
<212> TYPE: DNA
<213> ORGANISM: Artificial sequence
<220> FEATURE:
<223> OTHER INFORMATION: DNA Probe

<400> SEQUENCE: 320
gctctacctc caagactctt accttgaggc tagccctaaa gctatttcgg              50

<210> SEQ ID NO 321

-continued

```
<210> SEQ ID NO 322
<211> LENGTH: 50
<212> TYPE: DNA
<213> ORGANISM: Artificial sequence
<220> FEATURE:
<223> OTHER INFORMATION: DNA Probe

<400> SEQUENCE: 321
tccaggttcg attggcattt caccectacc cacacctcat ccccgcactt      50

<210> SEQ ID NO 322
<211> LENGTH: 50
<212> TYPE: DNA
<213> ORGANISM: Artificial sequence
<220> FEATURE:
<223> OTHER INFORMATION: DNA Probe

<400> SEQUENCE: 322
ttcgggcctc cattcagtgt tacctgaact tcaccctgga catgggtaga      50

<210> SEQ ID NO 323
<211> LENGTH: 50
<212> TYPE: DNA
<213> ORGANISM: Artificial sequence
<220> FEATURE:
<223> OTHER INFORMATION: DNA Probe

<400> SEQUENCE: 323
tctacgacca cgtactcatg cgccctattc agactcgctt tcgctgcggc      50

<210> SEQ ID NO 324
<211> LENGTH: 50
<212> TYPE: DNA
<213> ORGANISM: Artificial sequence
<220> FEATURE:
<223> OTHER INFORMATION: DNA Probe

<400> SEQUENCE: 324
taaccttgca cgggatcgta actcgccggt tcattctaca aaaggcacgc      50

<210> SEQ ID NO 325
<211> LENGTH: 50
<212> TYPE: DNA
<213> ORGANISM: Artificial sequence
<220> FEATURE:
<223> OTHER INFORMATION: DNA Probe

<400> SEQUENCE: 325
ggctctgact acttgtaggc acacggtttc aggatctctt tcactcccct      50

<210> SEQ ID NO 326
<211> LENGTH: 50
<212> TYPE: DNA
<213> ORGANISM: Artificial sequence
<220> FEATURE:
<223> OTHER INFORMATION: DNA Probe

<400> SEQUENCE: 326
acctttccct cacggtactg gttcactatc ggtcactagg gagtatttag      50

<210> SEQ ID NO 327
<211> LENGTH: 50
<212> TYPE: DNA
<213> ORGANISM: Artificial sequence
<220> FEATURE:
<223> OTHER INFORMATION: DNA Probe
```

```
<400> SEQUENCE: 327
ctcccggatt ccgacggaat ttcacgtgtt ccgccgtact caggatccac                50

<210> SEQ ID NO 328
<211> LENGTH: 50
<212> TYPE: DNA
<213> ORGANISM: Artificial sequence
<220> FEATURE:
<223> OTHER INFORMATION: DNA Probe

<400> SEQUENCE: 328
gttttgacta cagggctgtt acctcctatg gcgggccttt ccagacctct                50

<210> SEQ ID NO 329
<211> LENGTH: 50
<212> TYPE: DNA
<213> ORGANISM: Artificial sequence
<220> FEATURE:
<223> OTHER INFORMATION: DNA Probe

<400> SEQUENCE: 329
ctttgtaact ccgtacagag tgtcctacaa ccccaagagg caagcctctt                50

<210> SEQ ID NO 330
<211> LENGTH: 50
<212> TYPE: DNA
<213> ORGANISM: Artificial sequence
<220> FEATURE:
<223> OTHER INFORMATION: DNA Probe

<400> SEQUENCE: 330
cgtttcgctc gccgctactc agggaatcgc atttgctttc tcttcctccg                50

<210> SEQ ID NO 331
<211> LENGTH: 50
<212> TYPE: DNA
<213> ORGANISM: Artificial sequence
<220> FEATURE:
<223> OTHER INFORMATION: DNA Probe

<400> SEQUENCE: 331
cagttccccg ggtctgcctt ctcatatcct atgaattcag atatggatac                50

<210> SEQ ID NO 332
<211> LENGTH: 50
<212> TYPE: DNA
<213> ORGANISM: Artificial sequence
<220> FEATURE:
<223> OTHER INFORMATION: DNA Probe

<400> SEQUENCE: 332
ggtgggtttc cccattcgga aatctccgga tcaaagcttg cttacagctc                50

<210> SEQ ID NO 333
<211> LENGTH: 50
<212> TYPE: DNA
<213> ORGANISM: Artificial sequence
<220> FEATURE:
<223> OTHER INFORMATION: DNA Probe

<400> SEQUENCE: 333
tgttcgtccc gtccttcatc ggctcctagt gccaaggcat ccaccgtgcg                50

<210> SEQ ID NO 334
```

<210> SEQ ID NO 334
<211> LENGTH: 50
<212> TYPE: DNA
<213> ORGANISM: Artificial sequence
<220> FEATURE:
<223> OTHER INFORMATION: DNA Probe

<400> SEQUENCE: 334
aaactagatt cgaatataac aaaacattac atcctcatcc aatccctttt    50

<210> SEQ ID NO 335
<211> LENGTH: 50
<212> TYPE: DNA
<213> ORGANISM: Artificial sequence
<220> FEATURE:
<223> OTHER INFORMATION: DNA Probe

<400> SEQUENCE: 335
gcggtgtgtg caaggagcag ggacgtattc accgcgcgat tgtgacacgc    50

<210> SEQ ID NO 336
<211> LENGTH: 50
<212> TYPE: DNA
<213> ORGANISM: Artificial sequence
<220> FEATURE:
<223> OTHER INFORMATION: DNA Probe

<400> SEQUENCE: 336
gcctttcggc gtcggaaccc attgtctcag ccattgtagc ccgcgtgttg    50

<210> SEQ ID NO 337
<211> LENGTH: 50
<212> TYPE: DNA
<213> ORGANISM: Artificial sequence
<220> FEATURE:
<223> OTHER INFORMATION: DNA Probe

<400> SEQUENCE: 337
gcatacggac ctaccgtcgt ccactccttc ctcctattta tcataggcgg    50

<210> SEQ ID NO 338
<211> LENGTH: 50
<212> TYPE: DNA
<213> ORGANISM: Artificial sequence
<220> FEATURE:
<223> OTHER INFORMATION: DNA Probe

<400> SEQUENCE: 338
cggcatccaa aaaaggatcc gctggtaact aagagcgtgg gtctcgctcg    50

<210> SEQ ID NO 339
<211> LENGTH: 50
<212> TYPE: DNA
<213> ORGANISM: Artificial sequence
<220> FEATURE:
<223> OTHER INFORMATION: DNA Probe

<400> SEQUENCE: 339
caacctggct atcatacagc tgtcgcctct ggtgagatgt ccggcgttga    50

<210> SEQ ID NO 340
<211> LENGTH: 50
<212> TYPE: DNA
<213> ORGANISM: Artificial sequence
<220> FEATURE:
<223> OTHER INFORMATION: DNA Probe

```
<400> SEQUENCE: 340
aggctccacg cgttgtggtg ctcccccgcc aattcctttta agtttcagtc                    50

<210> SEQ ID NO 341
<211> LENGTH: 50
<212> TYPE: DNA
<213> ORGANISM: Artificial sequence
<220> FEATURE:
<223> OTHER INFORMATION: DNA Probe

<400> SEQUENCE: 341
ccaggcggcg gacttaacag cttcccttcg gcactgggac agctcaaagc                    50

<210> SEQ ID NO 342
<211> LENGTH: 50
<212> TYPE: DNA
<213> ORGANISM: Artificial sequence
<220> FEATURE:
<223> OTHER INFORMATION: DNA Probe

<400> SEQUENCE: 342
tccgcatcgt ttacagctag gactacccgg gtatctaatc cggttcgcgc                    50

<210> SEQ ID NO 343
<211> LENGTH: 50
<212> TYPE: DNA
<213> ORGANISM: Artificial sequence
<220> FEATURE:
<223> OTHER INFORMATION: DNA Probe

<400> SEQUENCE: 343
ttcccacagt taagctgcag gatttcacca gagacttatt aaaccggcta                    50

<210> SEQ ID NO 344
<211> LENGTH: 50
<212> TYPE: DNA
<213> ORGANISM: Artificial sequence
<220> FEATURE:
<223> OTHER INFORMATION: DNA Probe

<400> SEQUENCE: 344
ctcttattcc aaaagctctt tacactaatg aaaagccatc ccgttaagaa                    50

<210> SEQ ID NO 345
<211> LENGTH: 50
<212> TYPE: DNA
<213> ORGANISM: Artificial sequence
<220> FEATURE:
<223> OTHER INFORMATION: DNA Probe

<400> SEQUENCE: 345
cccccgtcgc gatttctcac attgcggagg tttcgcgcct gctgcacccc                    50

<210> SEQ ID NO 346
<211> LENGTH: 50
<212> TYPE: DNA
<213> ORGANISM: Artificial sequence
<220> FEATURE:
<223> OTHER INFORMATION: DNA Probe

<400> SEQUENCE: 346
ttgtctcagg ttccatctcc gggctcttgc tctcacaacc cgtaccgatc                    50

<210> SEQ ID NO 347
```

<211> LENGTH: 50
<212> TYPE: DNA
<213> ORGANISM: Artificial sequence
<220> FEATURE:
<223> OTHER INFORMATION: DNA Probe

<400> SEQUENCE: 347
cattacctaa ccaactacct aatcggccgc agacccatcc ttaggcgaaa    50

<210> SEQ ID NO 348
<211> LENGTH: 50
<212> TYPE: DNA
<213> ORGANISM: Artificial sequence
<220> FEATURE:
<223> OTHER INFORMATION: DNA Probe

<400> SEQUENCE: 348
aaaccattac aggaataatt gcctatccag tattatcccc agtttcccag    50

<210> SEQ ID NO 349
<211> LENGTH: 50
<212> TYPE: DNA
<213> ORGANISM: Artificial sequence
<220> FEATURE:
<223> OTHER INFORMATION: DNA Probe

<400> SEQUENCE: 349
aagggtaggt tatccacgtg ttactgagcc gtacgccacg agcctaaact    50

<210> SEQ ID NO 350
<211> LENGTH: 50
<212> TYPE: DNA
<213> ORGANISM: Artificial sequence
<220> FEATURE:
<223> OTHER INFORMATION: DNA Probe

<400> SEQUENCE: 350
acctagcgcg tagctgcccg gcactgcctt atcagacaac cggtcgacca    50

<210> SEQ ID NO 351
<211> LENGTH: 50
<212> TYPE: DNA
<213> ORGANISM: Artificial sequence
<220> FEATURE:
<223> OTHER INFORMATION: DNA Probe

<400> SEQUENCE: 351
cgttcctctc gtactggagc caccttcccc tcagactact aacacatcca    50

<210> SEQ ID NO 352
<211> LENGTH: 50
<212> TYPE: DNA
<213> ORGANISM: Artificial sequence
<220> FEATURE:
<223> OTHER INFORMATION: DNA Probe

<400> SEQUENCE: 352
cctgtctcac gacggtctaa acccagctca cgttcccctt taatgggcga    50

<210> SEQ ID NO 353
<211> LENGTH: 50
<212> TYPE: DNA
<213> ORGANISM: Artificial sequence
<220> FEATURE:
<223> OTHER INFORMATION: DNA Probe -continued

<400> SEQUENCE: 353
ggtgctgctg cacacccagg atggaaagaa ccgacatcga agtagcaagc    50

<210> SEQ ID NO 354
<211> LENGTH: 50
<212> TYPE: DNA
<213> ORGANISM: Artificial sequence
<220> FEATURE:
<223> OTHER INFORMATION: DNA Probe

<400> SEQUENCE: 354
ggctcttgcc tgcgaccacc cagttatccc cgaggtagtt tttctgtcat    50

<210> SEQ ID NO 355
<211> LENGTH: 50
<212> TYPE: DNA
<213> ORGANISM: Artificial sequence
<220> FEATURE:
<223> OTHER INFORMATION: DNA Probe

<400> SEQUENCE: 355
aggaggactc tgaggttcgc taggcccggc tttcgcctct ggatttcttg    50

<210> SEQ ID NO 356
<211> LENGTH: 50
<212> TYPE: DNA
<213> ORGANISM: Artificial sequence
<220> FEATURE:
<223> OTHER INFORMATION: DNA Probe

<400> SEQUENCE: 356
caaagtaagt tagaaacaca gtcataagaa agtggtgtct caagaacgaa    50

<210> SEQ ID NO 357
<211> LENGTH: 50
<212> TYPE: DNA
<213> ORGANISM: Artificial sequence
<220> FEATURE:
<223> OTHER INFORMATION: DNA Probe

<400> SEQUENCE: 357
gacttataat cgaattctcc cacttacact gcatacctat aaccaagctt    50

<210> SEQ ID NO 358
<211> LENGTH: 50
<212> TYPE: DNA
<213> ORGANISM: Artificial sequence
<220> FEATURE:
<223> OTHER INFORMATION: DNA Probe

<400> SEQUENCE: 358
gtaaaactct acggggtctt cgcttcccaa tggaagactc tggcttgtgc    50

<210> SEQ ID NO 359
<211> LENGTH: 50
<212> TYPE: DNA
<213> ORGANISM: Artificial sequence
<220> FEATURE:
<223> OTHER INFORMATION: DNA Probe

<400> SEQUENCE: 359
tcactaagtt ctagctaggg acagtgggga cctcgttcta ccattcatgc    50

<210> SEQ ID NO 360

<211> LENGTH: 50
<212> TYPE: DNA
<213> ORGANISM: Artificial sequence
<220> FEATURE:
<223> OTHER INFORMATION: DNA Probe

<400> SEQUENCE: 360
cgacaaggca tttcgctacc ttaagagggt tatagttacc cccgccgttt    50

<210> SEQ ID NO 361
<211> LENGTH: 50
<212> TYPE: DNA
<213> ORGANISM: Artificial sequence
<220> FEATURE:
<223> OTHER INFORMATION: DNA Probe

<400> SEQUENCE: 361
aactgaactc cagcttcacg tgccagcact gggcaggtgt cgccctctgt    50

<210> SEQ ID NO 362
<211> LENGTH: 50
<212> TYPE: DNA
<213> ORGANISM: Artificial sequence
<220> FEATURE:
<223> OTHER INFORMATION: DNA Probe

<400> SEQUENCE: 362
ctagcagaga gctatgtttt tattaaacag tcgggccccc ctagtcactg    50

<210> SEQ ID NO 363
<211> LENGTH: 50
<212> TYPE: DNA
<213> ORGANISM: Artificial sequence
<220> FEATURE:
<223> OTHER INFORMATION: DNA Probe

<400> SEQUENCE: 363
ttaaaacgcc ttagcctact cagctagggg cacctgtgac ggatctcggt    50

<210> SEQ ID NO 364
<211> LENGTH: 50
<212> TYPE: DNA
<213> ORGANISM: Artificial sequence
<220> FEATURE:
<223> OTHER INFORMATION: DNA Probe

<400> SEQUENCE: 364
acaaaactaa ctcccttttc aaggactcca tgaatcagtt aaaccagtac    50

<210> SEQ ID NO 365
<211> LENGTH: 50
<212> TYPE: DNA
<213> ORGANISM: Artificial sequence
<220> FEATURE:
<223> OTHER INFORMATION: DNA Probe

<400> SEQUENCE: 365
ataatgccta cacctggttc tcgctattac acctctcccc aggcttaaac    50

<210> SEQ ID NO 366
<211> LENGTH: 50
<212> TYPE: DNA
<213> ORGANISM: Artificial sequence
<220> FEATURE:
<223> OTHER INFORMATION: DNA Probe

```
<400> SEQUENCE: 366
caatcctaca aaacatatct cgaagtgtca gaaattagcc ctcaacgtca              50

<210> SEQ ID NO 367
<211> LENGTH: 50
<212> TYPE: DNA
<213> ORGANISM: Artificial sequence
<220> FEATURE:
<223> OTHER INFORMATION: DNA Probe

<400> SEQUENCE: 367
ctttgctgct actactacca ggatccacat acctgcaagg tccaaaggaa              50

<210> SEQ ID NO 368
<211> LENGTH: 50
<212> TYPE: DNA
<213> ORGANISM: Artificial sequence
<220> FEATURE:
<223> OTHER INFORMATION: DNA Probe

<400> SEQUENCE: 368
caacccacac aggtcgccac tctacacaat caccaaaaaa aaggtgttcc              50

<210> SEQ ID NO 369
<211> LENGTH: 50
<212> TYPE: DNA
<213> ORGANISM: Artificial sequence
<220> FEATURE:
<223> OTHER INFORMATION: DNA Probe

<400> SEQUENCE: 369
ggattaattc ccgtccattt taggtgcctc tgacctcgat gggtgatctg              50

<210> SEQ ID NO 370
<211> LENGTH: 50
<212> TYPE: DNA
<213> ORGANISM: Artificial sequence
<220> FEATURE:
<223> OTHER INFORMATION: DNA Probe

<400> SEQUENCE: 370
agggtggctg cttctaagcc caccttccca ttgtcttggg ccaaagactc              50

<210> SEQ ID NO 371
<211> LENGTH: 50
<212> TYPE: DNA
<213> ORGANISM: Artificial sequence
<220> FEATURE:
<223> OTHER INFORMATION: DNA Probe

<400> SEQUENCE: 371
gtatttaggg gccttaacca tagtctgagt tgtttctctt tcggacaca               50

<210> SEQ ID NO 372
<211> LENGTH: 50
<212> TYPE: DNA
<213> ORGANISM: Artificial sequence
<220> FEATURE:
<223> OTHER INFORMATION: DNA Probe

<400> SEQUENCE: 372
cctcactcca accttctacg acggtgacga gttcggagtt ttacagtacg              50

<210> SEQ ID NO 373
```

```
<211> LENGTH: 50
<212> TYPE: DNA
<213> ORGANISM: Artificial sequence
<220> FEATURE:
<223> OTHER INFORMATION: DNA Probe

<400> SEQUENCE: 373
ccctaaacgt ccaattagtg ctctaccccg ccaccaacct ccagtcaggc          50

<210> SEQ ID NO 374
<211> LENGTH: 50
<212> TYPE: DNA
<213> ORGANISM: Artificial sequence
<220> FEATURE:
<223> OTHER INFORMATION: DNA Probe

<400> SEQUENCE: 374
aatagatcga ccggcttcgg gtttcaatgc tgtgattcca ggccctatta          50

<210> SEQ ID NO 375
<211> LENGTH: 50
<212> TYPE: DNA
<213> ORGANISM: Artificial sequence
<220> FEATURE:
<223> OTHER INFORMATION: DNA Probe

<400> SEQUENCE: 375
acaacgctgc gggcatatcg gtttccctac gactacaagg ataaaaacct          50

<210> SEQ ID NO 376
<211> LENGTH: 50
<212> TYPE: DNA
<213> ORGANISM: Artificial sequence
<220> FEATURE:
<223> OTHER INFORMATION: DNA Probe

<400> SEQUENCE: 376
acaaagaact ccctggcccg tgtttcaaga cggacgatgc aacactagtc          50

<210> SEQ ID NO 377
<211> LENGTH: 50
<212> TYPE: DNA
<213> ORGANISM: Artificial sequence
<220> FEATURE:
<223> OTHER INFORMATION: DNA Probe

<400> SEQUENCE: 377
acaatgttac cactgattct ttcggaagaa ttcattcctt acgcgccaca          50

<210> SEQ ID NO 378
<211> LENGTH: 50
<212> TYPE: DNA
<213> ORGANISM: Artificial sequence
<220> FEATURE:
<223> OTHER INFORMATION: DNA Probe

<400> SEQUENCE: 378
ctggtttcag gtacttttca cccccctata ggggtacttt tcagcattcc          50

<210> SEQ ID NO 379
<211> LENGTH: 50
<212> TYPE: DNA
<213> ORGANISM: Artificial sequence
<220> FEATURE:
<223> OTHER INFORMATION: DNA Probe
```

<400> SEQUENCE: 379
ctctatcggt cttgagacgt atttagaatt ggaagttgat gcctcccaca          50

<210> SEQ ID NO 380
<211> LENGTH: 50
<212> TYPE: DNA
<213> ORGANISM: Artificial sequence
<220> FEATURE:
<223> OTHER INFORMATION: DNA Probe

<400> SEQUENCE: 380
atcaccctct acggttctaa aattccaaat aaaattcgat ttatcccacg          50

<210> SEQ ID NO 381
<211> LENGTH: 50
<212> TYPE: DNA
<213> ORGANISM: Artificial sequence
<220> FEATURE:
<223> OTHER INFORMATION: DNA Probe

<400> SEQUENCE: 381
tctatacacc acatctccct aatattacta aaagggattc agtttgttct          50

<210> SEQ ID NO 382
<211> LENGTH: 50
<212> TYPE: DNA
<213> ORGANISM: Artificial sequence
<220> FEATURE:
<223> OTHER INFORMATION: DNA Probe

<400> SEQUENCE: 382
gccgttacta acgacatcgc atattgcttt cttttcctcc gcctactaag          50

<210> SEQ ID NO 383
<211> LENGTH: 50
<212> TYPE: DNA
<213> ORGANISM: Artificial sequence
<220> FEATURE:
<223> OTHER INFORMATION: DNA Probe

<400> SEQUENCE: 383
gggttcccaa tcctacacgg atcaacacaa aaaaaatgtg ctaggaagtc          50

<210> SEQ ID NO 384
<211> LENGTH: 50
<212> TYPE: DNA
<213> ORGANISM: Artificial sequence
<220> FEATURE:
<223> OTHER INFORMATION: DNA Probe

<400> SEQUENCE: 384
actactggga tcgaaacgag accaggtata accccatgc tatgaccgca          50

<210> SEQ ID NO 385
<211> LENGTH: 50
<212> TYPE: PRT
<213> ORGANISM: Mus musculus

<400> SEQUENCE: 385

Gly Cys Gly Thr Ala Thr Gly Cys Cys Thr Gly Gly Ala Gly Ala Ala
1               5                   10                  15

Thr Thr Gly Gly Ala Ala Thr Thr Cys Thr Thr Gly Thr Thr Ala Cys
            20                  25                  30

Thr Cys Ala Thr Ala Cys Thr Ala Cys Ala Gly Thr Gly Thr Thr
        35                  40                  45

Gly Cys
    50

<210> SEQ ID NO 386
<211> LENGTH: 50
<212> TYPE: PRT
<213> ORGANISM: Mus musculus

<400> SEQUENCE: 386

Gly Ala Thr Thr Ala Ala Cys Cys Ala Thr Thr Thr Thr Ala
1               5                   10                  15

Ala Gly Thr Thr Thr Ala Gly Gly Ala Ala Gly Thr Thr Gly Gly Thr
                20                  25                  30

Gly Thr Ala Ala Ala Thr Thr Ala Thr Gly Gly Ala Ala Thr Thr Ala
        35                  40                  45

Ala Thr
    50

<210> SEQ ID NO 387
<211> LENGTH: 50
<212> TYPE: PRT
<213> ORGANISM: Mus musculus

<400> SEQUENCE: 387

Ala Gly Cys Thr Thr Gly Ala Ala Cys Gly Cys Thr Thr Cys Thr
1               5                   10                  15

Thr Thr Ala Thr Thr Gly Gly Thr Gly Gly Cys Thr Gly Cys Thr Thr
                20                  25                  30

Thr Thr Ala Gly Gly Cys Cys Thr Ala Cys Ala Ala Thr Gly Gly Thr
        35                  40                  45

Thr Ala
    50

<210> SEQ ID NO 388
<211> LENGTH: 50
<212> TYPE: PRT
<213> ORGANISM: Mus musculus

<400> SEQUENCE: 388

Ala Thr Thr Ala Thr Thr Cys Ala Cys Thr Ala Thr Ala Ala Ala
1               5                   10                  15

Gly Gly Thr Thr Thr Thr Thr Thr Cys Cys Gly Thr Thr Cys Cys Ala
                20                  25                  30

Gly Ala Ala Gly Ala Gly Cys Thr Gly Thr Cys Cys Cys Thr Cys Thr
        35                  40                  45

Thr Thr
    50

<210> SEQ ID NO 389
<211> LENGTH: 50
<212> TYPE: PRT
<213> ORGANISM: Mus musculus

<400> SEQUENCE: 389

Cys Thr Thr Ala Cys Thr Thr Thr Thr Gly Ala Thr Thr Thr
1               5                   10                  15

Gly Thr Thr Gly Thr Thr Thr Thr Thr Thr Ala Gly Cys Ala Ala
                20                  25                  30

-continued

Gly Thr Thr Thr Ala Ala Ala Thr Thr Gly Ala Ala Cys Thr Thr
            35                  40                  45
Ala Ala
    50

<210> SEQ ID NO 390
<211> LENGTH: 50
<212> TYPE: PRT
<213> ORGANISM: Mus musculus

<400> SEQUENCE: 390

Ala Ala Cys Cys Ala Gly Cys Thr Ala Thr Cys Ala Cys Ala Ala
1               5                   10                  15
Gly Cys Thr Cys Gly Thr Thr Ala Gly Gly Cys Thr Thr Thr Cys
                20                  25                  30
Ala Cys Cys Thr Cys Thr Ala Cys Cys Thr Ala Ala Ala Ala Thr
            35                  40                  45
Cys Thr
    50

<210> SEQ ID NO 391
<211> LENGTH: 50
<212> TYPE: PRT
<213> ORGANISM: Mus musculus

<400> SEQUENCE: 391

Ala Ala Thr Ala Cys Thr Thr Gly Thr Ala Thr Gly Cys Thr Ala
1               5                   10                  15
Gly Ala Gly Gly Thr Gly Ala Thr Gly Thr Thr Thr Thr Gly Gly
                20                  25                  30
Thr Ala Ala Ala Cys Ala Gly Gly Cys Gly Gly Gly Thr Thr Cys
            35                  40                  45
Thr Thr
    50

<210> SEQ ID NO 392
<211> LENGTH: 50
<212> TYPE: PRT
<213> ORGANISM: Mus musculus

<400> SEQUENCE: 392

Thr Thr Thr Ala Thr Cys Thr Thr Thr Thr Gly Gly Ala Thr Cys
1               5                   10                  15
Thr Thr Thr Cys Cys Thr Thr Thr Ala Gly Gly Cys Ala Thr Thr Cys
                20                  25                  30
Cys Gly Gly Thr Gly Thr Thr Gly Gly Thr Thr Ala Ala Cys Ala
            35                  40                  45
Gly Ala
    50

<210> SEQ ID NO 393
<211> LENGTH: 50
<212> TYPE: PRT
<213> ORGANISM: Mus musculus

<400> SEQUENCE: 393

Thr Thr Ala Thr Thr Thr Ala Thr Ala Gly Thr Gly Thr Gly Ala Thr
1               5                   10                  15

```
Thr Ala Thr Thr Gly Cys Cys Thr Ala Thr Ala Gly Thr Cys Thr Gly
            20                  25                  30

Ala Thr Thr Ala Ala Cys Thr Ala Ala Cys Ala Ala Thr Gly Gly Thr
        35                  40                  45

Thr Ala
    50

<210> SEQ ID NO 394
<211> LENGTH: 50
<212> TYPE: PRT
<213> ORGANISM: Rattus norvegicus

<400> SEQUENCE: 394

Ala Gly Thr Gly Ala Thr Thr Gly Thr Ala Gly Thr Thr Gly Thr Thr
1               5                   10                  15

Thr Ala Thr Thr Cys Ala Cys Thr Ala Thr Thr Thr Ala Ala Gly Gly
            20                  25                  30

Thr Thr Thr Thr Thr Thr Cys Cys Thr Thr Thr Cys Cys Thr Ala
        35                  40                  45

Ala Ala
    50

<210> SEQ ID NO 395
<211> LENGTH: 50
<212> TYPE: PRT
<213> ORGANISM: Rattus norvegicus

<400> SEQUENCE: 395

Thr Gly Gly Cys Thr Ala Thr Ala Thr Thr Thr Thr Ala Ala Gly Thr
1               5                   10                  15

Thr Thr Ala Cys Ala Thr Thr Thr Thr Gly Ala Thr Thr Thr Gly Thr
            20                  25                  30

Thr Gly Thr Thr Cys Thr Gly Ala Thr Gly Gly Thr Ala Ala Gly Cys
        35                  40                  45

Thr Thr
    50

<210> SEQ ID NO 396
<211> LENGTH: 50
<212> TYPE: PRT
<213> ORGANISM: Rattus norvegicus

<400> SEQUENCE: 396

Thr Thr Thr Thr Thr Thr Thr Ala Ala Thr Cys Thr Thr Thr Cys Cys
1               5                   10                  15

Thr Thr Ala Ala Ala Gly Cys Ala Cys Gly Cys Cys Thr Gly Thr Gly
            20                  25                  30

Thr Thr Gly Gly Gly Cys Thr Ala Ala Cys Gly Ala Gly Thr Thr Ala
        35                  40                  45

Gly Gly
    50

<210> SEQ ID NO 397
<211> LENGTH: 50
<212> TYPE: PRT
<213> ORGANISM: Rattus norvegicus
```

<400> SEQUENCE: 397

Thr Gly Thr Thr Gly Gly Gly Thr Thr Ala Gly Thr Ala Cys Cys Thr
1               5                   10                  15

Ala Thr Gly Ala Thr Thr Cys Gly Ala Thr Ala Ala Thr Thr Gly Ala
                20                  25                  30

Cys Ala Ala Thr Gly Gly Thr Thr Ala Thr Cys Cys Gly Gly Gly Thr
            35                  40                  45

Thr Gly
    50

<210> SEQ ID NO 398
<211> LENGTH: 50
<212> TYPE: PRT
<213> ORGANISM: Rattus norvegicus

<400> SEQUENCE: 398

Ala Gly Gly Ala Gly Ala Ala Thr Thr Gly Gly Thr Thr Cys Thr Thr
1               5                   10                  15

Gly Thr Thr Ala Cys Thr Cys Ala Thr Ala Thr Thr Ala Ala Cys Ala
                20                  25                  30

Gly Thr Ala Thr Thr Thr Cys Ala Thr Cys Thr Ala Thr Gly Gly Ala
            35                  40                  45

Thr Cys
    50

<210> SEQ ID NO 399
<211> LENGTH: 50
<212> TYPE: PRT
<213> ORGANISM: Rattus norvegicus

<400> SEQUENCE: 399

Thr Thr Thr Gly Thr Gly Ala Thr Ala Thr Ala Gly Gly Ala Ala Thr
1               5                   10                  15

Thr Thr Ala Thr Thr Gly Ala Gly Gly Thr Thr Thr Gly Thr Gly Gly
                20                  25                  30

Ala Ala Thr Thr Ala Gly Thr Gly Thr Gly Thr Gly Thr Ala Ala Gly
            35                  40                  45

Thr Ala
    50

<210> SEQ ID NO 400
<211> LENGTH: 50
<212> TYPE: PRT
<213> ORGANISM: Mus musculus

<400> SEQUENCE: 400

Gly Cys Cys Gly Gly Gly Gly Ala Gly Thr Gly Gly Gly Thr Cys Thr
1               5                   10                  15

Thr Cys Cys Gly Thr Ala Cys Gly Cys Cys Ala Cys Ala Thr Thr Thr
                20                  25                  30

Cys Cys Cys Ala Cys Gly Cys Cys Gly Cys Gly Ala Cys Gly Cys Gly
            35                  40                  45

Cys Gly
    50

<210> SEQ ID NO 401
<211> LENGTH: 50
<212> TYPE: PRT

<213> ORGANISM: Mus musculus

<400> SEQUENCE: 401

Ala Cys Cys Thr Cys Gly Gly Gly Cys Cys Cys Cys Gly Gly Gly
1               5                   10                  15
Cys Gly Gly Gly Gly Cys Cys Cys Thr Thr Cys Ala Cys Cys Thr Thr
                20                  25                  30
Cys Ala Thr Thr Gly Cys Gly Cys Cys Ala Cys Gly Gly Cys Gly Gly
        35                  40                  45
Cys Thr
    50

<210> SEQ ID NO 402
<211> LENGTH: 50
<212> TYPE: PRT
<213> ORGANISM: Mus musculus

<400> SEQUENCE: 402

Thr Cys Gly Cys Gly Thr Cys Cys Ala Gly Ala Gly Thr Cys Gly Cys
1               5                   10                  15
Cys Gly Cys Cys Gly Cys Cys Gly Cys Cys Gly Gly Cys Cys Cys Cys
                20                  25                  30
Cys Cys Gly Ala Gly Thr Gly Thr Cys Cys Gly Gly Gly Cys Cys Cys
        35                  40                  45
Cys Cys
    50

<210> SEQ ID NO 403
<211> LENGTH: 50
<212> TYPE: PRT
<213> ORGANISM: Mus musculus

<400> SEQUENCE: 403

Cys Gly Cys Thr Gly Gly Thr Thr Cys Thr Cys Cys Gly Cys
1               5                   10                  15
Thr Cys Cys Gly Gly Ala Ala Cys Cys Cys Cys Gly Cys Gly Gly
                20                  25                  30
Gly Gly Thr Thr Gly Gly Ala Cys Cys Gly Cys Cys Gly Cys Cys
        35                  40                  45
Cys Cys
    50

<210> SEQ ID NO 404
<211> LENGTH: 50
<212> TYPE: PRT
<213> ORGANISM: Mus musculus

<400> SEQUENCE: 404

Cys Gly Cys Cys Gly Ala Cys Cys Cys Cys Gly Ala Cys Cys
1               5                   10                  15
Gly Cys Cys Cys Cys Cys Cys Gly Ala Cys Gly Gly Ala Ala Gly
                20                  25                  30
Ala Ala Gly Gly Ala Gly Gly Gly Gly Gly Ala Ala Gly Ala Gly
        35                  40                  45
Ala Gly
    50

<210> SEQ ID NO 405
<211> LENGTH: 50

```
<212> TYPE: PRT
<213> ORGANISM: Mus musculus

<400> SEQUENCE: 405

Gly Gly Gly Ala Cys Gly Ala Cys Gly Gly Gly Cys Cys Cys Cys
1               5                   10                  15

Gly Cys Gly Gly Gly Ala Ala Gly Ala Gly Gly Gly Gly Ala Gly
                20                  25                  30

Gly Gly Cys Gly Gly Gly Cys Cys Cys Gly Gly Cys Gly Gly Ala
        35                  40                  45

Ala Ala
    50

<210> SEQ ID NO 406
<211> LENGTH: 50
<212> TYPE: PRT
<213> ORGANISM: Mus musculus

<400> SEQUENCE: 406

Gly Gly Cys Gly Cys Cys Gly Cys Gly Cys Gly Gly Ala Ala Ala Ala
1               5                   10                  15

Cys Cys Gly Cys Gly Gly Cys Cys Cys Gly Gly Gly Gly Gly Cys
                20                  25                  30

Gly Gly Ala Cys Cys Cys Gly Gly Cys Gly Gly Gly Gly Ala Ala
        35                  40                  45

Cys Ala
    50

<210> SEQ ID NO 407
<211> LENGTH: 50
<212> TYPE: PRT
<213> ORGANISM: Mus musculus

<400> SEQUENCE: 407

Cys Cys Cys Cys Cys Ala Cys Ala Cys Gly Cys Gly Cys Gly Gly
1               5                   10                  15

Ala Cys Ala Cys Gly Cys Cys Cys Gly Cys Cys Cys Gly Cys Cys
                20                  25                  30

Cys Cys Gly Cys Cys Ala Cys Gly Cys Ala Cys Cys Thr Cys Gly Gly
        35                  40                  45

Gly Ala
    50

<210> SEQ ID NO 408
<211> LENGTH: 50
<212> TYPE: PRT
<213> ORGANISM: Mus musculus

<400> SEQUENCE: 408

Cys Ala Cys Cys Cys Gly Cys Thr Thr Thr Gly Gly Gly Cys Thr Gly
1               5                   10                  15

Cys Ala Thr Thr Cys Cys Cys Ala Ala Gly Cys Ala Ala Cys Cys Cys
                20                  25                  30

Gly Ala Cys Thr Cys Cys Gly Gly Gly Ala Ala Gly Ala Cys Cys Cys
        35                  40                  45

Gly Ala
    50

<210> SEQ ID NO 409
```

<211> LENGTH: 50
<212> TYPE: PRT
<213> ORGANISM: Mus musculus

<400> SEQUENCE: 409

Thr Gly Gly Ala Gly Cys Gly Ala Gly Cys Cys Cys Cys Gly Cys
1               5                   10                  15
Gly Gly Gly Gly Ala Gly Gly Gly Ala Cys Cys Cys Gly Cys Gly
                20                  25                  30
Cys Cys Gly Gly Cys Ala Cys Cys Cys Gly Cys Cys Gly Gly Cys
            35                  40                  45
Thr Cys
    50

<210> SEQ ID NO 410
<211> LENGTH: 50
<212> TYPE: PRT
<213> ORGANISM: Mus musculus

<400> SEQUENCE: 410

Cys Gly Ala Gly Gly Cys Cys Gly Gly Cys Gly Thr Gly Cys Cys Cys
1               5                   10                  15
Cys Gly Ala Cys Cys Cys Gly Ala Cys Gly Cys Gly Ala Gly Gly
                20                  25                  30
Ala Cys Gly Gly Gly Cys Cys Gly Gly Cys Gly Cys Cys Gly
            35                  40                  45
Gly Gly
    50

<210> SEQ ID NO 411
<211> LENGTH: 50
<212> TYPE: PRT
<213> ORGANISM: Mus musculus

<400> SEQUENCE: 411

Thr Cys Cys Cys Cys Gly Gly Ala Gly Cys Gly Gly Gly Thr Cys Gly
1               5                   10                  15
Cys Gly Cys Cys Cys Gly Cys Cys Gly Cys Ala Cys Gly Cys Gly
                20                  25                  30
Cys Gly Gly Gly Ala Cys Gly Gly Ala Cys Gly Cys Thr Thr Gly Gly
            35                  40                  45
Cys Gly
    50

<210> SEQ ID NO 412
<211> LENGTH: 50
<212> TYPE: PRT
<213> ORGANISM: Mus musculus

<400> SEQUENCE: 412

Thr Cys Cys Ala Cys Ala Cys Gly Ala Ala Cys Gly Thr Gly Cys Gly
1               5                   10                  15
Thr Thr Cys Ala Ala Cys Gly Thr Gly Ala Cys Gly Gly Gly Cys Gly
                20                  25                  30
Ala Gly Ala Gly Gly Gly Cys Gly Gly Cys Cys Cys Cys Thr Thr
            35                  40                  45
Thr Cys
    50

```
<210> SEQ ID NO 413
<211> LENGTH: 50
<212> TYPE: PRT
<213> ORGANISM: Mus musculus

<400> SEQUENCE: 413

Thr Cys Cys Cys Ala Ala Gly Ala Cys Gly Ala Ala Cys Gly Gly Cys
1               5                   10                  15

Thr Cys Thr Cys Cys Gly Cys Ala Cys Cys Gly Gly Ala Cys Cys Cys
                20                  25                  30

Cys Gly Gly Thr Cys Cys Gly Ala Cys Gly Cys Cys Cys Gly Gly
            35                  40                  45

Cys Gly
    50

<210> SEQ ID NO 414
<211> LENGTH: 50
<212> TYPE: PRT
<213> ORGANISM: Mus musculus

<400> SEQUENCE: 414

Cys Cys Gly Cys Cys Gly Cys Gly Gly Gly Ala Cys Gly Ala Cys
1               5                   10                  15

Gly Cys Gly Gly Gly Gly Ala Cys Cys Cys Gly Cys Cys Gly Ala
                20                  25                  30

Gly Cys Gly Gly Gly Ala Cys Gly Gly Ala Cys Gly Gly Gly
            35                  40                  45

Ala Cys
    50

<210> SEQ ID NO 415
<211> LENGTH: 50
<212> TYPE: PRT
<213> ORGANISM: Mus musculus

<400> SEQUENCE: 415

Gly Cys Ala Cys Cys Gly Cys Cys Ala Cys Gly Gly Thr Gly Ala
1               5                   10                  15

Ala Gly Thr Gly Cys Gly Cys Cys Cys Gly Gly Cys Gly Gly Cys Gly
                20                  25                  30

Gly Cys Cys Gly Gly Thr Cys Gly Cys Cys Gly Gly Cys Gly Gly
            35                  40                  45

Gly Gly
    50

<210> SEQ ID NO 416
<211> LENGTH: 50
<212> TYPE: PRT
<213> ORGANISM: Mus musculus

<400> SEQUENCE: 416

Cys Cys Cys Ala Cys Cys Gly Gly Gly Cys Cys Cys Gly Ala Gly
1               5                   10                  15

Ala Gly Ala Gly Gly Cys Gly Ala Cys Gly Gly Ala Gly Gly Gly
                20                  25                  30

Gly Gly Thr Gly Gly Gly Ala Gly Ala Gly Cys Gly Gly Thr Cys Gly
            35                  40                  45

Cys Gly
    50
```

<210> SEQ ID NO 417
<211> LENGTH: 50
<212> TYPE: PRT
<213> ORGANISM: Mus musculus

<400> SEQUENCE: 417

Cys Cys Cys Gly Gly Cys Cys Cys Cys Ala Cys Cys Cys Cys
1               5                   10                  15

Ala Cys Gly Cys Cys Cys Gly Cys Cys Gly Gly Ala Gly Gly
            20                  25                  30

Cys Gly Gly Ala Cys Gly Gly Gly Gly Gly Ala Gly Ala Gly Gly
        35                  40                  45

Gly Ala
    50

<210> SEQ ID NO 418
<211> LENGTH: 50
<212> TYPE: PRT
<213> ORGANISM: Mus musculus

<400> SEQUENCE: 418

Thr Ala Thr Cys Thr Gly Gly Cys Thr Thr Cys Cys Thr Cys Gly Gly
1               5                   10                  15

Cys Cys Cys Cys Gly Gly Gly Ala Thr Thr Cys Gly Gly Cys Gly Ala
            20                  25                  30

Ala Ala Gly Cys Gly Cys Gly Gly Cys Cys Gly Gly Ala Gly Gly Gly
        35                  40                  45

Cys Thr
    50

<210> SEQ ID NO 419
<211> LENGTH: 50
<212> TYPE: PRT
<213> ORGANISM: Mus musculus

<400> SEQUENCE: 419

Cys Gly Cys Cys Gly Cys Cys Gly Ala Cys Cys Cys Cys Gly Thr Gly
1               5                   10                  15

Cys Gly Cys Thr Cys Gly Gly Cys Thr Thr Cys Gly Thr Cys Gly Gly
            20                  25                  30

Gly Ala Gly Ala Cys Gly Cys Gly Thr Gly Ala Cys Cys Gly Ala Cys
        35                  40                  45

Gly Gly
    50

<210> SEQ ID NO 420
<211> LENGTH: 50
<212> TYPE: PRT
<213> ORGANISM: Mus musculus

<400> SEQUENCE: 420

Gly Cys Gly Cys Cys Cys Cys Cys Cys Gly Cys Ala Cys Cys Cys
1               5                   10                  15

Gly Cys Cys Cys Cys Gly Thr Cys Cys Cys Cys Cys Cys Gly Cys
            20                  25                  30

Gly Gly Ala Cys Gly Gly Gly Ala Ala Gly Ala Ala Gly Gly Gly
        35                  40                  45

Ala Gly
    50

<210> SEQ ID NO 421
<211> LENGTH: 50
<212> TYPE: PRT
<213> ORGANISM: Mus musculus

<400> SEQUENCE: 421

Cys Gly Ala Ala Cys Cys Cys Gly Gly Ala Ala Cys Cys Cys
1               5                   10                  15

Cys Cys Gly Ala Cys Cys Cys Gly Cys Gly Gly Ala Gly Gly
            20                  25                  30

Gly Gly Ala Ala Gly Gly Gly Gly Ala Gly Ala Cys Gly Ala
        35                  40                  45

Gly Gly
    50

<210> SEQ ID NO 422
<211> LENGTH: 50
<212> TYPE: PRT
<213> ORGANISM: Mus musculus

<400> SEQUENCE: 422

Cys Ala Cys Cys Cys Gly Gly Gly Gly Gly Gly Cys Gly Ala Cys
1               5                   10                  15

Gly Ala Gly Gly Cys Gly Gly Gly Ala Cys Cys Gly Cys Cys
            20                  25                  30

Gly Gly Ala Cys Gly Gly Gly Ala Cys Gly Ala Cys Gly Gly
        35                  40                  45

Gly Gly
    50

<210> SEQ ID NO 423
<211> LENGTH: 50
<212> TYPE: PRT
<213> ORGANISM: Mus musculus

<400> SEQUENCE: 423

Gly Cys Cys Ala Ala Cys Cys Gly Ala Gly Gly Cys Thr Cys Thr
1               5                   10                  15

Thr Cys Gly Gly Cys Gly Cys Thr Gly Cys Cys Gly Thr Ala Thr Cys
            20                  25                  30

Gly Thr Thr Cys Cys Gly Cys Thr Thr Gly Gly Gly Cys Gly Gly Ala
        35                  40                  45

Thr Thr
    50

<210> SEQ ID NO 424
<211> LENGTH: 50
<212> TYPE: PRT
<213> ORGANISM: Mus musculus

<400> SEQUENCE: 424

Cys Cys Cys Gly Gly Gly Cys Cys Cys Cys Gly Gly Ala Cys Cys
1               5                   10                  15

Cys Cys Cys Gly Ala Gly Ala Gly Gly Gly Ala Cys Gly Ala Cys Gly
            20                  25                  30

```
Gly Ala Gly Gly Cys Gly Ala Cys Gly Gly Gly Gly Gly Thr Gly
        35                  40                  45
Gly Gly
    50

<210> SEQ ID NO 425
<211> LENGTH: 50
<212> TYPE: PRT
<213> ORGANISM: Mus musculus

<400> SEQUENCE: 425

Thr Gly Gly Ala Gly Gly Gly Gly Cys Gly Gly Cys Cys Cys Gly
1               5                   10                  15

Gly Cys Cys Cys Cys Cys Gly Cys Gly Ala Cys Cys Gly Cys Cys Cys
        20                  25                  30

Cys Cys Cys Thr Thr Cys Cys Gly Cys Cys Ala Cys Cys Cys
        35                  40                  45

Ala Cys
    50

<210> SEQ ID NO 426
<211> LENGTH: 50
<212> TYPE: PRT
<213> ORGANISM: Mus musculus

<400> SEQUENCE: 426

Gly Gly Gly Ala Gly Ala Gly Gly Cys Cys Gly Gly Gly Gly Gly
1               5                   10                  15

Ala Gly Ala Gly Cys Gly Cys Gly Gly Cys Gly Ala Cys Gly Gly
        20                  25                  30

Thr Ala Thr Cys Cys Gly Gly Cys Thr Cys Cys Cys Thr Cys Gly Gly
        35                  40                  45

Cys Cys
    50

<210> SEQ ID NO 427
<211> LENGTH: 50
<212> TYPE: PRT
<213> ORGANISM: Mus musculus

<400> SEQUENCE: 427

Cys Gly Cys Thr Gly Cys Thr Gly Cys Cys Gly Gly Gly Gly Gly
1               5                   10                  15

Cys Thr Gly Thr Ala Ala Cys Ala Cys Thr Cys Gly Gly Gly Cys
        20                  25                  30

Gly Gly Gly Gly Thr Gly Gly Thr Cys Cys Gly Gly Cys Cys Cys
        35                  40                  45

Cys Ala
    50

<210> SEQ ID NO 428
<211> LENGTH: 50
<212> TYPE: PRT
<213> ORGANISM: Mus musculus

<400> SEQUENCE: 428

Cys Gly Cys Cys Gly Cys Cys Gly Ala Cys Cys Cys Gly Thr Gly
1               5                   10                  15
```

```
Cys Gly Cys Thr Cys Gly Gly Cys Thr Thr Cys Gly Cys Thr Cys Cys
            20                  25                  30

Cys Cys Cys Cys Cys Ala Cys Cys Cys Cys Gly Ala Gly Ala Ala Gly
        35                  40                  45

Gly Gly
    50
```